(12) United States Patent
Wyss-Coray et al.

(10) Patent No.: US 10,947,311 B2
(45) Date of Patent: Mar. 16, 2021

(54) VCAM-1 MEDIATED METHODS AND COMPOSITIONS FOR TREATING AGING-ASSOCIATED IMPAIRMENTS

(71) Applicant: The Board of Trustees of the Leland Stanford Junior University, Stanford, CA (US)

(72) Inventors: Anton Wyss-Coray, Palo Alto, CA (US); Hanadie Yousef, San Mateo, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 15/356,404

(22) Filed: Nov. 18, 2016

(65) Prior Publication Data

US 2017/0145105 A1    May 25, 2017

Related U.S. Application Data

(60) Provisional application No. 62/258,068, filed on Nov. 20, 2015.

(51) Int. Cl.

| C07K 16/28 | (2006.01) |
| A61P 25/28 | (2006.01) |
| A61P 25/16 | (2006.01) |
| A61K 39/00 | (2006.01) |
| A61P 25/14 | (2006.01) |

(52) U.S. Cl.
CPC .. C07K 16/2863 (2013.01); A61K 39/001102 (2018.08); A61K 39/001166 (2018.08); A61P 25/14 (2018.01); A61P 25/16 (2018.01); A61P 25/28 (2018.01); A61K 2039/505 (2013.01); C07K 2317/76 (2013.01); C12N 2501/58 (2013.01)

(58) Field of Classification Search
CPC . C07K 16/2863; C07K 2317/76; A61P 25/28; A61P 25/16; A61P 25/14; A61K 39/001166; A61K 39/001102; A61K 2039/505; C12N 2501/58
See application file for complete search history.

(56) References Cited

U.S. PATENT DOCUMENTS

| 5,932,214 | A  | 8/1999 | Lobb et al. |
| 6,123,915 | A  | 9/2000 | Masinovsky et al. |
| 6,252,043 | B1 | 6/2001 | Hession et al. |
| 7,655,417 | B2 | 2/2010 | Chung et al. |
| 7,682,613 | B2 | 3/2010 | Fabene et al. |
| 2003/0153731 | A1 | 8/2003 | Hession et al. |
| 2010/0172902 | A1 | 7/2010 | Chung et al. |
| 2014/0255303 | A1 | 9/2014 | Ghezzi et al. |

FOREIGN PATENT DOCUMENTS

| CN | 101294197 A | 10/2008 |
| CN | 101294199 A | 10/2008 |
| EP | 1616883 B1 | 12/2008 |
| EP | 2 484 381 A1 * | 8/2012 |
| EP | 2029164 B1 | 12/2015 |
| WO | WO 93/14220 A1 | 7/1993 |
| WO | WO 00/17392 A1 | 3/2000 |
| WO | WO 01/70757 A2 | 9/2001 |
| WO | WO 2009/118204 A2 | 10/2009 |
| WO | WO 2010/114312 A2 | 10/2010 |
| WO | WO 2013/160676 A1 | 10/2013 |

OTHER PUBLICATIONS

McCaulley and Grush, International Journal of Alzheimer's Disease, vol. 2015, published Oct. 21, 2015.*
Park et al., Atherosclerosis, 226:356-363, (Year: 2013).*
Oguchi et al., Arterioscler Thromb Vasc Biol. 20:1729-1736, (Year: 2000).*
Rose-John, Pharmacological Research, 71:19-22, (Year: 2013).*
Millonig et al. J Neuroimmunol., 227:190-194, (Year: 2010).*
Ewers et al., Exp Gerontol. Jan. 2010 ; 45(1): 75. (Year: 2010).*
Montagne et al., Neuroimage, 63:760-770, (Year: 2012).*
Chin et al., Am. J. Physiol. 272 (Lung Cell. MOL. Physiol. 16):L219-L229, (Year: 1997).*
Evans et al., Journal of Cerebral Blood Flow & Metabolism 34, 785-793 (Year: 2014).*
Center for Drug Evaluation and Research, Application No. 125104, Clinical Pharmacology and Biopharmaceutics Review(s), 39 pages (2008).
Chen et al. "Molecular Pathways: VCAM-1 as a potential therapeutic target in metastasis", Clinical Cancer Research, vol. 18, No. 20, pp. 5520-5525 (Oct. 15, 2012).
Lee et al. "A novel human anti-VCAM-1 monoclonal antibody ameliorates airway inflammation and remodelling", J. Cell. Mol. Med., vol. 17, No. 10, pp. 1271-1281 (2013).
Liu et al. "Matrine inhibits the expression of adhesion molecules in activated vascular smooth muscle cells", Molecular Medicine Reports, vol. 13, No. 3, pp. 2313-2319 (Mar. 2016).
Miyake et al. "A VCAM-like Adhesion Molecule on Murine Bone Marrow Stromal Cells Mediates Binding of Lymphocyte Precursors in Culture", The Journal of Cell Biology, vol. 114, No. 3, pp. 557-565 (Aug. 1991).
Moss et al. "Nutraceutical therapies for atherosclerosis", Nature Reviews Cardiology: Review, vol. 13, pp. 513-532 (Jul. 7, 2016).
Stegall et al. "Prolongation of islet allograft survival with an antibody to vascular cell adhesion molecule 1", Surgery, vol. 118, No. 2, pp. 366-370 (Aug. 1995).
Terpos et al. "Increased circulating VCAM-1 correlates with advanced disease and poor survival in patients with multiple myeloma: reduction by post-bortezomib and lenalidomide treatment", Blood Cancer Journal, vol. 6, e428, pp. 1-7 (May 27, 2016).
Zhan et al. "The inhibitory effect of photodynamic therapy and of an anti-VCAM-1 monoclonal antibody on the in vivo growth of C6 glioma xenografts", Brazilian Journal of Medical and Biological Research, vol. 44, No. 5, pp. 389-496 (Apr. 2011).

* cited by examiner

*Primary Examiner* — Kimberly Ballard
*Assistant Examiner* — Stacey N Macfarlane
(74) *Attorney, Agent, or Firm* — Kyle A. Gurley; Bret E. Field; Bozicevic, Field & Francis, LLP

(57) ABSTRACT

Methods of treating an adult mammal for an aging-associated impairment are provided. Aspects of the methods include reducing cell surface VCAM-1 activity in the mammal in a manner sufficient to treat the mammal for the aging-associated impairment. A variety of aging-associated impairments may be treated by practice of the methods, which impairments include cognitive impairments.

15 Claims, 22 Drawing Sheets
(16 of 22 Drawing Sheet(s) Filed in Color)
Specification includes a Sequence Listing.

Figure 1: sVCAM1 increases systemically with aging and heterochronic parabiosis
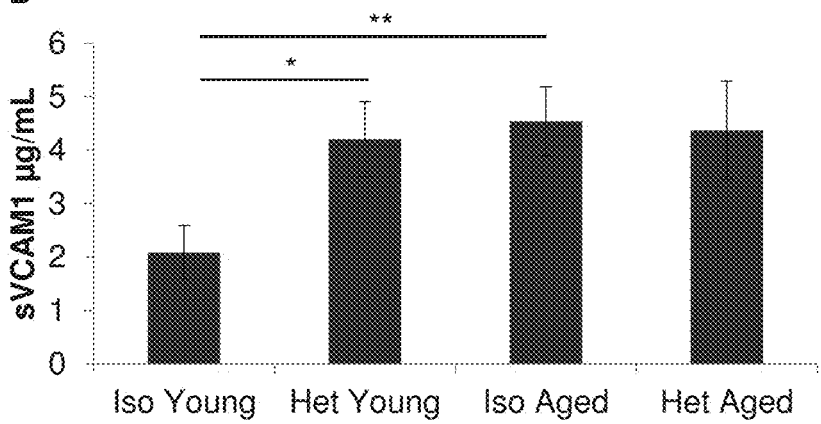

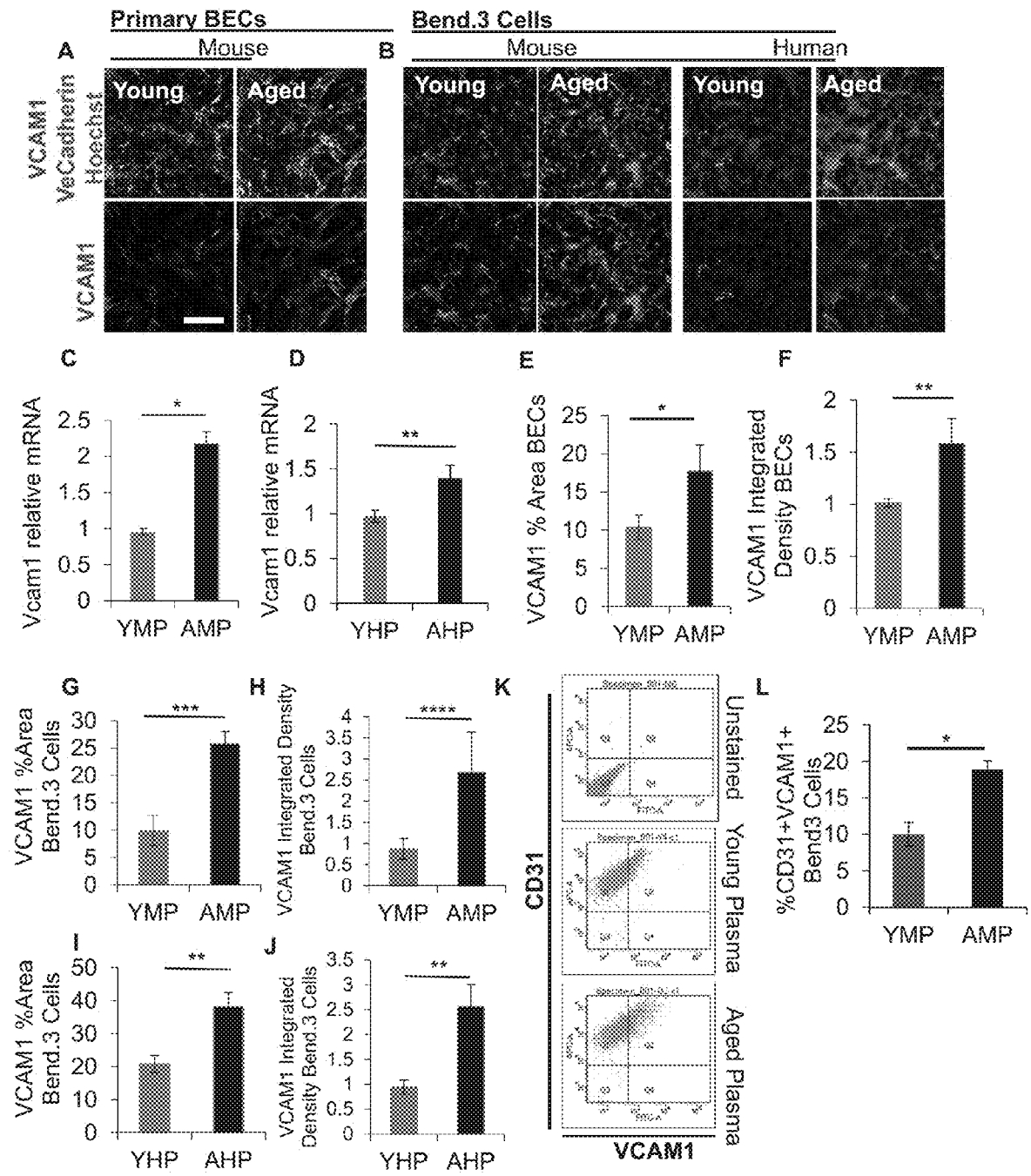
Figure 2: Aged Plasma induces VCAM1 Expression on BECs

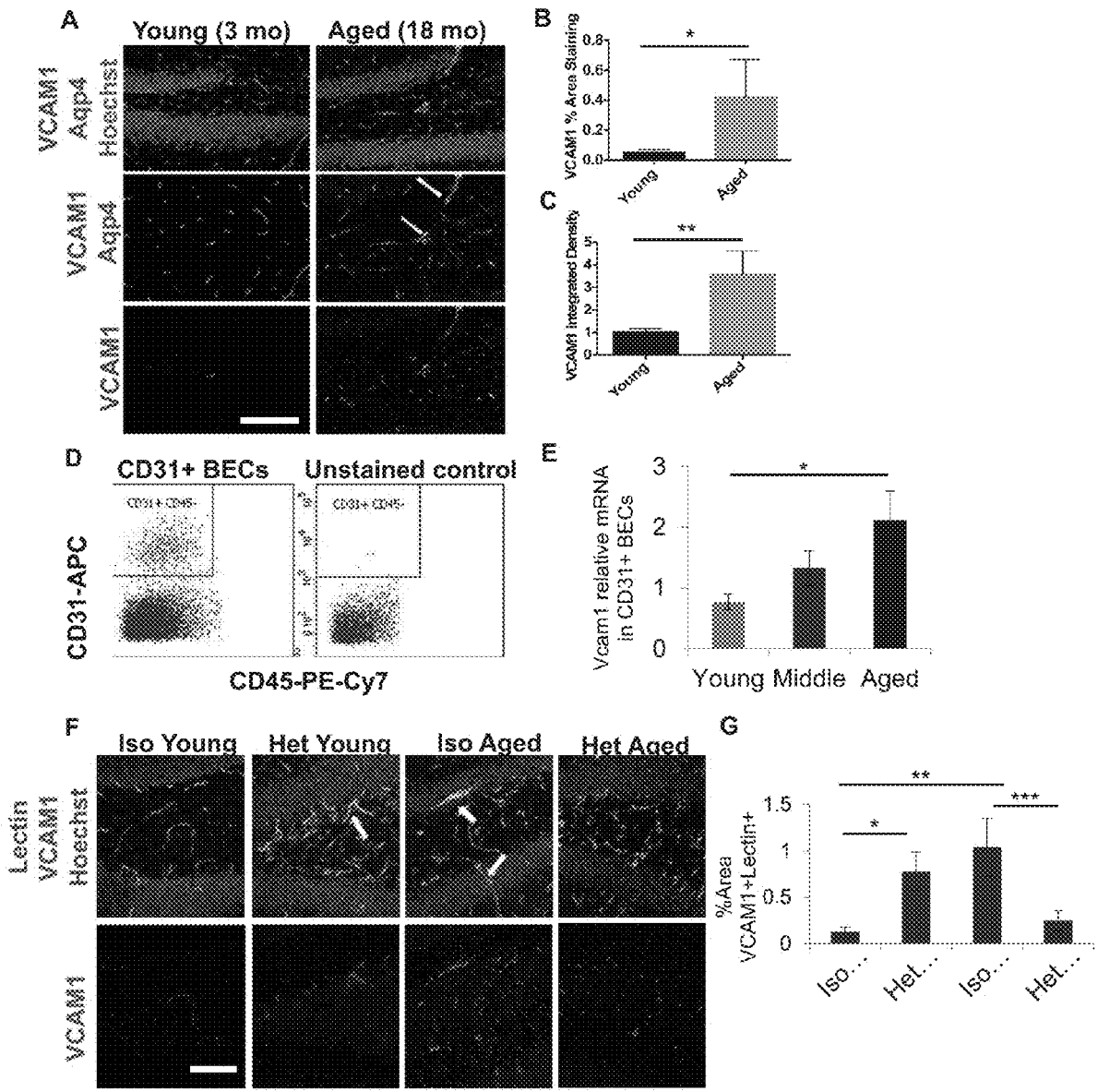
Figure 3: VCAM1 increases with age and is regulated by the systemic milieu

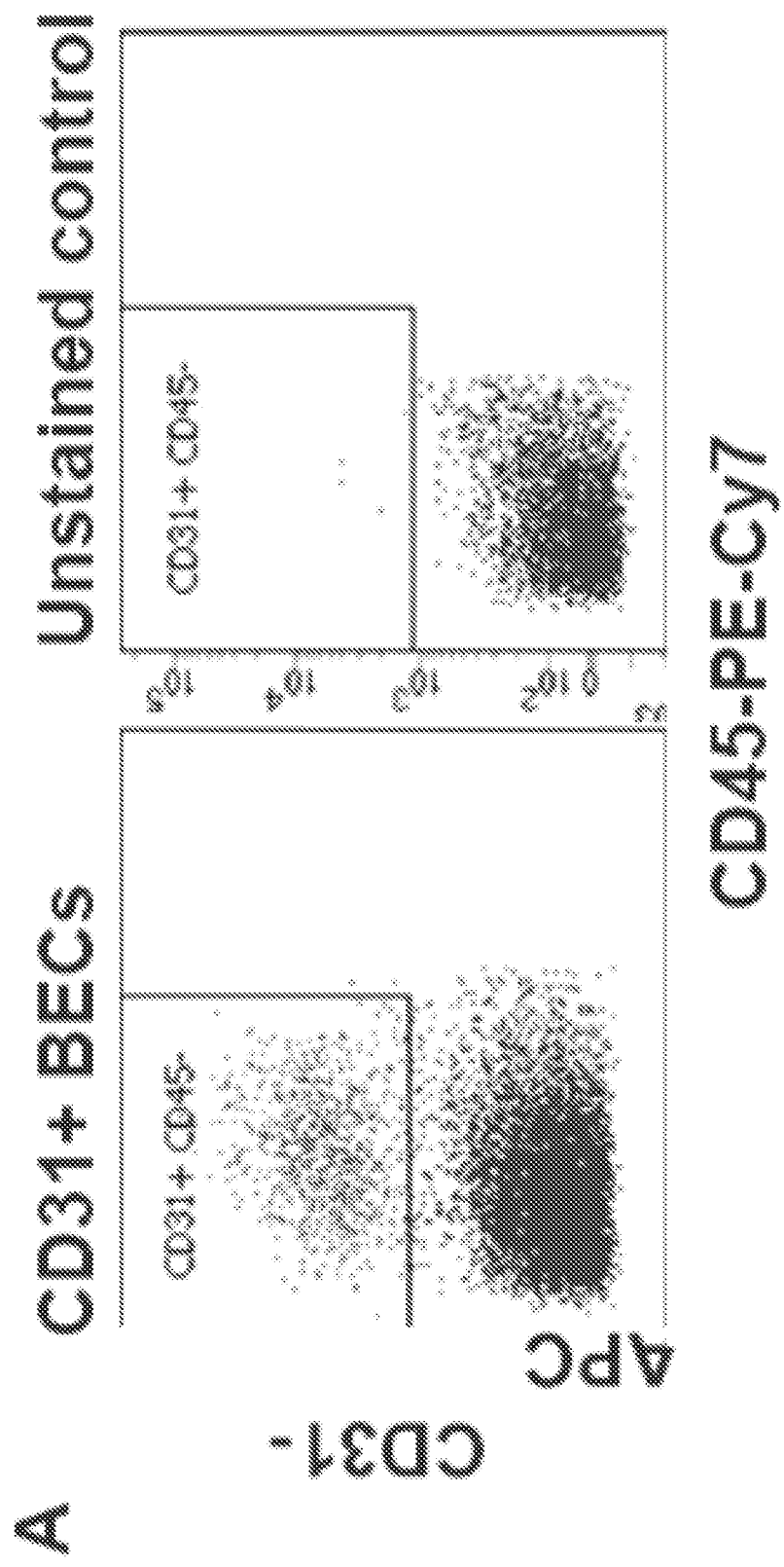
Figure 4: BEC-specific ADAM17 decreases with aging and is inhibited by aged plasma Figure 4 (CON'T): BEC-specific ADAM17 decreases with aging and is inhibited by aged plasma
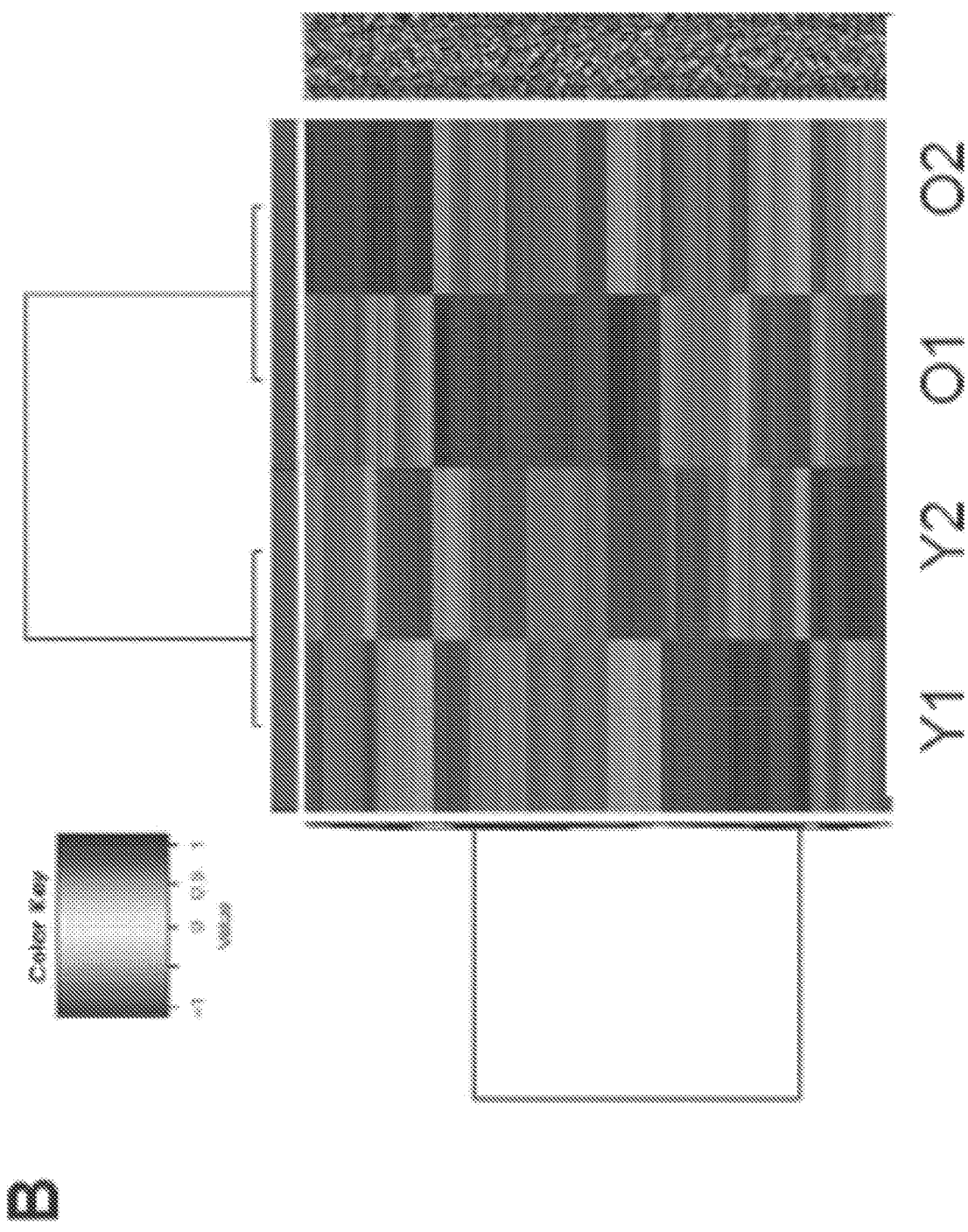

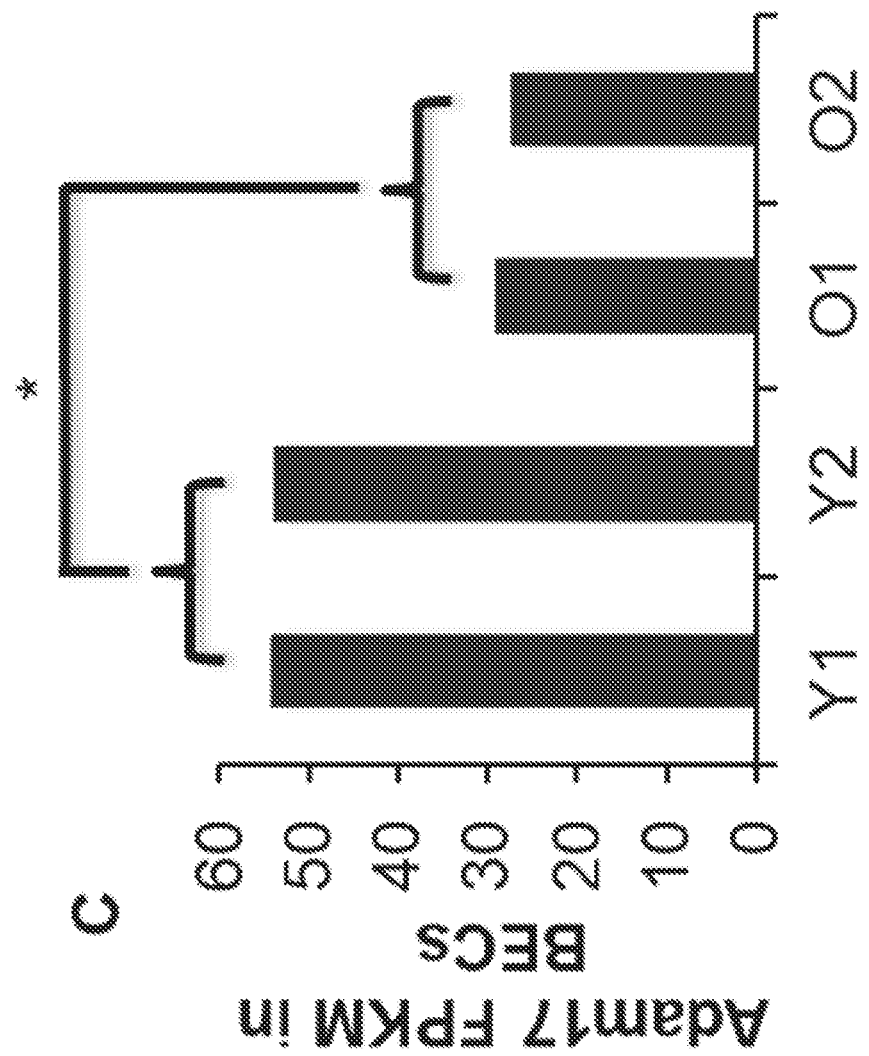
Figure 4 (CON'T): BEC-specific ADAM17 decreases with aging and is inhibited by aged plasma

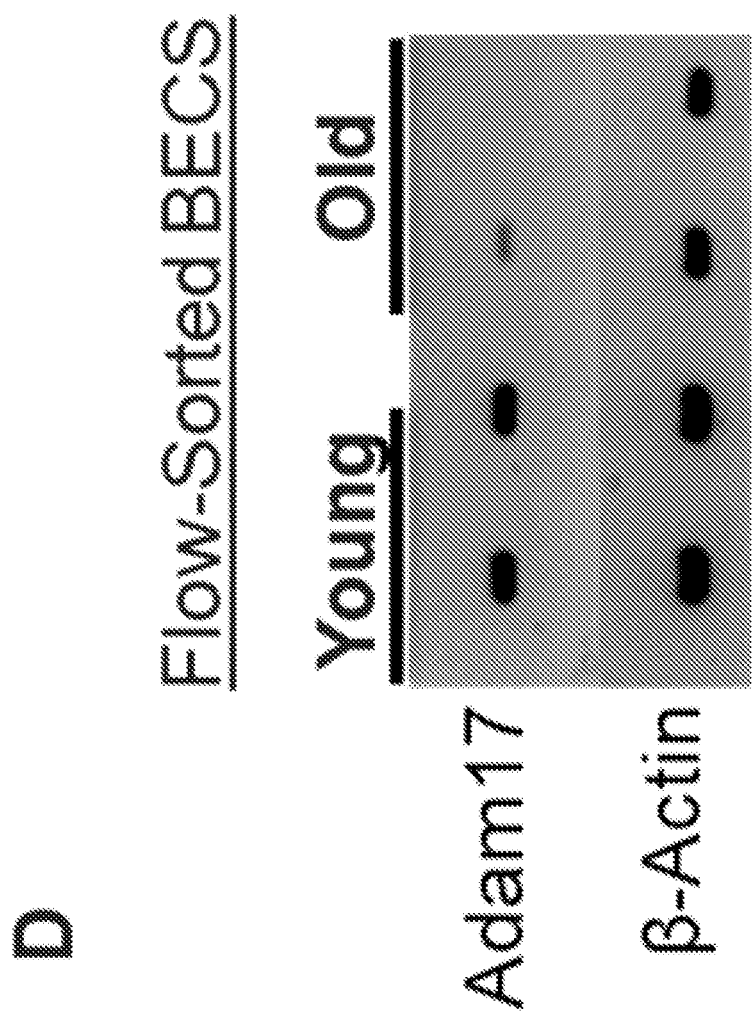
Figure 4 (CON'T): BEC-specific ADAM17 decreases with aging and is inhibited by aged plasma Figure 4 (CON'T): BEC-specific ADAM17 decreases with aging and is inhibited by aged plasma
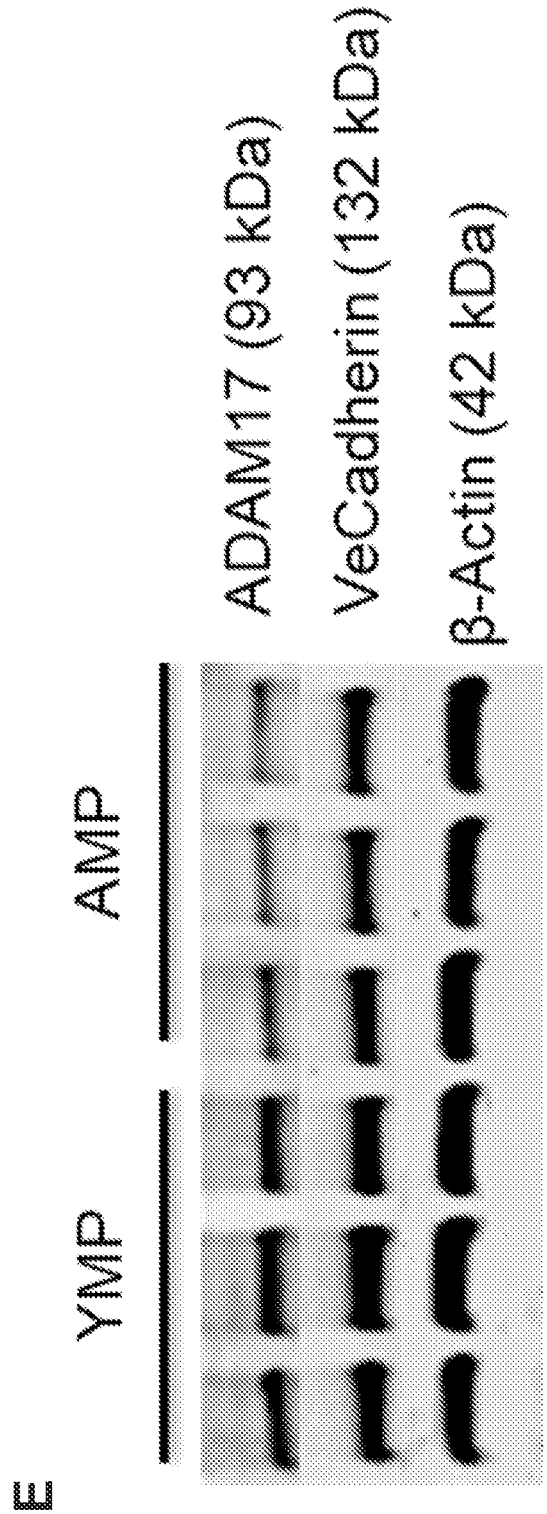

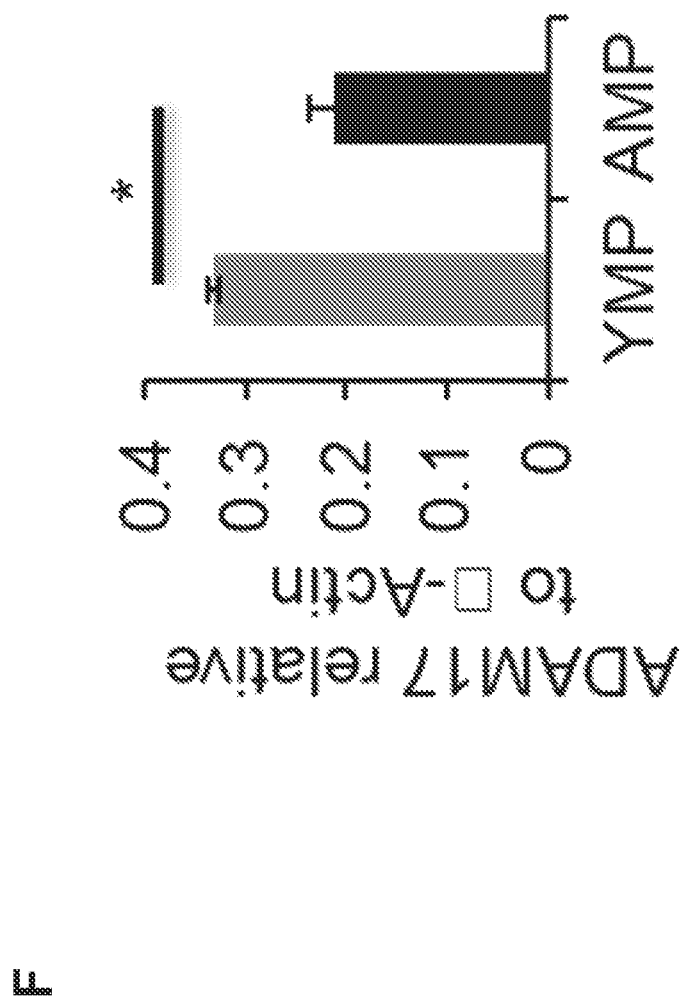
Figure 4 (CONT'D): BEC-specific ADAM17 decreases with aging and is inhibited by aged plasma
F

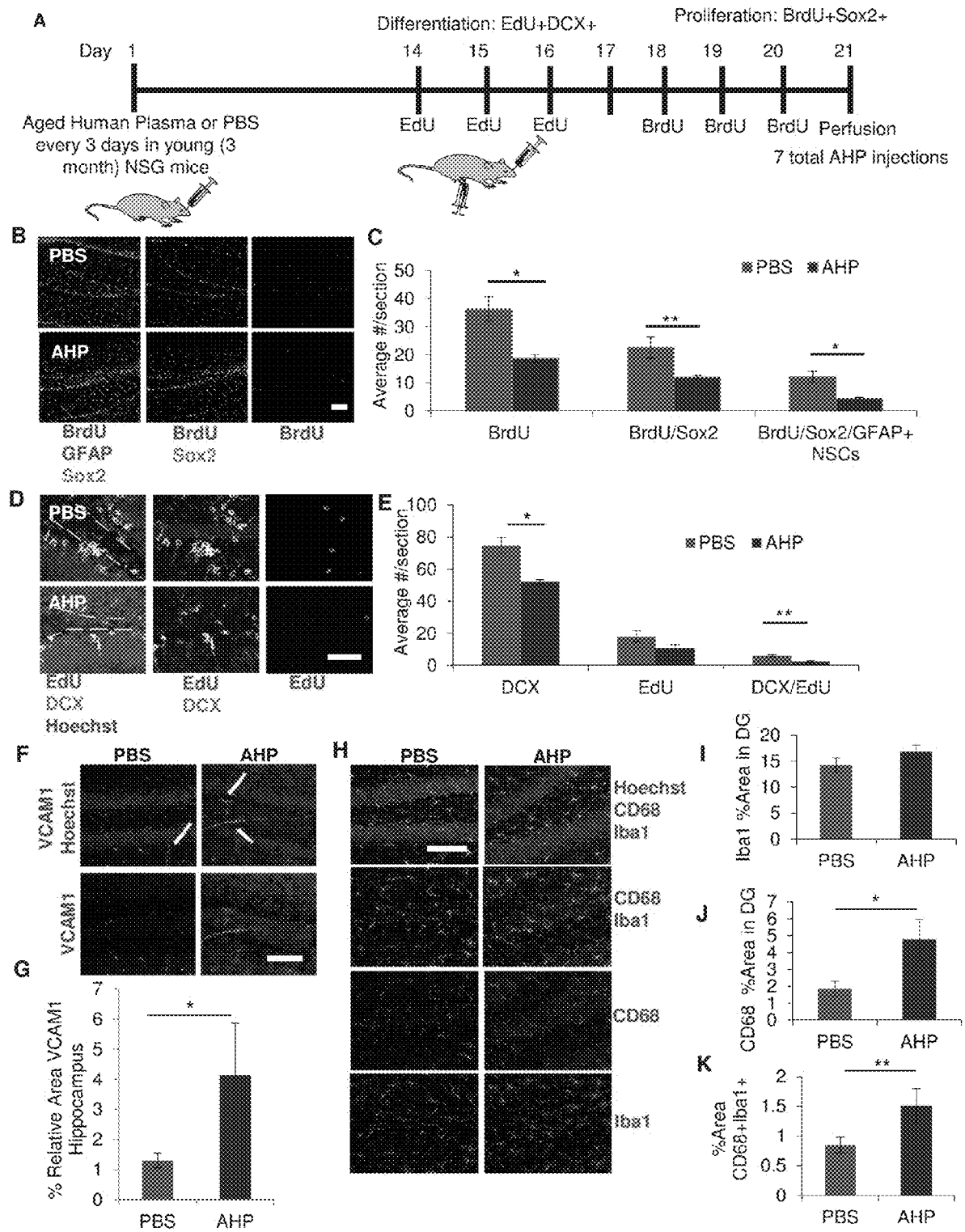
Figure 5. Immunodeficient mice exposed to an aged human systemic milieu over 3 weeks have decreased neurogenesis, increased VCAM1, and increased microglial reactivity Figure 7. Neutralizing monoclonal VCAM1 antibody prevents inhibitory effects of aged human plasma on hippocampal neurogenesis Figure 8. Neutralizing monoclonal VCAM1 antibody prevents microglial activation while increasing microglial expression in aged human plasma treated NSG mice Figure 9. VCAM1 increases with age in the cortex Figure 12
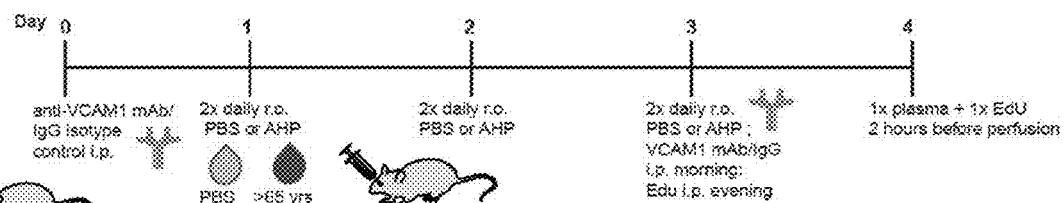
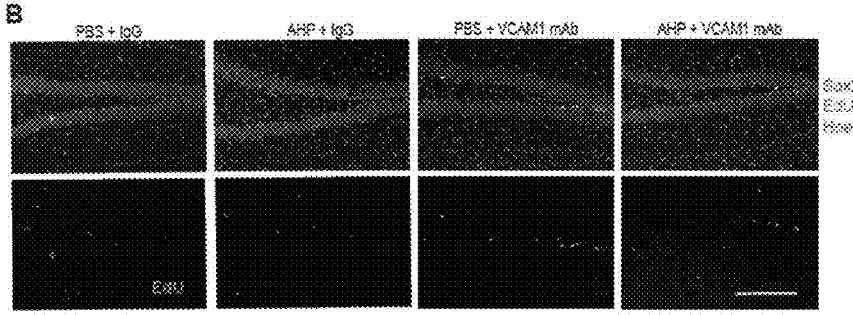
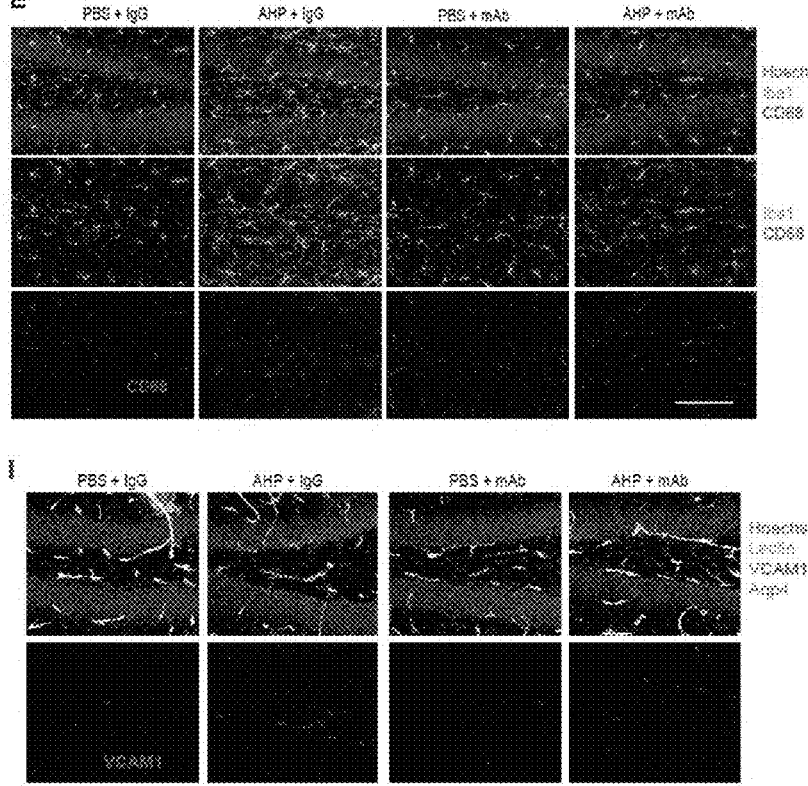
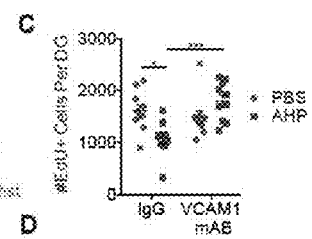
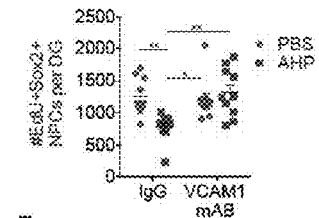
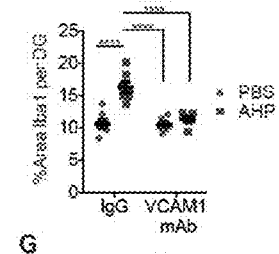
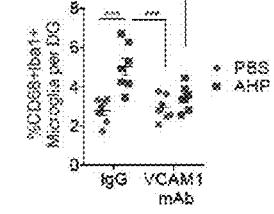
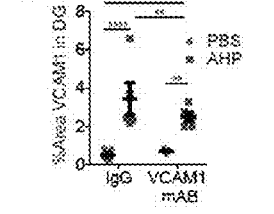

VCAM-1 MEDIATED METHODS AND COMPOSITIONS FOR TREATING AGING-ASSOCIATED IMPAIRMENTS

CROSS-REFERENCE TO RELATED APPLICATION

Pursuant to 35 U.S.C. § 119 (e), this application claims priority to the filing date of the U.S. Provisional Patent Application Ser. No. 62/258,068, filed Nov. 20, 2015, the disclosure of which is incorporated herein by reference.

GOVERNMENT RIGHTS

This invention was made with Government support under contract AG047820 awarded by the National Institutes of Health. The Government has certain rights in the invention.

INTRODUCTION

Aging in an organism is accompanied by an accumulation of changes over time. In the nervous system, aging is accompanied by structural and neurophysiological changes that drive cognitive decline and susceptibility to degenerative disorders in healthy individuals. (Heeden & Gabrieli, "Insights into the ageing mind: a view from cognitive neuroscience," Nat. Rev. Neurosci. (2004) 5: 87-96; Raz et al., "Neuroanatomical correlates of cognitive aging: evidence from structural magnetic resonance imaging," Neuropsychology (1998) 12:95-114; Mattson & Magnus, "Ageing and neuronal vulnerability," Nat. Rev. Neurosci. (2006) 7: 278-294; and Rapp & Heindel, "Memory systems in normal and pathological aging," Curr. Opin. Neurol. (1994) 7:294-298). Included in these changes are synapse loss and the loss of neuronal function that results. Thus, although significant neuronal death is typically not observed during the natural aging process, neurons in the aging brain are vulnerable to sub-lethal age-related alterations in structure, synaptic integrity, and molecular processing at the synapse, all of which impair cognitive function.

In addition to the normal synapse loss during natural aging, synapse loss is an early pathological event common to many neurodegenerative conditions, and is the best correlate to the neuronal and cognitive impairment associated with these conditions. Indeed, aging remains the single most dominant risk factor for dementia-related neurodegenerative diseases such as Alzheimer's disease (AD) (Bishop et al., "Neural mechanisms of ageing and cognitive decline," Nature (2010) 464: 529-535 (2010); Heeden & Gabrieli, "Insights into the ageing mind: a view from cognitive neuroscience," Nat. Rev. Neurosci. (2004) 5:87-96; Mattson & Magnus, "Ageing and neuronal vulnerability," Nat. Rev. Neurosci. (2006) 7:278-294).

As human lifespan increases, a greater fraction of the population suffers from aging-associated cognitive impairments, making it crucial to elucidate means by which to maintain cognitive integrity by protecting against, or even counteracting, the effects of aging (Hebert et al., "Alzheimer disease in the US population: prevalence estimates using the 2000 census," Arch. Neurol. (2003) 60:1119-1122; Bishop et al., "Neural mechanisms of ageing and cognitive decline," Nature (2010) 464:529-535).

SUMMARY

Methods of treating an adult mammal for an aging-associated impairment are provided. Aspects of the methods include reducing cell surface VCAM-1 activity in the mammal in a manner sufficient to treat the mammal for the aging-associated impairment. A variety of aging-associated impairments may be treated by practice of the methods, which impairments include cognitive impairments.

BRIEF DESCRIPTION OF THE FIGURES

The invention is best understood from the following detailed description when read in conjunction with the accompanying drawings. The patent or application file contains at least one drawing executed in color. Copies of this patent or patent application publication with color drawing(s) will be provided by the Office upon request and payment of the necessary fee. It is emphasized that, according to common practice, the various features of the drawings are not to-scale. On the contrary, the dimensions of the various features are arbitrarily expanded or reduced for clarity. Included in the drawings are the following figures.

FIG. 1. Administration of aged blood plasma. Aged plasma injections sVCAM1 is increased by the aged systemic milieu. (A) Protein microarray shows increased expression of soluble VCAM1 in 3-month-old young mice paired with aged (18 month) mice (heterochronic) compared to young mice paired to other young mice (isochronic). Around 400 proteins were measured with antibody-based arrays, data were normalized and ranked by SAM and t-test. *p=0.004, n=8/group. (B) An ELISA was performed on plasma of isochronic and heterochronic young (3 month old) and aged (19 month old) C57BL6/J mice following 6 weeks of parabiosis. *p<0.04, **p<0.02, n=6 mice/group.

FIG. 2. Aged plasma induces VCAM1 on BECs. (A) Primary BECs and (B) Bend.3 cells were serum starved for 2 hours, the cultured in 5% young (3 month) or aged (18 month) pooled (n=3) mouse plasma (MP) or human plasma (<25 years or >65 years, HP) for 24 hours followed by PFA fixation and immunofluorescent staining for a marker of endothelial cells, VeCadherin (red), VCAM1 (green), and hoechst (blue) to label cell nuclei. Representative images are shown. Scale bar=100 µm. (C) qPCR of mRNA extracted from primary cultivated BECs after 24 hour treatment with 5% young or aged mouse plasma (as in (A)) reveals over a 2-fold increase in Vcam1 mRNA, normalized to GapDH. *p<0.02, n=3/group, error bars represent SD (D) qPCR of mRNA extracted from Bend.3 cells after 24 hour treatment with 5% young or aged human plasma (as in (A)) reveals over a 1.5-fold increase in Vcam1 mRNA, normalized to β-actin. **p<0.04, n=6/group, error bars represent SEM (E-H) Quantification of VCAM1% area immunopositive staining and integrated pixel intensity of thresholded images for primary BECs (E-F) and Bend.3 cells (G-H) treated with young or aged mouse plasma was performed using ImageJ, and integrated density normalized relative to young levels. *p<0.03, p<0.02, n=6/group, error bars represent SEM. *p<0.0004, **p<0.04, n=4/group, error bars represent SD (I-J) Quantification of VCAM1% area immunopositive staining and integrated pixel intensity of thresholded images for Bend.3 cells treated with young or aged human plasma was performed using ImageJ, and integrated density normalized relative to young levels. p<0.001, n=6/group, error bars represent SD (K) Flow cytometry was performed on Bend.3 cells treated as in (A) and stained with APC-conjugated CD31 and FITC-conjugated VCAM1 antibodies. Percent CD31+VCAM1+ cells quantified in (L). *p<0.005, n=6 replicates/group, error bars represent SEM.

FIG. 3. The aged systemic milieu increases VCAM1 in the hippocampus. (A) Representative immunofluorescence staining on one focal plane of a z-stack in the dentate gyrus of the hippocampus of young (3 month old) and aged (19 month) C57BL6/J male mice. 40 μm brain sections are stained with the astrocytic endfeet marker Aqp4 (red) in order to outline brain vasculature, VCAM1 (green), and hoechst (blue) to label cell nuclei. Arrows point to VCAM1+ Aqp4+ colocalization in the neurogenic niche of aged mice. Scale bar=100 μm. Quantification of VCAM1+ % area staining (B) and integrated pixel intensity normalized to young levels (C) of thresholded images in serial 40 um sections throughout the hippocampus. *p<0.05, **p<0.03, n=5/group. Error bars represent SD. (D) Flow sorting of CD31+CD45− BECs directly from murine cortex and hippocampi. (E) Vcam1 quantitative PCR of CD31+CD45− flow-sorted primary BECs. *p<0.05. n=4 young (3 month), 5 middle (8-10 month), and 8 aged (19 month) C57BL6/J male mice. Error bars represent SEM. (F) Representative immunofluorescence staining on one focal plane of a z-stack in the dentate gyrus of the hippocampus of isochronic and heterochronic young (3 month old) and aged (19 month) parabiont C57BL6/J male mice following 6 weeks of shared blood circulation. Sections were stained for VCAM1 (red), the endothelial marker Lectin (green), and hoechst (blue) to label cell nuclei. Arrows point to VCAM1+Lectin+ colocalization in the neurogenic niche of heterochronic young and isochronic aged mice. Scale bar=100 μm. Quantification of VCAM1+Lectin+ % area staining (G) of thresholded images in serial 40 um sections throughout the hippocampus. *p<0.006, p<0.007, *p<0.03, n=6-8 mice per group. Error bars represent SEM.

FIG. 4. BEC-specific ADAM17 decreases with aging and is inhibited by aged plasma. (A) Flow sorting of CD31+CD45− BECs directly from murine cortex and hippocampi. (B) Illumina HighSeq RNA-sequencing analysis of flow-sorted CD31+CD45− young and aged BECs using TopHat/BowTie for sequencing alignment to the mouse genome, followed by Cufflinks analysis to quantify the amount of mRNA transcripts by generating values for Fragments Per Kilobase of transcript per Million mapped reads (FPKM), and differential expression of BECs isolated from the cortex and hippocampi of n=2 young or 2 old pooled (n=2 mice) samples. FPKM values were assessed via R and generation of heat maps displaying up or down-differentially regulated genes in old brains as compared to young with a p<0.05 is shown. There are 800 significant (*p<0.05) genes differentially expressed in aged BECs as compared to young. Heat map shown. (C) FPKM values of Adam17 in young and aged flow-sorted CD31+CD45− pooled (n=2 brains/sample) BECs show 2-fold decrease in Adam17 mRNA expression with age. *p=0.02. (D) Agarose gel of PCR-amplified Adam17 cDNA isolated from CD31+ young and old BECs from cortex and hippocampi. (E) Western blot of the lysate of Bend.3 cells serum starved for 4 hours then treated for 24 hours with 5% young (3 month) or aged (19 month) pooled (n=3) mice plasma (MP). (F) Quantification of ADAM17 shows a 30% decrease in Bend.3 cells treated with aged mouse plasma. *p<0.02, n=3/group. Error bars represent SEM.

FIG. 5. Immunodeficient mice exposed to an aged human systemic milieu over 3 weeks have decreased neurogenesis, increased VCAM1, and increased microglial activity. A) Schematic. NSG mice received pooled (n=3) aged human plasma (AHP, >65 years) injections (150 μL) retroorbitally every 3 days for 3 weeks, totaling 7 injections. They also received daily EdU injections (150 mg/kg, i.p.) for 3 days, beginning two weeks after plasma treatment (Day 14), followed by daily BrdU injections (150 mg/kg, i.p.) beginning on day 18 for 3 days followed by perfusion and tissue analysis. (B) Representative immunofluorescence staining in the dentate gyrus of mice treated with PBS or AHP demonstrate a 40% reduction in BrdU+ (green) proliferating cells, a 50% reduction in BrdU+ and Sox2+ (grey) colabeled proliferating neural progenitor cells and triple labeled BrdU+, Sox2+, and GFAP+ (red) neural stem cells in mice treated systemically with AHP, as quantified in (C). Scale bar=100 μm. *p<0.02, **p<0.05. Student's t-test. (D) Representative immunofluorescence staining in the dentate gyrus of mice treated with PBS or AHP demonstrate a 25% reduction in EdU+ (red) proliferating cells, DCX+ (grey) immature neurons, and colabeled DCX+EdU+ proliferating immature neurons in mice treated systemically with AHP, as quantified in (E). Dotted lines represent the SGZ. Hoechst (blue) labels cell nuclei. Scale bar=50 μm. *p<0.03, **p<0.02. Student's t-test. (F) Representative immunofluorescence staining in the dentate gyrus demonstrates a two-fold increase in VCAM1 (green, arrows) expression in mice treated with AHP, as quantified in (G). *p<0.05. Student's t-test. Hoechst (blue) labels cell nuclei. Scale bar=100 μm. (H) Representative immunofluorescence staining in the dentate gyrus of CD68 (green), a glycoprotein expressed in the lysosome and used as a marker of activated macrophages and microglia, Iba1 (red), a microglial cell marker, and hoechst (blue) to label cell nuclei. Scale bar=100 μm. Quantification in (I) demonstrates little change in Iba1+ % area staining, while there is a three-fold increase in CD68+ % area staining (J) and a two-fold increase in CD68+Iba1+ colocalized % area staining (K) in mice treated with AHP. *p<0.04, **p<0.05. Student's t-test. n=6 PBS, 7 AHP treated mice. Error bars represent SEM.

Figure 7:
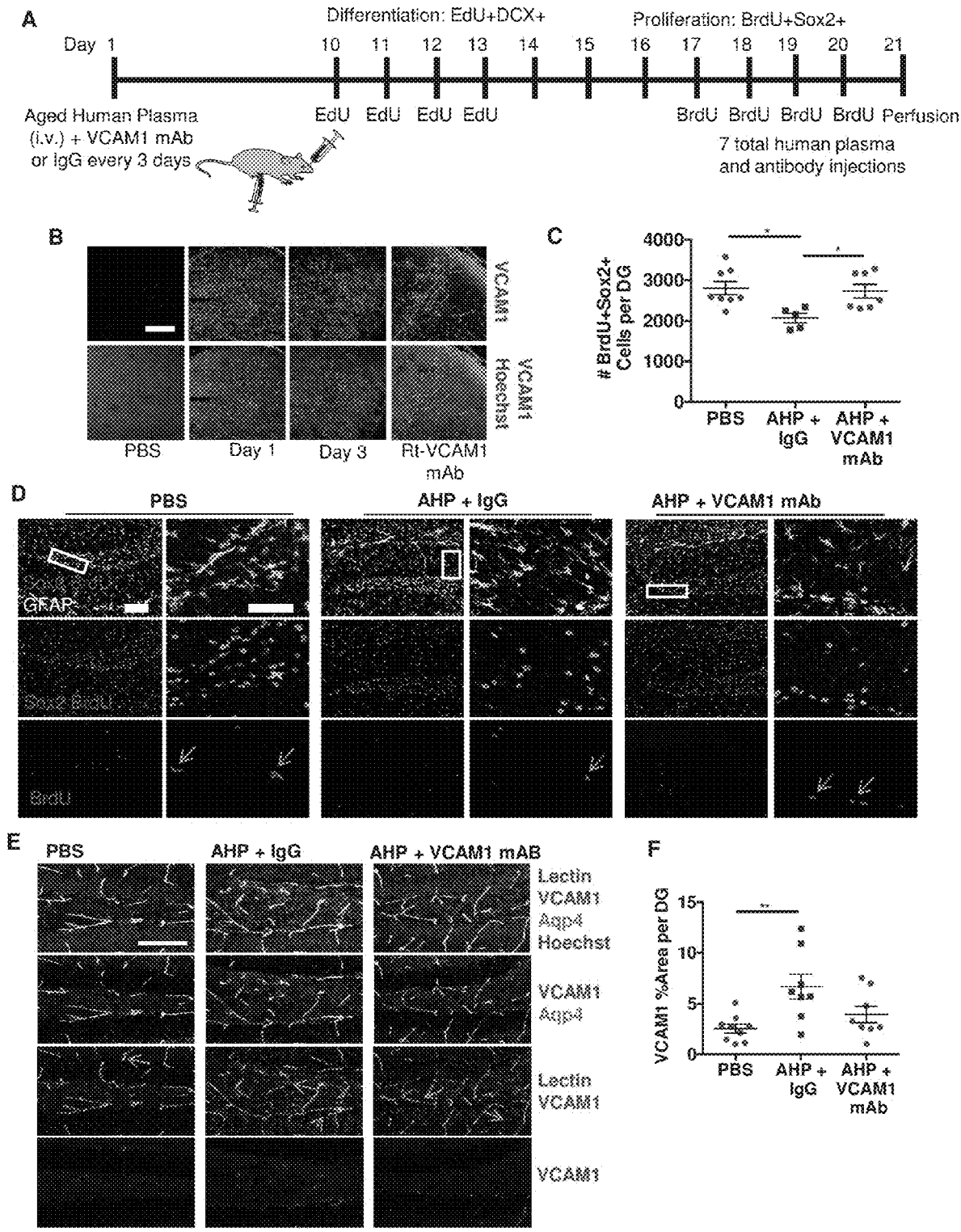

FIG. 7. Neutralizing monoclonal VCAM1 antibody prevents inhibitory effects of aged human plasma on hippocampal neurogenesis. (A) Schematic. NSG mice received pooled (n=3) aged human plasma (AHP, >65 years) injections (150 μL) retroorbitally every 3 days for 3 weeks, totaling 7 injections. In addition, mice received i.p. injections of monoclonal antibody targeting VCAM1 (12 mg/kg) or rat IgG isotype control (12 mg/kg) beginning on day 1 and every 3 days, for a total of 7 antibody injections. They also received EdU injections (150 mg/kg, i.p.) daily 4 times total, beginning on Day 10, followed by daily BrdU injections (150 mg/kg, i.p.) 4 times total, beginning on day 16, followed by perfusion and tissue analysis. n=10, 3 month old NSG mice per group. (B) Systemic antibody saturation was determined by collecting mouse serum 1 day and 3 days after antibody injection and incubating 10 um peripheral lymph node sections isolated from wildtype (C57BL6/J) lipopolysaccharide (LPS)-treated mice for two hours in serum followed by anti-rat alexa488-conjugated secondary for 2 hours. Incubation with primary monoclonal antibody against VCAM1 was used as a positive control stain. VCAM1+ (green) staining confirms antibody saturation in mouse serum on both days 1 and 3 after antibody injection. Hoechst (blue) labels cell nuclei. Scale bar=100 μm. (D) Representative immunofluorescence staining in the dentate gyrus of young NSG mice treated with PBS or AHP plus VCAM1 antibody or IgG demonstrate a 25% reduction in BrdU+ (red) and Sox2+ (green) colabeled proliferating neural progenitor cells in mice treated systemically with AHP+IgG isotype control antibody as compared to control PBS-treated mice. GFAP (grey) labels astrocytes and neural stem cells. Boxed areas in the SGZ of images in low (scale bar=100 μm) images are shown in right panels in high magnification (scale bar=50 μm). Quantified in (C) *p<0.02, error bars represent SEM. (E) Representative immunofluorescence staining in the dentate gyrus of VCAM1 (red), lectin (green), and Aqp4 (grey). Hoechst (blue) labels cell nuclei. Scale bar=100 μm. Quantification in (F) demonstrates a two-fold increase in VCAM1+Lectin+ (red-green colabeling, arrows) brain vasculature in mice treated with AHP plus IgG isotype control antibody, as quantified with % area staining in serial 40 μm sections throughout the hippocampal dentate gyrus. VCAM1 levels remain largely unchanged in mice treated with AHP plus VCAM1 monoclonal antibody, as compared to IgG control. **p<0.01. n=10 mice per group. Error bars represent SEM.

Figure 8:
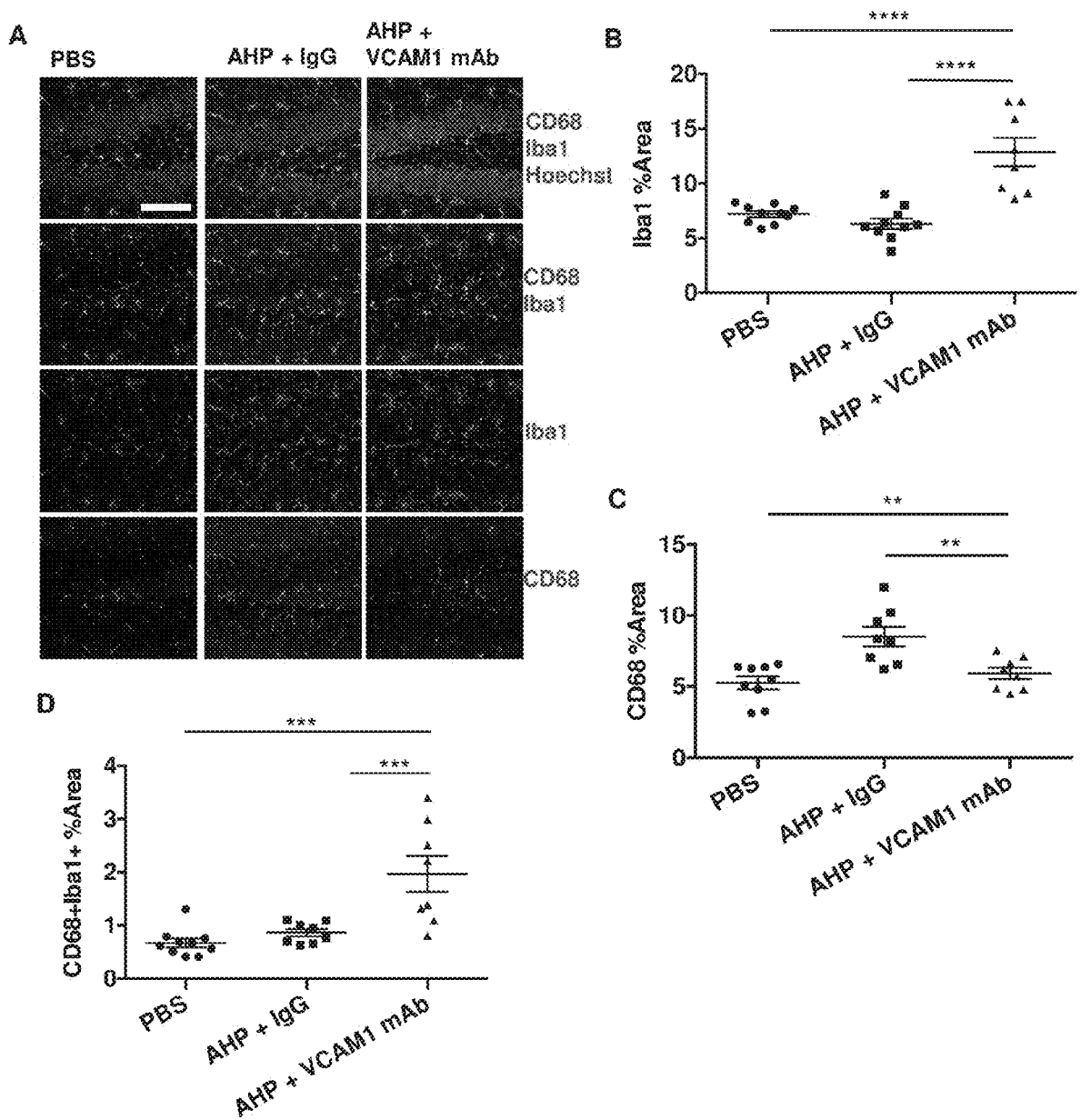

FIG. 8. Neutralizing monoclonal VCAM1 antibody prevents microglial activation while increasing microglial expression in aged human plasma treated NSG mice. (A) NSG mice treated as described in FIG. 7A. Representative immunofluorescence staining in the dentate gyrus of young NSG mice treated with PBS or AHP plus neutralizing monoclonal antibody targeting VCAM1 or IgG isotype control. Serial 40 μm sections throughout the hippocampal dentate gyrus were stained and imaged for CD68 (green), a glycoprotein expressed in the lysosome and used as a marker of activated macrophages and microglia, Iba1 (red), a microglial cell marker, and hoechst (blue) to label cell nuclei. Scale bar=100 μm. Quantification in (B) demonstrates a two-fold increase in Iba1+ % area staining in young mice treated with AHP plus VCAM1 antibody as compared to both PBS and AHP plus IgG treated cohorts. **p<0.0001. (C) There is a two-fold decrease in CD68+ % area staining and a two-fold increase in CD68+Iba1+ colocalized % area staining (D) in mice treated with AHP plus VCAM1 monoclonal antibody as compared to both PBS and AHP plus IgG treated cohorts. p<0.0006, *p<0.0002, **p<0.0 n=8-10 mice per group. Error bars represent SEM.

Figure 6:
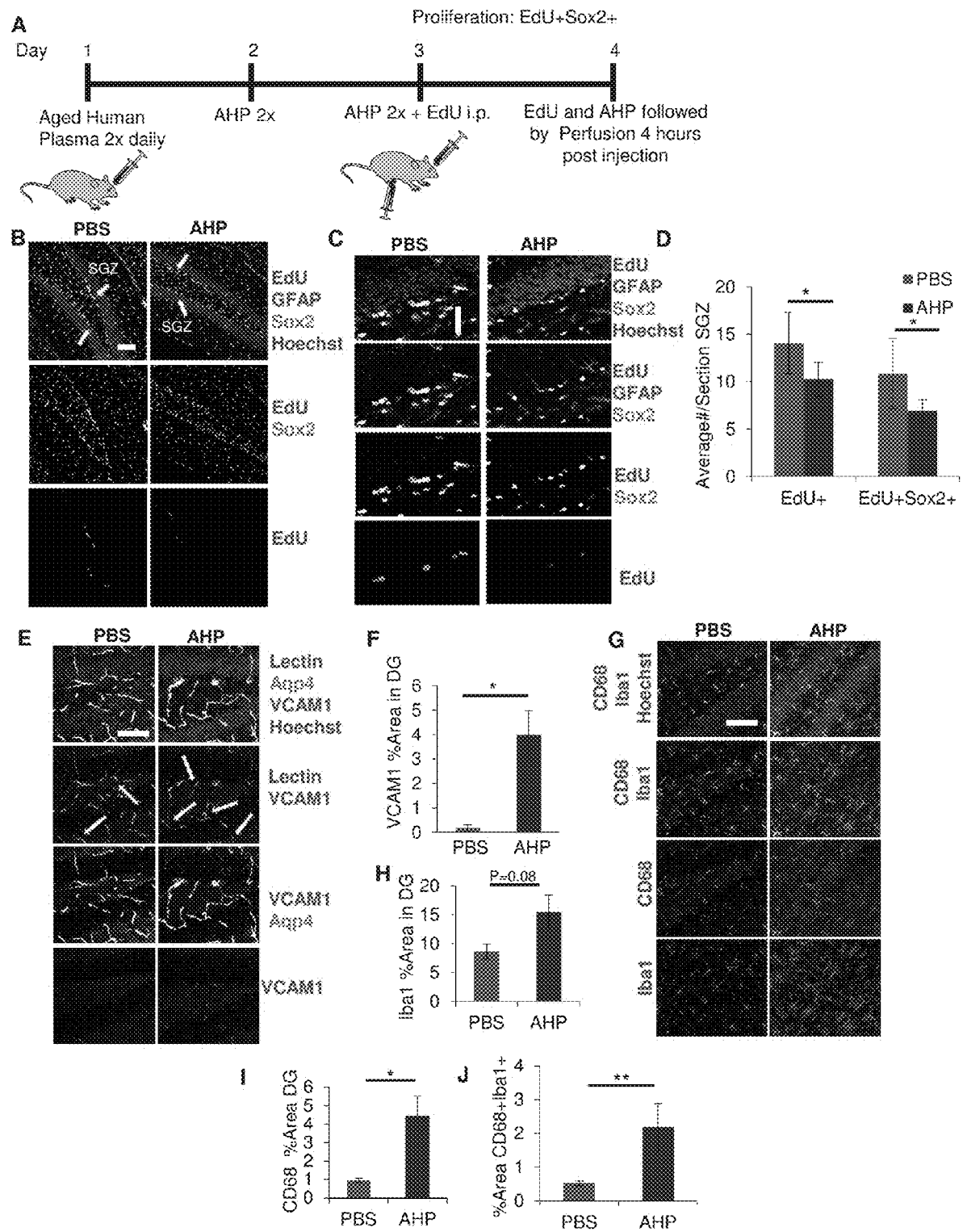
FIG. 6. Immunodeficient mice exposed to an aged human systemic milieu have decreased neurogenesis, increased cerebrovascular VCAM1, and increased microglial reactivity. (A) Schematic. NSG mice received pooled (n=3) aged human plasma (AHP, >65 years) injections (150 μL) retroorbitally twice daily in morning and evenings, with a final $7^{th}$ injection 4 hours before perfusion on Day 4. They also received EdU injections (150 mg/kg, i.p.) 16 hours and 4 hours before perfusion and tissue analysis. (B) Representative confocal immunofluorescence staining (6 sections/brain) in the dentate gyrus of young NSG mice treated with PBS or AHP demonstrate a 25% reduction in EdU+ (green) proliferating cells and EdU+ and Sox2+ (grey) colabeled proliferating neural progenitor cells in mice treated systemically with AHP. GFAP (red) labels astrocytes and neural stem cells. Scale bar=100 μm. Representative high magnification images are shown in (C). Scale bar=50 μm. Quantified in (D). *p<0.05, Student's t-test. (E) Representative confocal immunofluorescence staining in the DG of VCAM1 (red), lectin (green), and Aqp4 (grey). Hoechst (blue) labels cell nuclei. Scale bar=100 μm. Quantification in (F) demonstrates a four-fold increase in VCAM1+Lectin+ (red-green colabeling, arrows) brain vasculature in mice treated with AHP, as quantified with % area stain in 5, serial 40 μm sections throughout the hippocampal dentate gyrus and *p<0.03 Student's t-test. (G) Representative confocal immunofluorescence staining in the dentate gyrus of young NSG mice treated with PBS or AHP stained for CD68 (green), a glycoprotein expressed in the lysosome and used as a marker of activated macrophages and microglia, Iba1 (red), a microglial cell marker, and hoechst (blue) to label cell nuclei. Scale bar=100 μm. Quantification in (H) demonstrates an increase in Iba1+ % area staining (p=0.08), while there is a three-fold increase in CD68+ % area staining (I) and a two-fold increase in CD68+Iba1+ colocalized % area staining (J) in mice treated with AHP. *p<0.02, **p<0.05. Student's t-test. n=5 mice per group. All error bars represent SEM.
Figure 9:
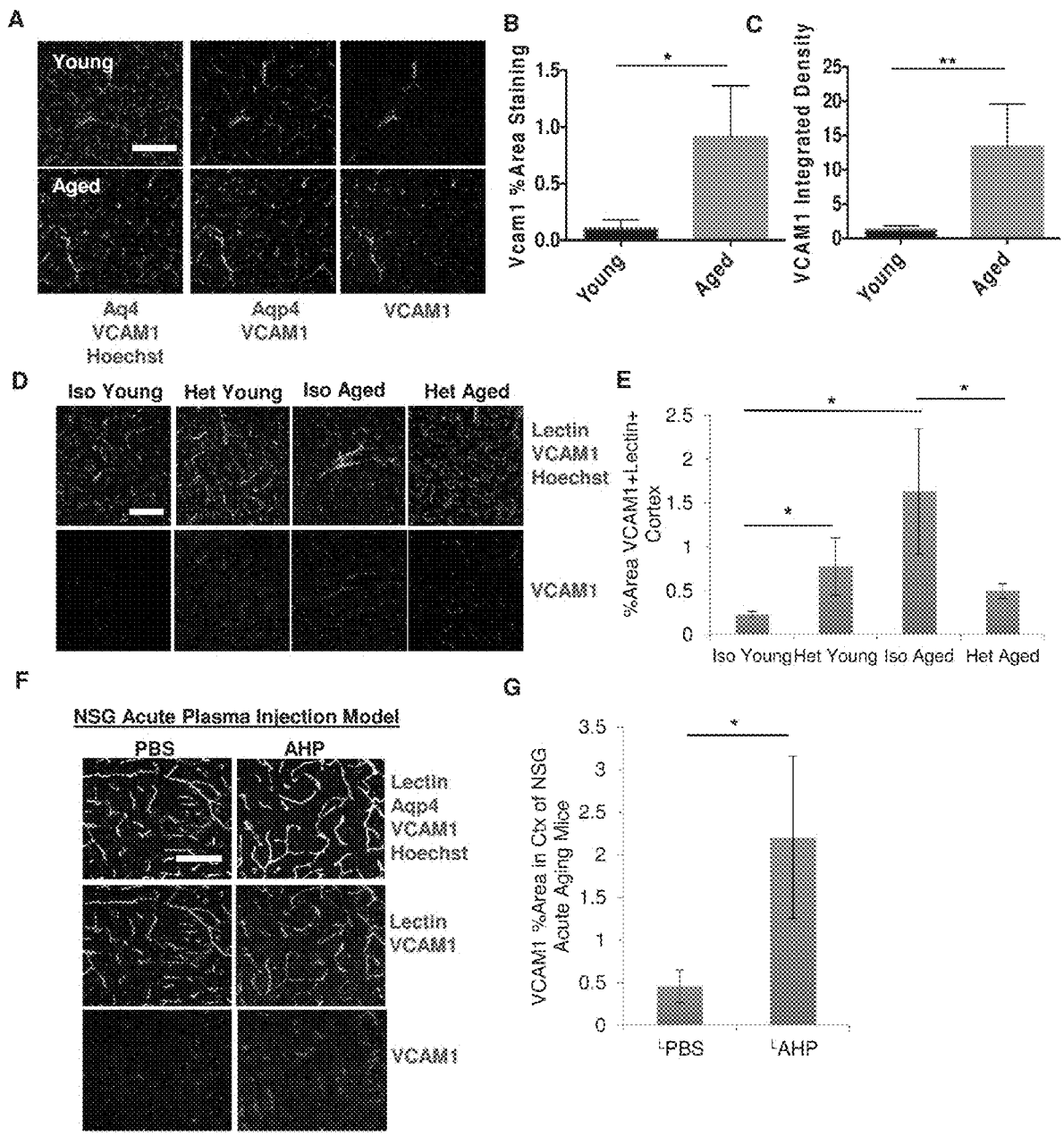

FIG. 9. VCAM1 increases with age and exposure to the aged systemic milieu in the cortex. (A) Representative immunofluorescence staining on one focal plane of a z-stack in the cortex of young (3 month old) and aged (19 month) C57BL6/J male mice. 40 μm brain sections are stained with the astrocytic endfeet marker Aqp4 (red) in order to outline brain vasculature, VCAM1 (green), and hoechst (blue) to label cell nuclei. Scale bar=100 μm. Quantification of VCAM1+% area staining (B) and integrated pixel intensity normalized to young levels (C) of thresholded images in 5, serial 40 um sections in cortex. *p<0.04, **p<0.03, n=3 mice per group. Error bars represent SD. (D) Representative immunofluorescence staining on one focal plane of a z-stack in the cortex of isochronic and heterochronic young (3 month old) and aged (19 month) parabiont C57BL6/J male mice following 6 weeks of shared blood circulation. Sections were stained for VCAM1 (red), the endothelial marker Lectin (green), and hoechst (blue) to label cell nuclei. Scale bar=100 μm. Quantification in (E) of VCAM1+Lectin+ % area staining of thresholded images in 5, serial 40 um sections in cortex. *p<0.05, n=6-8 mice per group. Error bars represent SD. (F) Representative immunofluorescence staining of a z-stack in the cortex of NSG mice treated as described in FIG. 6A. 40 μm sections were stained for VCAM1 (red), the endothelial marker Lectin (green), and hoechst (blue) to label cell nuclei. Scale bar=100 μm. Quantification in (G) of VCAM1+Lectin+% area staining of thresholded images in 5, serial 40 um sections. *p<0.04, n=5 mice per group. Error bars represent SD.

Figure 10:
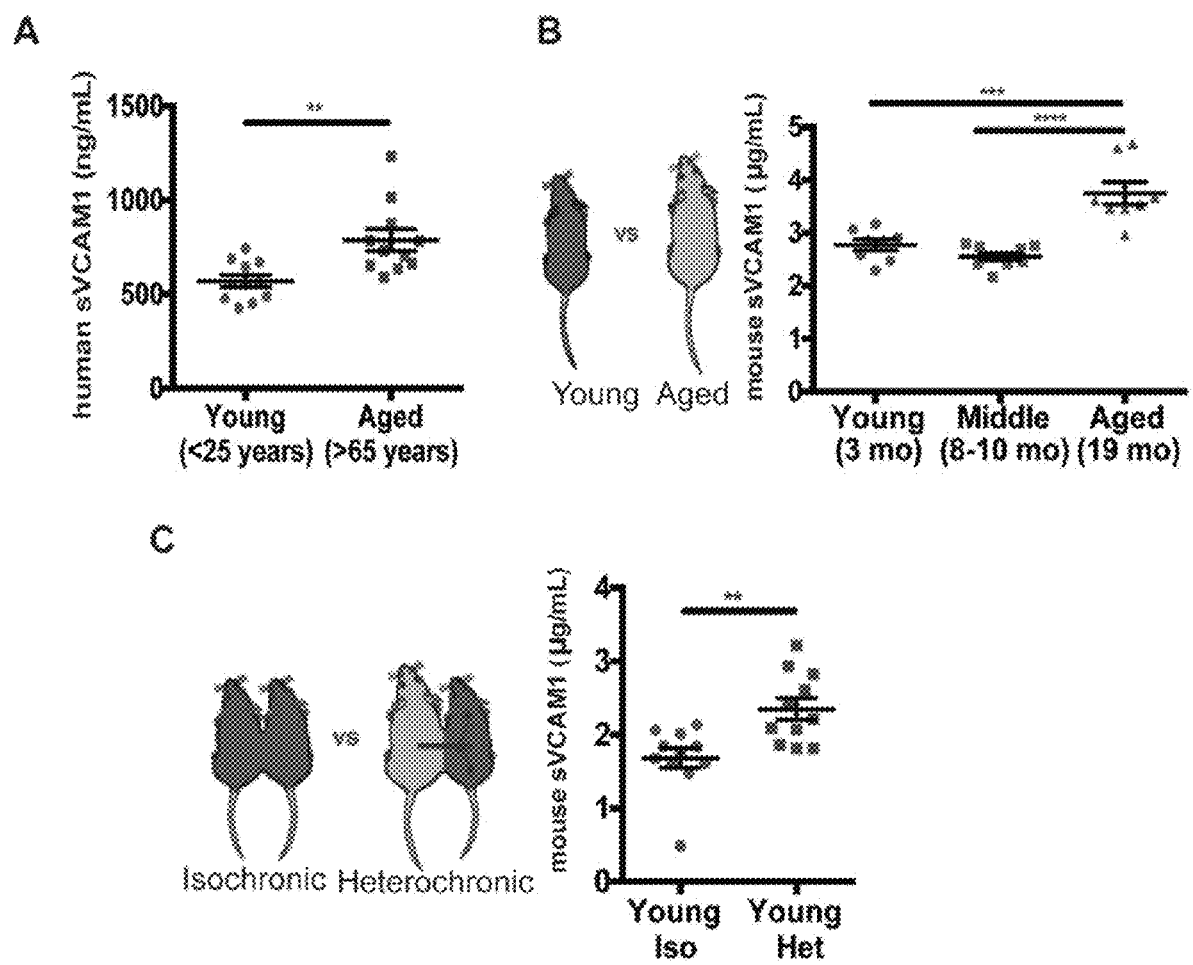

FIG. 10. sVCAM1 increases systemically with aging and exposure to aged blood circulation. (A) An enzyme-linked immunoabsorbent assay (ELISA) to detect human sVCAM1 was performed on plasma of eleven young (<25 years old) or aged healthy donors (>65 years old). p<0.005, Student's t-test. (B-C) Schematics of unpaired young versus aged mice (B), and young isochronic versus heterochronic parabionts (C). (B) Changes in plasma concentration of mouse sVCAM1 with age in young (3 months; n=8), middle-aged (8-10 months; n=10), and aged (19 months; n=8) C57Bl6/J mice. *p<0.001, analysis of variance (ANOVA) with Tukey's post-hoc test. (C) A mouse sVCAM1 ELISA was performed on young isochronic or heterochronic parabionts following 5 weeks of parabiosis. n=11 mice/group from two pooled parabiosis experiments. **p<0.003, ANOVA with Tukeys post-hoc test.

Figure 11:
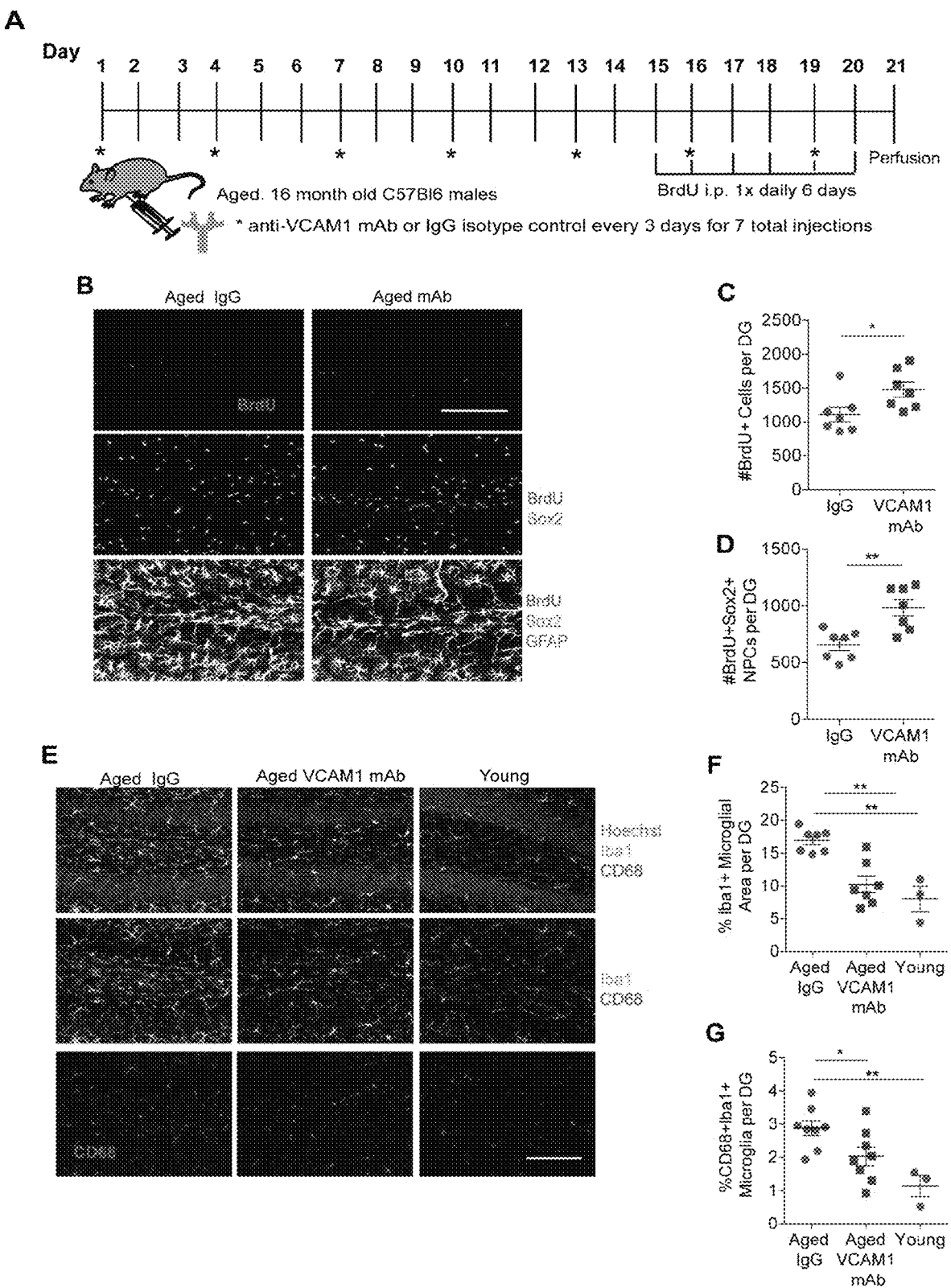

FIG. 11. Neutralizing monoclonal VCAM1 antibody enhances neurogenesis and reduces microglial activation in aged brains. (A) Experimental Setup. Aged (16 month old) mice received i.p. injections of monoclonal neutralizing antibody against mouse VCAM1 or rat IgG isotype control (9 mg/kg) every 3 days for 7 total injections. Mice also received BrdU daily (100 mg/kg i.p.) for the last 6 days prior to perfusion to label proliferating cells. n=7 mice/group. (B) Representative confocal images from the DG of brain sections immunostained for BrdU (red) to mark proliferating cells, colabeled with Sox2 (green) to label proliferating neural precursor cells and triple labeled with GFAP (white) to label activated neural stem cells; Scale bar=100 μm. Quantified in (C-D). *p<0.04, **p<0.003. Student's t-test. Neurogenesis was quantified by counting labeled cells in the neurogenic granular layer and hilus in 6 serial 40 μm sections throughout the hippocampal dentate gyrus. (E)

Representative confocal images (of 5 sections per mouse) from the DG of aged mice which received VCAM1 mAb or IgG. Young brain sections (n=3 mice) are also represented to serve as a comparative assessment of the level of microglial rejuvenation. All sections were immunostained for CD68 (red), Iba1 (green), and hoechst (blue) to label cell nuclei. Scale bar=100 µm. Iba1+ % area staining quantified in (F) **p<0.004, ANOVA with Tukey's post-hoc test. CD68+ Iba1+ colocalized % area staining quantified in (G) *p<0.002, ANOVA with Tukey's post-hoc test.

FIG. 12. Neutralizing monoclonal VCAM1 antibody prevents inhibitory effects of aged human plasma injections in an acute injection paradigm. (A) Experimental setup. 3 month old NSG mice received injections of monoclonal antibody targeting VCAM1 or rat IgG isotype control (9 mg/kg) on day 0 and morning of day 3. Mice were given r.o. injections (150 µl) of aged human plasma (AHP, >65 years, n=5 pooled individuals) or PBS as control twice daily for 7 total injections. Mice were pulsed with EdU (100 mg/kg, i.p.) 16 hours and 2 hours before perfusion to label proliferating cells. n=10 mice/group. (B) Representative confocal images from the DG of brain sections immunostained for EdU (green) to mark proliferating cells, colabeled with Sox2 (red) to label proliferating neural precursor cells. Hoechst (blue) labels cell nuclei; Scale bar=200 µm. Quantified in (C) *p<0.002, 2-way ANOVA with Tukey's post-hoc test and (D) p<0.004, 2-way ANOVA with Sidak's post-hoc test. Neurogenesis was quantified by counting labeled cells in the neurogenic granular layer and hilus in 6 serial, 40 µm sections throughout the hippocampal dentate gyrus. (E) Representative confocal images (of 5 sections per mouse, 7 mice/group analyzed) from the DG of NSG mice which received PBS or AHP along with VCAM1 mAb or IgG. All sections were immunostained for CD68 (red), Iba1 (green), and hoechst (blue) to label cell nuclei. Scale bar=100 µm. Iba1+ % area staining quantified in (F) ****p<0.0007, 2-way ANOVA with Tukey's post-hoc test. CD68+Iba1+ colocalized % area staining quantified in (G) *p<0.01, 2-way ANOVA with Tukey's post-hoc test. (H) Representative confocal images (5 sections/mouse, 5 mice/group analyzed) in the dentate gyrus of VCAM1 (red), lectin (green), and Aqp4 (white), a marker of astrocytic endfeet that line the blood vessel walls in the brain parenchyma. Hoechst (blue) labels cell nuclei. Scale bar=100 µm. Quantification in (I) demonstrates a three-fold increase in % area VCAM1+Lectin+ brain vasculature in AHP treated mice. **p<0.001. 2-way ANOVA with Tukey's post-hoc test. All error bars represent SEM.

Figure 13:
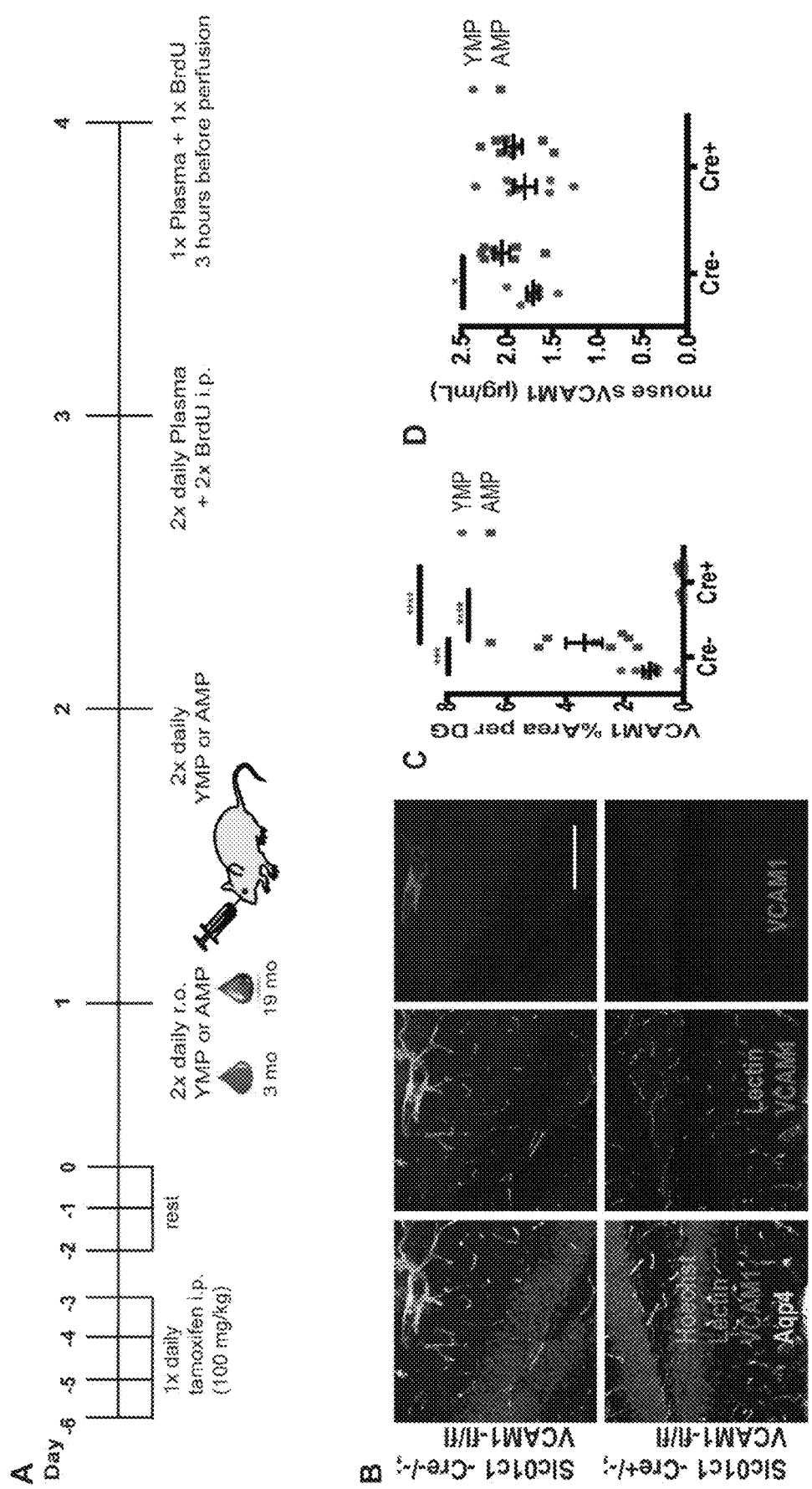
Figure 13:
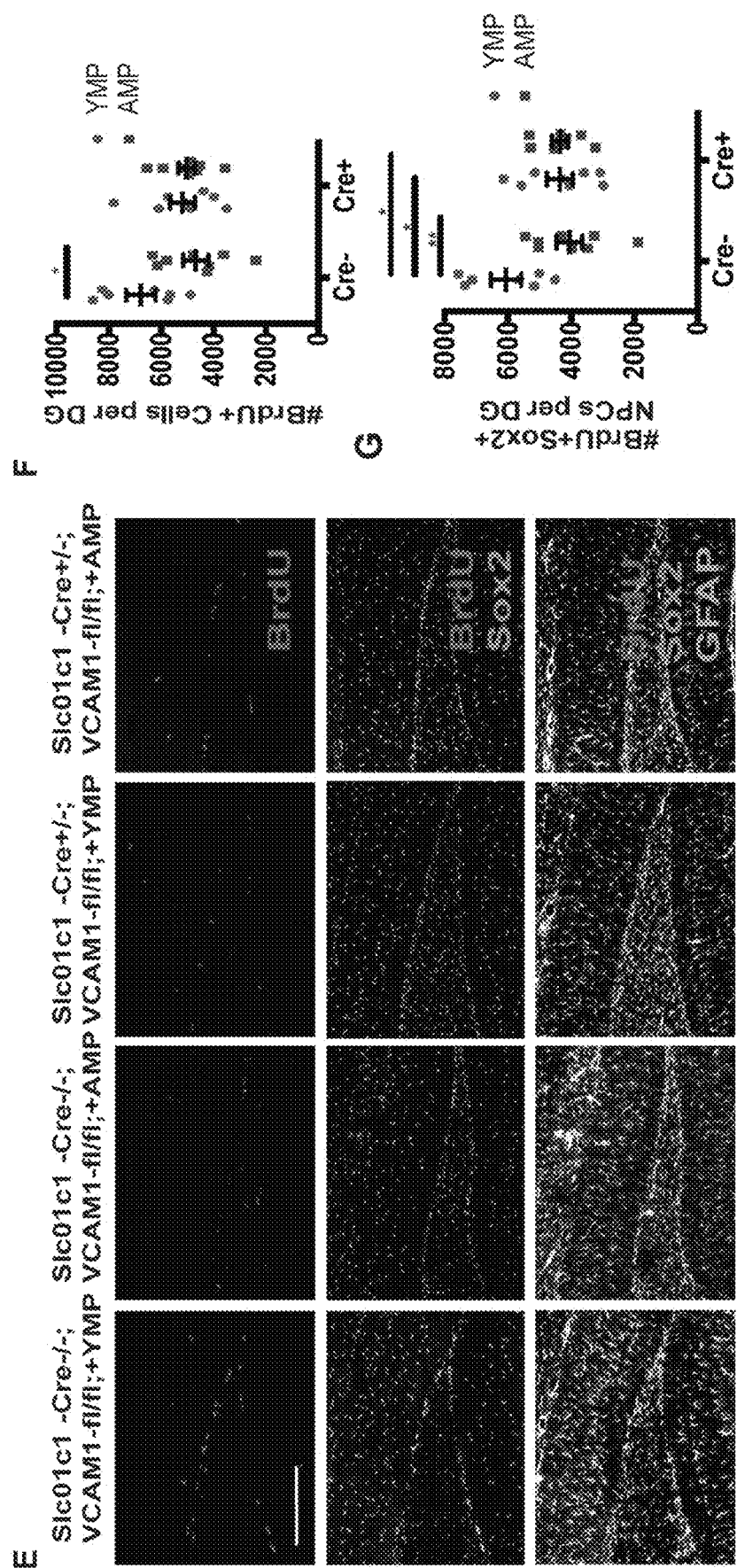
Figure 13:
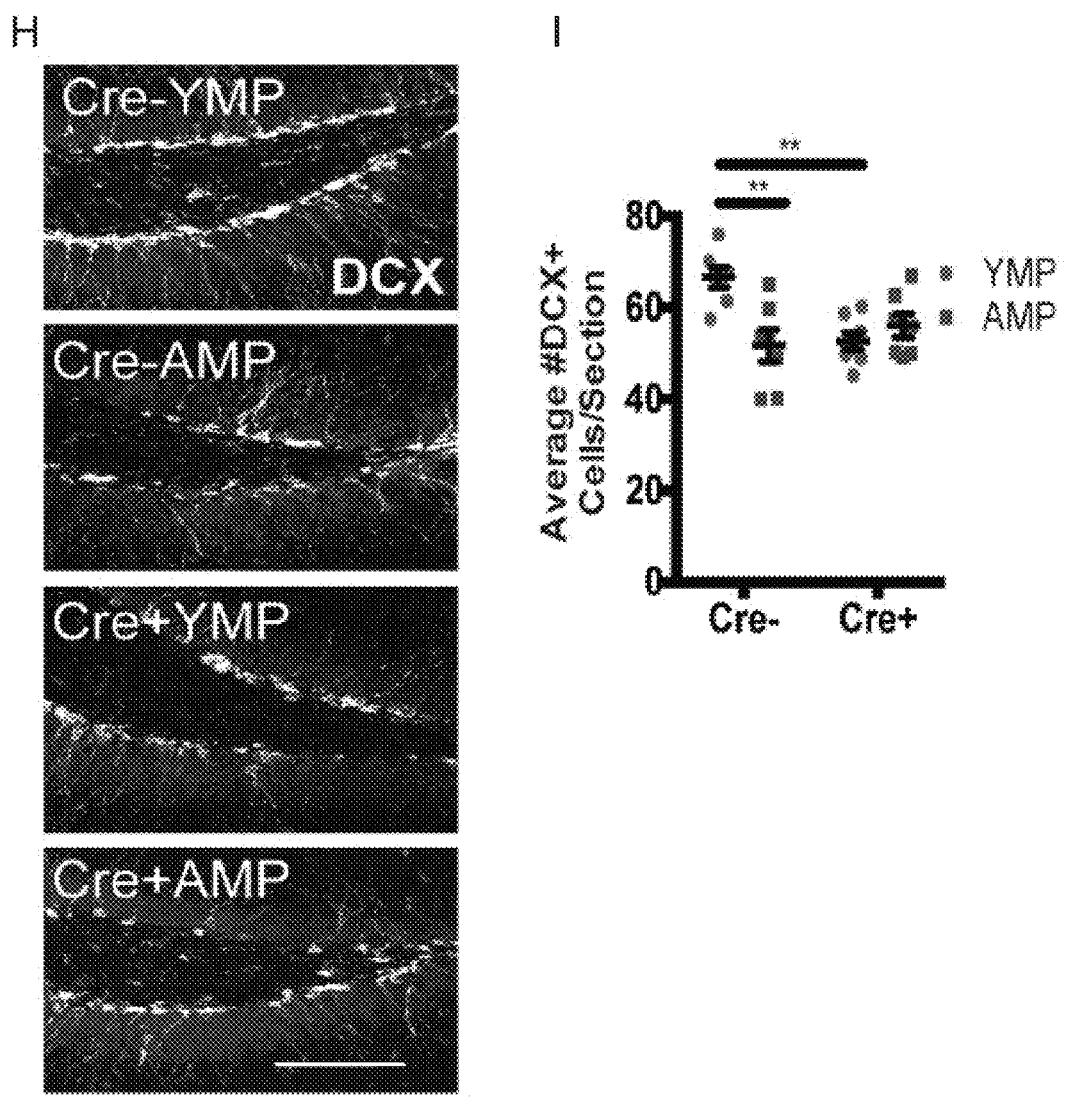
Figure 13:
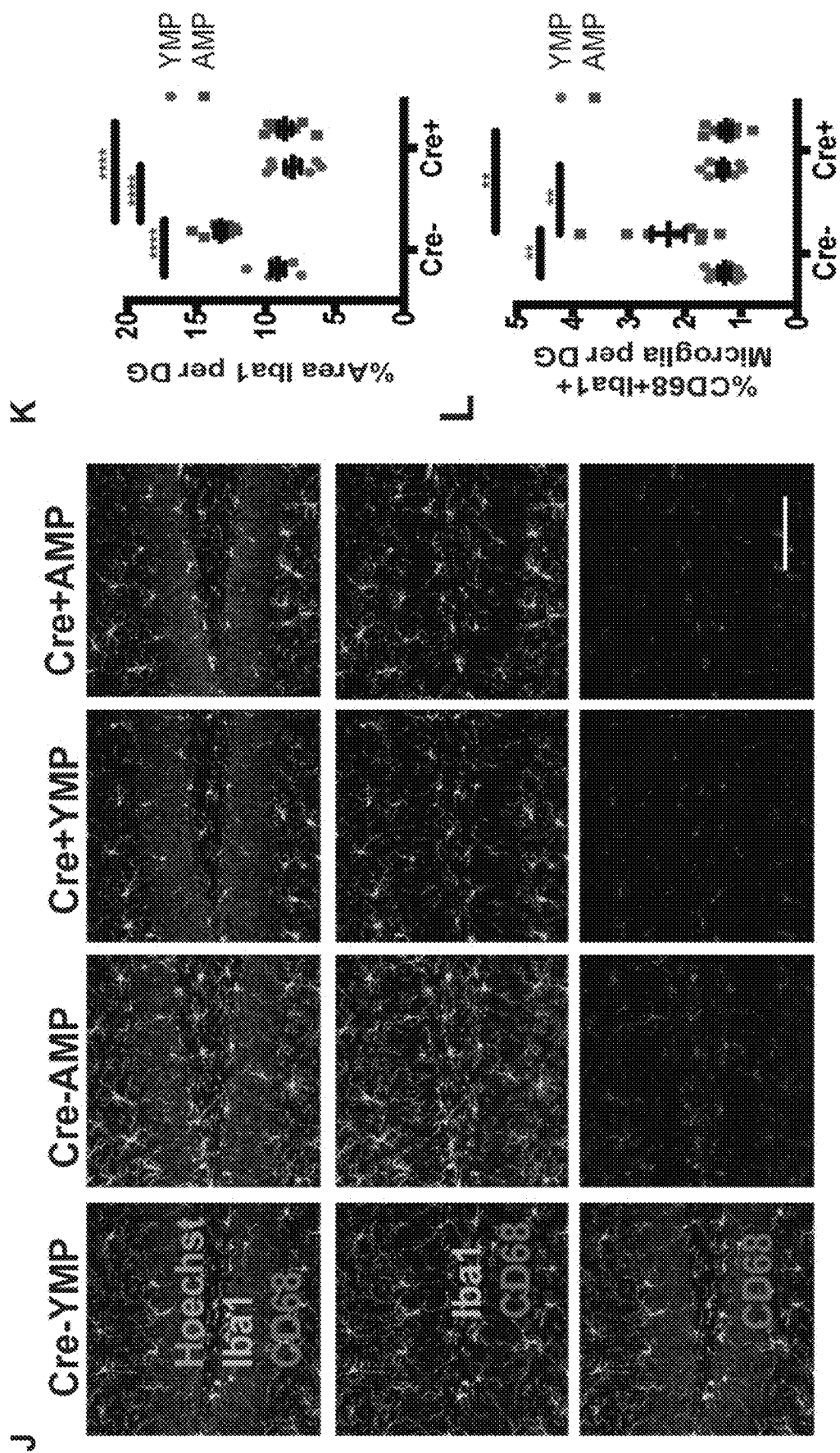

FIG. 13. Brain endothelial and epithelial-specific deletion of VCAM1 in young mice mitigates the negative effects of aged plasma administration on hippocampal neurogenesis and microglial reactivity. (A) Experimental Design. Young (3 month old) Vcam1$^{fl/fl}$ Slco1c1-Cre$^{ERT2+/-}$ mice (Cre+) were injected with tamoxifen (100 mg/kg i.p.) for 4 consecutive days, followed by 3 days of rest. Heterozygous littermates lacking Cre were also treated with tamoxifen (Cre- mice). Young or aged pooled mouse plasma (MP) (150 uL r.o.) was then administered for 4 days for 7 total injections, along with BrdU (100 mg/kg, i.p.) with the last 3 plasma injections. n=8 mice/group for 3 groups, with n=7 Vcam1$^{fl/fl}$ Slco1c1-Cre$^{ERT2-/-}$ mice (Cre-_. (B) Representative confocal images (5 sections/mouse) in the DG of VCAM1 (red), lectin (green), and Aqp4 (white). Hoechst (blue) labels cell nuclei. Scale bar=100 µm. Quantification in (C) demonstrates a three-fold increase in % area VCAM1+ Lectin+ brain vasculature in AMP treated mice in the Cre– cohort, while VCAM1 was absent in Cre+ mice. ****p<0.003. 2-way ANOVA with Tukeys post-hoc test. (D) A mouse sVCAM1 ELISA was performed on plasma of mice collected before perfusion. *p<0.03, 2-way ANOVA with Sidak's post-hoc test (E) Representative confocal images (6 sections/mouse) from the DG of brain sections immunostained for BrdU (red) to mark proliferating cells, colabeled with Sox2 (green) to label proliferating neural precursor cells and triple labeled with GFAP (white) to label activated neural stem cells; Scale bar=200 µm. Quantified in (F-G). *p<0.03, p<0.02. 2-way ANOVA with Tukey's post-hoc test. (H) Representative confocal immunofluorescence images (6 sections/mouse) in the DG of immunostained DCX (white). Hoechst (blue) labels cell nuclei. Scale bar=100 µm. Quantification of neurogenesis in (I) p<0.002, 2-way ANOVA with Tukey's post-hoc test. (J) Representative confocal images (of 5 sections/mouse) from the DG immunostained for CD68 (red), Iba1 (green), and hoechst (blue) to label cell nuclei. Scale bar=100 µm. Iba1+ % area staining quantified in (K) **p<0.0009, 2-way ANOVA with Tukey's post-hoc test. CD68+Iba1+ colocalized % area staining quantified in (L) p<0.007, 2-way ANOVA with Tukey's post-hoc test. All error bars represent SEM.

Figure 14:
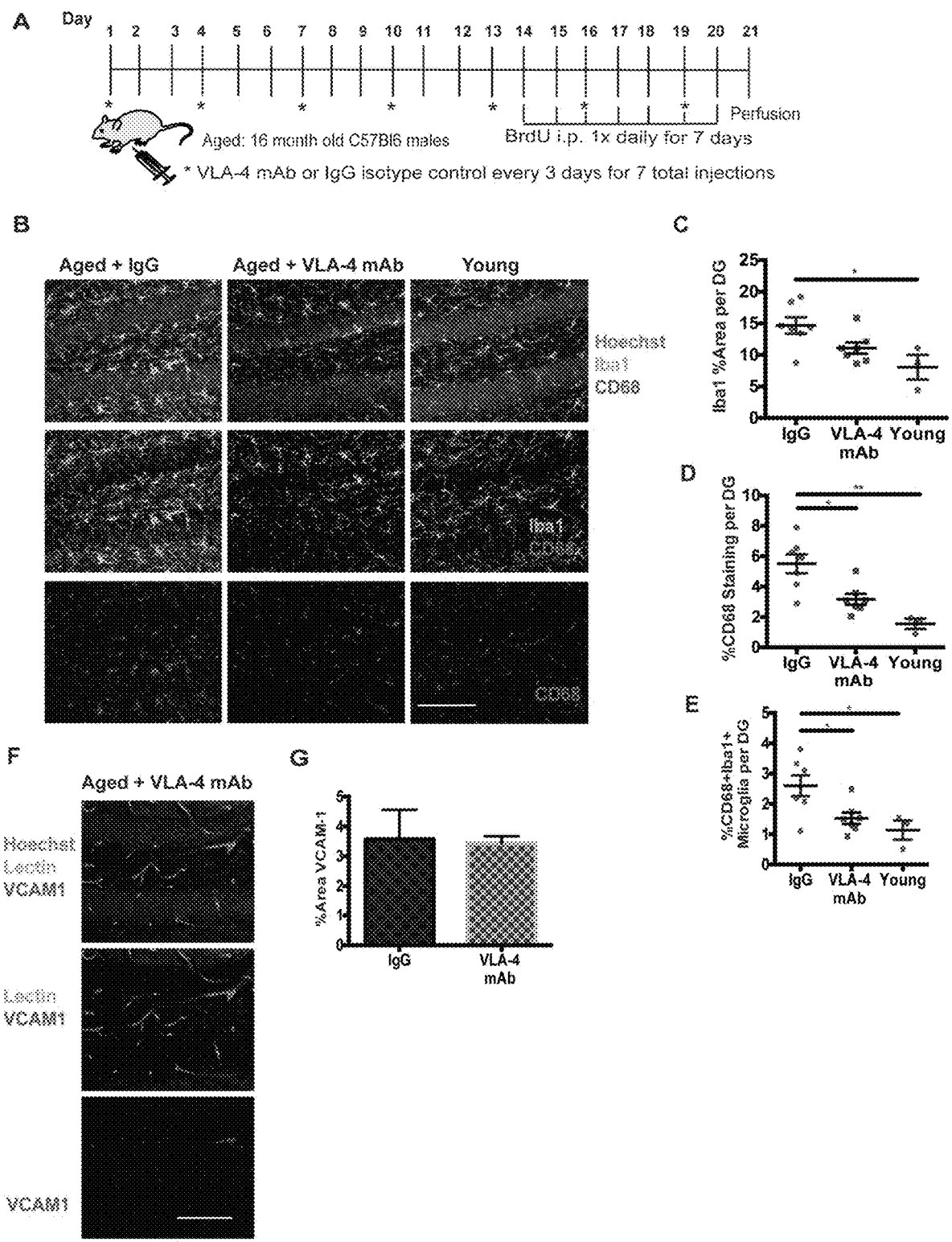

FIG. 14. Neutralizing monoclonal VLA-4 antibody reduces microglial reactivity in aged brains. (A) Experimental Setup. Aged (16 month old) mice received i.p. injections of monoclonal neutralizing antibody against mouse VLA-4 or rat IgG isotype control (9 mg/kg) every 3 days for 7 total injections. Mice also received BrdU daily (100 mg/kg i.p.) for the last 7 days prior to perfusion. n=7 mice/group. (B) Representative confocal images (of 7 sections per mouse) from the DG of aged mice which received VLA-4 mAb or IgG. Young brain sections (n=3 mice) are also represented to serve as a comparative assessment of the level of microglial rejuvenation. All sections were immunostained for CD68 (red), Iba1 (green), and hoechst (blue) to label cell nuclei. Scale bar=100 µm. Iba1+ % area staining quantified in (C) *p<0.02, CD68% area quantified in (D)**p<0.002, and CD68+Iba1+ colocalized % area staining quantified in (E) *p<0.02, ANOVA with Tukeys post-hoc test. (F) Representative immunofluorescence staining on one focal plane of a z-stack in the DG for VCAM1 (red), the endothelial marker Lectin (green), and hoechst (blue) to label cell nuclei. Scale bar=100 µm. Quantification in (G) of VCAM1+Lectin+ % area staining of thresholded images in 5, serial 40 um sections. Error bars represent SEM.

DETAILED DESCRIPTION

Methods of treating an adult mammal for an aging-associated impairment are provided. Aspects of the methods include reducing cell surface VCAM-1 activity in the mammal in a manner sufficient to treat the mammal for the aging-associated impairment. A variety of aging-associated impairments may be treated by practice of the methods, which impairments include cognitive impairments.

Before the present methods and compositions are described, it is to be understood that this invention is not limited to a particular method or composition described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

It must be noted that as used herein and in the appended claims, the singular forms "a", "an", and "the" include plural referents unless the context clearly dictates otherwise. Thus, for example, reference to "a cell" includes a plurality of such cells and reference to "the peptide" includes reference to one or more peptides and equivalents thereof, e.g., polypeptides, known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Methods

As summarized above, aspects of the invention include methods of treating an aging-associated impairment in an adult mammal. The aging-associated impairment may manifest in a number of different ways, e.g., as aging-associated cognitive impairment and/or physiological impairment, e.g., in the form of damage to central or peripheral organs of the body, such as but not limited to: cell injury, tissue damage, organ dysfunction, aging-associated lifespan shortening and carcinogenesis, where specific organs and tissues of interest include, but are not limited to skin, neuron, muscle, pancreas, brain, kidney, lung, stomach, intestine, spleen, heart, adipose tissue, testes, ovary, uterus, liver and bone; in the form of decreased neurogenesis, etc.

In some embodiments, the aging-associated impairment is an aging-associated impairment in cognitive ability in an individual, i.e., an aging-associated cognitive impairment. By cognitive ability, or "cognition", it is meant the mental processes that include attention and concentration, learning complex tasks and concepts, memory (acquiring, retaining, and retrieving new information in the short and/or long term), information processing (dealing with information gathered by the five senses), visuospatial function (visual perception, depth perception, using mental imagery, copying drawings, constructing objects or shapes), producing and understanding language, verbal fluency (word-finding), solving problems, making decisions, and executive functions (planning and prioritizing). By "cognitive decline", it is meant a progressive decrease in one or more of these abilities, e.g., a decline in memory, language, thinking, judgment, etc. By "an impairment in cognitive ability" and "cognitive impairment", it is meant a reduction in cognitive ability relative to a healthy individual, e.g., an age-matched healthy individual, or relative to the ability of the individual at an earlier point in time, e.g., 2 weeks, 1 month, 2 months, 3 months, 6 months, 1 year, 2 years, 5 years, or 10 years or more previously. Aging-associated cognitive impairments include impairments in cognitive ability that are typically associated with aging, including, for example, cognitive impairment associated with the natural aging process, e.g., mild cognitive impairment (M.C.I.); and cognitive impairment associated with an aging-associated disorder, that is, a disorder that is seen with increasing frequency with increasing senescence, e.g., as well as cognitive decline as a consequence of systemic inflammation, radiation, chemotherapy, frailty, kidney dysfunction, as well as neurodegenerative conditions such as Alzheimer's disease, Parkinson's disease, frontotemporal dementia, Huntington's disease, amyotrophic lateral sclerosis, multiple sclerosis, glaucoma, myotonic dystrophy, vascular dementia, and the like.

By "treatment" it is meant that at least an amelioration of one or more symptoms associated with an aging-associated impairment afflicting the adult mammal is achieved, where amelioration is used in a broad sense to refer to at least a reduction in the magnitude of a parameter, e.g., a symptom associated with the impairment being treated. As such, treatment also includes situations where a pathological condition, or at least symptoms associated therewith, are completely inhibited, e.g., prevented from happening, or stopped, e.g., terminated, such that the adult mammal no longer suffers from the impairment, or at least the symptoms that characterize the impairment. In some instances, "treatment", "treating" and the like refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment" may be any treatment of a disease in a mammal, and includes: (a) preventing the disease from occurring in a subject which may be predisposed to the disease but has not yet been diagnosed as having it; (b) inhibiting the disease, i.e., arresting its development; or (c) relieving the disease, i.e., causing regression of the disease. Treatment may result in a variety of different physical manifestations, e.g., modulation in gene expression, increased neurogenesis, rejuvenation of tissue or organs, etc. Treatment of ongoing disease, where the treatment stabilizes or reduces the undesirable clinical symptoms of the patient, occurs in some embodiments. Such treatment may be performed prior to complete loss of function in the affected tissues. The subject therapy may be administered during the symptomatic stage of the disease, and in some cases after the symptomatic stage of the disease.

In some instances where the aging-associated impairment is aging-associated cognitive decline, treatment by methods of the present disclosure slows, or reduces, the progression of aging-associated cognitive decline. In other words, cognitive abilities in the individual decline more slowly, if at all, following treatment by the disclosed methods than prior to or in the absence of treatment by the disclosed methods. In some instances, treatment by methods of the present disclosure stabilizes the cognitive abilities of an individual. For example, the progression of cognitive decline in an individual suffering from aging-associated cognitive decline is halted following treatment by the disclosed methods. As another example, cognitive decline in an individual, e.g., an individual 40 years old or older, that is projected to suffer from aging-associated cognitive decline, is prevented following treatment by the disclosed methods. In other words, no (further) cognitive impairment is observed. In some instances, treatment by methods of the present disclosure reduces, or reverses, cognitive impairment, e.g., as observed by improving cognitive abilities in an individual suffering from aging-associated cognitive decline. In other words, the cognitive abilities of the individual suffering from aging-associated cognitive decline following treatment by the disclosed methods are better than they were prior to treatment by the disclosed methods, i.e., they improve upon treatment. In some instances, treatment by methods of the present disclosure abrogates cognitive impairment. In other words, the cognitive abilities of the individual suffering from aging-associated cognitive decline are restored, e.g., to their level when the individual was about 40 years old or less, following treatment by the disclosed methods, e.g., as evidenced by improved cognitive abilities in an individual suffering from aging-associated cognitive decline.

In some instances, treatment of an adult mammal in accordance with the methods results in a change in a central organ, e.g., a central nervous system organ, such as the brain, spinal cord, etc., where the change may manifest in a number of different ways, e.g., as described in greater detail below, including but not limited to molecular, structural and/or functional, e.g., in the form of enhanced neurogenesis.

As summarized above, methods described herein are methods of treating an aging-associated impairment, e.g., as described above, in an adult mammal. By adult mammal is meant a mammal that has reached maturity, i.e., that is fully developed. As such, adult mammals are not juvenile. Mammalian species that may be treated with the present methods include canines and felines; equines; bovines; ovines; etc., and primates, including humans. The subject methods, compositions, and reagents may also be applied to animal models, including small mammals, e.g., murine, lagomorpha, etc., for example, in experimental investigations. The discussion below will focus on the application of the subject methods, compositions, reagents, devices and kits to humans, but it will be understood by the ordinarily skilled artisan that such descriptions can be readily modified to other mammals of interest based on the knowledge in the art.

The age of the adult mammal may vary, depending on the type of mammal that is being treated. Where the adult mammal is a human, the age of the human is generally 18 years or older. In some instances, the adult mammal is an individual suffering from or at risk of suffering from an aging-associated impairment, such as an aging-associated cognitive impairment, where the adult mammal may be one that has been determined, e.g., in the form of receiving a diagnosis, to be suffering from or at risk of suffering from an aging-associated impairment, such as an aging-associated cognitive impairment. The phrase "an individual suffering from or at risk of suffering from an aging-associated cognitive impairment" refers to an individual that is about 50 years old or older, e.g., 60 years old or older, 70 years old or older, 80 years old or older, and sometimes no older than 100 years old, such as 90 years old, i.e., between the ages of about 50 and 100, e.g., 50, 55, 60, 65, 70, 75, 80, 85 or about 90 years old. The individual may suffer from an aging associated condition, e.g., cognitive impairment, associated with the natural aging process, e.g., M.C.I. Alternatively, the individual may be 50 years old or older, e.g., 60 years old or older, 70 years old or older, 80 years old or older, 90 years old or older, and sometimes no older than 100 years old, i.e., between the ages of about 50 and 100, e.g., 50, 55, 60, 65, 70, 75, 80, 85, 90, 95 or about 100 years old, and has not yet begun to show symptoms of an aging associated condition, e.g., cognitive impairment. In yet other embodiments, the individual may be of any age where the individual is suffering from a cognitive impairment due to an aging-associated disease, e.g., Alzheimer's disease, Parkinson's disease, frontotemporal dementia, Huntington's disease, amyotrophic lateral sclerosis, multiple sclerosis, glaucoma, myotonic dystrophy, dementia, and the like. In some instances, the individual is an individual of any age that has been diagnosed with an aging-associated disease that is typically accompanied by cognitive impairment, e.g., Alzheimer's disease, Parkinson's disease, frontotemporal dementia, progressive supranuclear palsy, Huntington's disease, amyotrophic lateral sclerosis, spinal muscular atrophy, multiple sclerosis, multi-system atrophy, glaucoma, ataxias, myotonic dystrophy, dementia, and the like, where the individual has not yet begun to show symptoms of cognitive impairment.

As summarized above, aspects of the methods include reducing cell surface VCAM-1 activity in the mammal in a manner sufficient to treat the aging impairment in the mammal, e.g., as described above. By reducing cell surface VCAM-1 activity is meant diminishing the activity of cell surface VCAM-1 in the subject, e.g., by lowering the amount of surface VCAM-1 that is active in the mammal, by inhibiting the interaction of VCAM-1 with a receptor for which it is a ligand, etc. The target cell surface VCAM activity is activity of VCAM-1 that is present on a cell surface and mediates adhesion of leukocytes, e.g., one or more of lymphocytes, monocytes, eosinophils, and basophils. While the magnitude of the activity reduction may vary, in some instances the magnitude is 2-fold or greater, such as 5-fold or greater, including 10-fold or greater, e.g., 15-fold or greater, 20-fold or greater, 25-fold or greater (as compared to a suitable control). In those instances where the activity is reduced by lowering the amount of surface VCAM-1 that is active in the mammal, the magnitude may be such that the amount of detectable active VCAM-1 on cells of a target tissue is 50% or less, such as 25% or less, including 10% or less, e.g., 1% or less, relative to the amount that was detectable prior to intervention according to the invention, and in some instances the amount is undetectable following intervention.

In some instances, the target cell surface VCAM-1 is an endothelial cell surface VCAM-1, e.g., a blood vessel endothelial cell surface VCAM-1. In some instances, the blood vessel endothelial cell surface VCAM-1 is a brain cell surface VCAM-1, e.g., a cebrovascular endothelial cell surface VCAM-1, such as hippocampus endothelial cell surface VCAM-1.

The cell surface VCAM-1 activity may be reduced using any convenient protocol. In some instances, the cell surface VCAM-1 activity is reduced by administering to the mammal an effective amount of cell surface VCAM-1 activity reducing agent. As such, in practicing methods according to these embodiments of the invention, an effective amount of the active agent, e.g., cell surface VCAM-1 modulatory agent, VCAM-1 receptor modulatory agent, etc., is provided to the adult mammal.

Depending on the particular embodiments being practiced, a variety of different types of active agents may be employed. In some embodiments, the agent is an agent that modulates, e.g., inhibits, target cell surface VCAM-1 activity by binding to VCAM-1. In certain embodiments, the administered active agent is a VCAM-1 specific binding member. In general, useful VCAM-1 specific binding members exhibit an affinity (Kd) for a target VCAM-1, such as human VCAM-1, that is sufficient to provide for the desired reduction in aging associated impairment VCAM-1 activity. As used herein, the term "affinity" refers to the equilibrium constant for the reversible binding of two agents; "affinity" can be expressed as a dissociation constant (Kd). Affinity can be at least 1-fold greater, at least 2-fold greater, at least 3-fold greater, at least 4-fold greater, at least 5-fold greater, at least 6-fold greater, at least 7-fold greater, at least 8-fold greater, at least 9-fold greater, at least 10-fold greater, at least 20-fold greater, at least 30-fold greater, at least 40-fold greater, at least 50-fold greater, at least 60-fold greater, at least 70-fold greater, at least 80-fold greater, at least 90-fold greater, at least 100-fold greater, or at least 1000-fold greater, or more, than the affinity of an antibody for unrelated amino acid sequences. Affinity of a specific binding member to a target protein can be, for example, from about 100 nanomolar (nM) to about 0.1 nM, from about 100 nM to about 1 picomolar (pM), or from about 100 nM to about 1 femtomolar (fM) or more. The term "binding" refers to a direct association between two molecules, due to, for example, covalent, electrostatic, hydrophobic, and ionic and/or hydrogen-bond interactions, including interactions such as salt bridges and water bridges. In some embodiments, the antibodies bind human VCAM-1 with nanomolar affinity or picomolar affinity. In some embodiments, the antibodies bind human VCAM-1 with a Kd of less than about 100 nM, 50 nM, 20 nM, 20 nM, or 1 nM. In some embodiments, the affinity between the binding member active agent in a binding complex with VCAM-1 is characterized by a $K_d$ (dissociation constant) of $10^{-6}$ M or less, such as $10^{-7}$ M or less, including $10^{-8}$ M or less, e.g., $10^{-9}$ M or less, $10^{-10}$ M or less, $10^{-11}$ M or less, $10^{-12}$ M or less, $10^{-13}$ M or less, $10^{-14}$ M or less, including $10^{-15}$ M or less.

Examples of VCAM-1 specific binding members include VCAM-1 antibodies and binding fragments thereof. Non-limiting examples of such antibodies include antibodies directed against any epitope of VCAM-1. Also encompassed are bispecific antibodies, i.e., antibodies in which each of the two binding domains recognizes a different binding epitope. The amino acid sequence of canonical human VCAM-1 is provided at the website address produced by placing "http://www." before "uniprot.org/uniprot/P19320" as:

```
                                          (SEQ ID NO: 01)
MPGKMVVILG ASNILWIMFA ASQAFKIETT PESRYLAQIG

DSVSLTCSTT GCESPFFSWR TQIDSPLNGK VTNEGTTSTL

TMNPVSFGNE HSYLCTATCE SRKLEKGIQV EIYSFPKDPE

IHLSGPLEAG KPITVKCSVA DVYPFDRLEI DLLKGDHLMK

SQEFLEDADR KSLETKSLEV TFTPVIEDIG KVLVCRAKLH
```

-continued
```
IDEMDSVPTV RQAVKELQVY ISPKNTVISV NPSTKLQEGG

SVTMTCSSEG LPAPEIFWSK KLDNGNLQHL SGNATLTLIA

MRMEDSGIYV CEGVNLIGKN RKEVELIVQE KPFTVEISPG

PRIAAQIGDS VMLTCSVMGC ESPSFSWRTQ IDSPLSGKVR

SEGTNSTLTL SPVSFENEHS YLCTVTCGHK KLEKGIQVEL

YSFPRDPEIE MSGGLVNGSS VTVSCKVPSV YPLDRLEIEL

LKGETILENI EFLEDTDMKS LENKSLEMTF IPTIEDTGKA

LVCQAKLHID DMEFEPKQRQ STQTLYVNVA PRDTTVLVSP

SSILEEGSSV NMTCLSQGFP APKILWSRQL PNGELQPLSE

NATLTLISTK MEDSGVYLCE GINQAGRSRK EVELIIQVTP

KDIKLTAFPS ESVKEGDTVI ISCTCGNVPE TWIILKKKAE

TGDTVLKSID GAYTIRKAQL KDAGVYECES KNKVGSQLRS

LTLDVQGREN NKDYFSPELL VLYFASSLII PAIGMIIYFA

RKANMKGSYS LVEAQKSKV
```

Antibody specific binding members that may be employed include full antibodies or immunoglobulins of any isotype, as well as fragments of antibodies which retain specific binding to antigen, including, but not limited to, Fab, Fv, scFv, and Fd fragments, chimeric antibodies, humanized antibodies, single-chain antibodies, and fusion proteins comprising an antigen-binding portion of an antibody and a non-antibody protein. The antibodies may be detectably labeled, e.g., with a radioisotope, an enzyme which generates a detectable product, a fluorescent protein, and the like. The antibodies may be further conjugated to other moieties, such as members of specific binding pairs, e.g., biotin (member of biotin-avidin specific binding pair), and the like. Also encompassed by the term are Fab', Fv, F(ab')2, and or other antibody fragments that retain specific binding to antigen, and monoclonal antibodies. An antibody may be monovalent or bivalent.

"Antibody fragments" comprise a portion of an intact antibody, for example, the antigen binding or variable region of the intact antibody. Examples of antibody fragments include Fab, Fab', F(ab')2, and Fv fragments; diabodies; linear antibodies (Zapata et al., Protein Eng. 8(10): 1057-1062 (1995)); single-chain antibody molecules; and multispecific antibodies formed from antibody fragments. Papain digestion of antibodies produces two identical antigen-binding fragments, called "Fab" fragments, each with a single antigen-binding site, and a residual "Fc" fragment, a designation reflecting the ability to crystallize readily. Pepsin treatment yields an F(ab')2 fragment that has two antigen combining sites and is still capable of cross-linking antigen.

"Fv" is the minimum antibody fragment which contains a complete antigen-recognition and -binding site. This region consists of a dimer of one heavy- and one light-chain variable domain in tight, non-covalent association. It is in this configuration that the three CDRS of each variable domain interact to define an antigen-binding site on the surface of the VH-VL dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The "Fab" fragment also contains the constant domain of the light chain and the first constant domain (CH1) of the heavy chain. Fab fragments differ from Fab' fragments by the addition of a few residues at the carboxyl terminus of the heavy chain CH1 domain including one or more cysteines from the antibody hinge region. Fab'-SH is the designation herein for Fab' in which the cysteine residue(s) of the constant domains bear a free thiol group. F(ab')2 antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa and lambda, based on the amino acid sequences of their constant domains. Depending on the amino acid sequence of the constant domain of their heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA, and IgA2.

"Single-chain Fv" or "sFv" antibody fragments comprise the VH and VL domains of antibody, wherein these domains are present in a single polypeptide chain. In some embodiments, the Fv polypeptide further comprises a polypeptide linker between the VH and VL domains, which enables the sFv to form the desired structure for antigen binding. For a review of sFv, see Pluckthun in The Pharmacology of Monoclonal Antibodies, vol. 113, Rosenburg and Moore eds., Springer-Verlag, New York, pp. 269-315 (1994).

Antibodies that may be used in connection with the present disclosure thus can encompass monoclonal antibodies, polyclonal antibodies, bispecific antibodies, Fab antibody fragments, F(ab)2 antibody fragments, Fv antibody fragments (e.g., VH or VL), single chain Fv antibody fragments and dsFv antibody fragments. Furthermore, the antibody molecules may be fully human antibodies, humanized antibodies, or chimeric antibodies. In some embodiments, the antibody molecules are monoclonal, fully human antibodies.

The antibodies that may be used in connection with the present disclosure can include any antibody variable region, mature or unprocessed, linked to any immunoglobulin constant region. If a light chain variable region is linked to a constant region, it can be a kappa chain constant region. If a heavy chain variable region is linked to a constant region, it can be a human gamma 1, gamma 2, gamma 3 or gamma 4 constant region, more preferably, gamma 1, gamma 2 or gamma 4 and even more preferably gamma 1 or gamma 4.

In some embodiments, fully human monoclonal antibodies directed against VCAM-1 are generated using transgenic mice carrying parts of the human immune system rather than the mouse system.

Minor variations in the amino acid sequences of antibodies or immunoglobulin molecules are encompassed by the present invention, providing that the variations in the amino acid sequence maintain at least 75%, e.g., at least 80%, 90%, 95%, or 99% of the sequence. In particular, conservative amino acid replacements are contemplated. Conservative replacements are those that take place within a family of amino acids that are related in their side chains. Whether an amino acid change results in a functional peptide can readily be determined by assaying the specific activity of the polypeptide derivative. Fragments (or analogs) of antibodies or immunoglobulin molecules, can be readily prepared by those of ordinary skill in the art. Preferred amino- and carboxy-termini of fragments or analogs occur near boundaries of functional domains. Structural and functional domains can be identified by comparison of the nucleotide and/or amino acid sequence data to public or proprietary sequence databases. Preferably, computerized comparison methods are used to identify sequence motifs or predicted protein conformation domains that occur in other proteins of known structure and/or function. Methods to identify protein sequences that fold into a known three-dimensional structure are known. Sequence motifs and structural conformations may be used to define structural and functional domains in accordance with the invention.

Specific examples of antibody agents that may be employed to reduce cell surface active VCAM-1 include, but are not limited to, those described in U.S. Pat. Nos. 6,123, 915; 7,655,417; 8,623,368 and 8,715,670; the disclosures of which are herein incorporated by reference.

VCAM-1 specific binding members also include non-antibody binding members. For example, small molecules that bind to the VCAM-1 and inhibit its activity are of interest. Naturally occurring or synthetic small molecule compounds of interest include numerous chemical classes, such as organic molecules, e.g., small organic compounds having a molecular weight of more than 50 and less than about 2,500 daltons. Candidate agents comprise functional groups for structural interaction with proteins, particularly hydrogen bonding, and typically include at least an amine, carbonyl, hydroxyl or carboxyl group, preferably at least two of the functional chemical groups. The candidate agents may include cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. Such molecules may be identified, among other ways, by employing the screening protocols described below.

Specific examples of small molecule agents that may be employed to reduce cell surface active VCAM-1 include, but are not limited to: those compounds described in: U.S. Pat. Nos. 6,229,011; 6,087,330; 5,837,478 and 5,510,332; the disclosures of which are herein incorporated by reference.

Agents finding use in the methods of the invention also include agents that modulate expression of the RNA and/or protein from the gene, such that it changes the expression of the RNA or protein from the target gene in some manner. In these instances, the agent may change expression of the RNA or protein in a number of different ways. In certain embodiments, the agent is one that reduces, including inhibits, expression of a VCAM-1 protein. Inhibition of VCAM-1 protein expression may be accomplished using any convenient protocol, including use of an agent that inhibits VCAM-1 protein expression, such as, but not limited to: RNAi agents, antisense agents, agents that interfere with a transcription factor binding to a promoter sequence of the VCAM-1 gene, or inactivation of the VCAM-1 gene, e.g., through recombinant techniques, etc.

For example, the transcription level of a VCAM-1 protein can be regulated by gene silencing using RNAi agents, e.g., double-strand RNA (see e.g., Sharp, Genes and Development (1999) 13: 139-141). RNAi, such as double-stranded RNA interference (dsRNAi) or small interfering RNA (siRNA), has been extensively documented in the nematode *C. elegans* (Fire, et al, Nature (1998) 391:806-811) and routinely used to "knock down" genes in various systems. RNAi agents may be dsRNA or a transcriptional template of the interfering ribonucleic acid which can be used to produce dsRNA in a cell. In these embodiments, the transcriptional template may be a DNA that encodes the interfering ribonucleic acid. Methods and procedures associated with RNAi are also described in published PCT Application Publication Nos. WO 03/010180 and WO 01/68836, the disclosures of which applications are incorporated herein by reference. dsRNA can be prepared according to any of a number of methods that are known in the art, including in vitro and in vivo methods, as well as by synthetic chemistry approaches. Examples of such methods include, but are not limited to, the methods described by Sadher et al., Biochem. Int. (1987) 14:1015; Bhattacharyya, Nature (1990) 343:484; and U.S. Pat. No. 5,795,715, the disclosures of which are incorporated herein by reference. Single-stranded RNA can also be produced using a combination of enzymatic and organic synthesis or by total organic synthesis. The use of synthetic chemical methods enable one to introduce desired modified nucleotides or nucleotide analogs into the dsRNA. dsRNA can also be prepared in vivo according to a number of established methods (see, e.g., Sambrook, et al. (1989) Molecular Cloning: A Laboratory Manual, 2nd ed.; Transcription and Translation (B. D. Hames, and S. J. Higgins, Eds., 1984); DNA Cloning, volumes I and II (D. N. Glover, Ed., 1985); and Oligonucleotide Synthesis (M. J. Gait, Ed., 1984, each of which is incorporated herein by reference). A number of options can be utilized to deliver the dsRNA into a cell or population of cells such as in a cell culture, tissue, organ or embryo. For instance, RNA can be directly introduced intracellularly. Various physical methods are generally utilized in such instances, such as administration by microinjection (see, e.g., Zernicka-Goetz, et al. Development (1997)124:1133-1137; and Wianny, et al., Chromosoma (1998) 107: 430-439). Other options for cellular delivery include permeabilizing the cell membrane and electroporation in the presence of the dsRNA, liposome-mediated transfection, or transfection using chemicals such as calcium phosphate. A number of established gene therapy techniques can also be utilized to introduce the dsRNA into a cell. By introducing a viral construct within a viral particle, for instance, one can achieve efficient introduction of an expression construct into the cell and transcription of the RNA encoded by the construct. Specific examples of RNAi agents that may be employed to reduce VCAM-1 expression include, but are not limited to, those described in: Petersen et al., "siRNA silencing reveals role of vascular cell adhesion molecule-1 in vascular smooth muscle cell migration," Atherosclerosis (2008) 198(2): 301-306 and Qu et al., "VCAM-1 siRNA reduces neointimal formation after surgical mechanical injury of the rat carotid artery," J Vasc Surg. (2009) 50(6):1452-8.

In some instances, antisense molecules can be used to down-regulate expression of a VCAM-1 gene in the cell. The anti-sense reagent may be antisense oligodeoxynucleotides (ODN), particularly synthetic ODN having chemical modifications from native nucleic acids, or nucleic acid constructs that express such anti-sense molecules as RNA. The antisense sequence is complementary to the mRNA of the targeted protein, and inhibits expression of the targeted protein. Antisense molecules inhibit gene expression through various mechanisms, e.g., by reducing the amount of mRNA available for translation, through activation of RNAse H, or steric hindrance. One or a combination of antisense molecules may be administered, where a combination may include multiple different sequences.

Antisense molecules may be produced by expression of all or a part of the target gene sequence in an appropriate vector, where the transcriptional initiation is oriented such that an antisense strand is produced as an RNA molecule. Alternatively, the antisense molecule is a synthetic oligonucleotide. Antisense oligonucleotides will generally be at least about 7, usually at least about 12, more usually at least about 20 nucleotides in length, and not more than about 500, usually not more than about 50, more usually not more than about 35 nucleotides in length, where the length is governed by efficiency of inhibition, specificity, including absence of cross-reactivity, and the like. Short oligonucleotides, of from 7 to 8 bases in length, can be strong and selective inhibitors of gene expression (see Wagner et al., Nature Biotechnol. (1996)14:840-844).

A specific region or regions of the endogenous sense strand mRNA sequence are chosen to be complemented by the antisense sequence. Selection of a specific sequence for the oligonucleotide may use an empirical method, where several candidate sequences are assayed for inhibition of expression of the target gene in an in vitro or animal model. A combination of sequences may also be used, where several regions of the mRNA sequence are selected for antisense complementation.

Antisense oligonucleotides may be chemically synthesized by methods known in the art (see Wagner et al. (1993), supra.) Oligonucleotides may be chemically modified from the native phosphodiester structure, in order to increase their intracellular stability and binding affinity. A number of such modifications have been described in the literature, which alter the chemistry of the backbone, sugars or heterocyclic bases. Among useful changes in the backbone chemistry are phosphorothioates; phosphorodithioates, where both of the non-bridging oxygens are substituted with sulfur; phosphoroamidites; alkyl phosphotriesters and boranophosphates. Achiral phosphate derivatives include 3'-O-5'-S-phosphorothioate, 3'-S-5'-O-phosphorothioate, 3'-CH.sub.2-5'-O-phosphonate and 3'-NH-5'-O-phosphoroamidate. Peptide nucleic acids replace the entire ribose phosphodiester backbone with a peptide linkage. Sugar modifications are also used to enhance stability and affinity. The α-anomer of deoxyribose may be used, where the base is inverted with respect to the natural β-anomer. The 2'-OH of the ribose sugar may be altered to form 2'-O-methyl or 2'-O-allyl sugars, which provides resistance to degradation without comprising affinity. Modification of the heterocyclic bases must maintain proper base pairing. Some useful substitutions include deoxyuridine for deoxythymidine; 5-methyl-2'-deoxycytidine and 5-bromo-2'-deoxycytidine for deoxycytidine. 5-propynyl-2'-deoxyuridine and 5-propynyl-2'-deoxycytidine have been shown to increase affinity and biological activity when substituted for deoxythymidine and deoxycytidine, respectively. Specific examples of antisense agents that may be employed to reduce VCAM-1 expression include, but are not limited to, those described in U.S. Pat. No. 5,596,090; the disclosure of which is herein incorporated by reference.

As an alternative to anti-sense inhibitors, catalytic nucleic acid compounds, e.g. ribozymes, anti-sense conjugates, etc. may be used to inhibit gene expression. Ribozymes may be synthesized in vitro and administered to the patient, or may be encoded on an expression vector, from which the ribozyme is synthesized in the targeted cell (for example, see International patent application WO 9523225, and Beigelman et al. Nucl. Acids Res. (1995) 23:4434-42). Examples of oligonucleotides with catalytic activity are described in WO 9506764. Conjugates of anti-sense ODN with a metal complex, e.g. terpyridylCu(II), capable of mediating mRNA hydrolysis are described in Bashkin et al. Appl. Biochem. Biotechnol. (1995) 54:43-56.

In another embodiment, the VCAM-1 gene is inactivated so that it no longer expresses a functional protein. By inactivated is meant that the gene, e.g., coding sequence and/or regulatory elements thereof, is genetically modified so that it no longer expresses a functional VCAM-1 protein, e.g., at least with respect to VCAM-1 aging impairment activity. The alteration or mutation may take a number of different forms, e.g., through deletion of one or more nucleotide residues, through exchange of one or more nucleotide residues, and the like. One means of making such alterations in the coding sequence is by homologous recombination. Methods for generating targeted gene modifications through homologous recombination are known in the art, including those described in: U.S. Pat. Nos. 6,074,853; 5,998,209; 5,998,144; 5,948,653; 5,925,544; 5,830,698; 5,780,296; 5,776,744; 5,721,367; 5,614,396; 5,612,205; the disclosures of which are herein incorporated by reference.

Also of interest in certain embodiments are dominant negative mutants of VCAM-1 proteins, where expression of such mutants in the cell result in a modulation, e.g., decrease, in VCAM-1 mediated aging impairment. Dominant negative mutants of VCAM-1 are mutant proteins that exhibit dominant negative VCAM-1 activity. As used herein, the term "dominant-negative VCAM-1 activity" or "dominant negative activity" refers to the inhibition, negation, or diminution of certain particular activities of VCAM-1, and specifically to VCAM-1 mediated aging impairment. Dominant negative mutations are readily generated for corresponding proteins. These may act by several different mechanisms, including mutations in a substrate-binding domain; mutations in a catalytic domain; mutations in a protein binding domain (e.g., multimer forming, effector, or activating protein binding domains); mutations in cellular localization domain, etc. A mutant polypeptide may interact with wild-type polypeptides (made from the other allele) and form a non-functional multimer. In certain embodiments, the mutant polypeptide will be overproduced. Point mutations are made that have such an effect. In addition, fusion of different polypeptides of various lengths to the terminus of a protein, or deletion of specific domains can yield dominant negative mutants. General strategies are available for making dominant negative mutants (see for example, Herskowitz, Nature (1987) 329:219, and the references cited above). Such techniques are used to create loss of function mutations, which are useful for determining protein function. Methods that are well known to those skilled in the art can be used to construct expression vectors containing coding sequences and appropriate transcriptional and translational control signals for increased expression of an exogenous gene introduced into a cell. These methods include, for example, in vitro recombinant DNA techniques, synthetic techniques, and in vivo genetic recombination. Alternatively, RNA capable of encoding gene product sequences may be chemically synthesized using, for example, synthesizers. See, for example, the techniques described in "Oligonucleotide Synthesis", 1984, Gait, M. J. ed., IRL Press, Oxford.

VCAM-1 expression modulatory, e.g., inhibitory agents, that may be employed in embodiments of the methods further include, but are not limited to, those described in U.S. Pat. Nos. 6,147,250; 6,548,699; 6,602,914; 6,608,101; 6,617,352; 6,828,447; 6,852,878; 7,078,431; 7,189,870; 7,375,252; and 7,622,256; the disclosures of which are herein incorporated by reference.

Another type of active cell surface VCAM-1 reducing agent that may be employed in embodiments of the invention is a VCAM-1 shedding promoting agent. VCAM-1 shedding promoting agents are agents that enhance production of the soluble form of VCAM-1, e.g., via cleavage of membrane bound VCAM-1, such as cleavage near a transmembrane domain of VCAM-1.

In some instances, the agent is an agent that enhances tumor necrosis factor-alpha-converting enzyme (TACE) (i.e., ADAM 17) activity. By enhancing an ADAM17 activity is meant increasing ADAM17 activity in the subject. In some instances, the ADAM17 activity that is enhanced is ADAM17 activity present in cells that exhibit the target VCAM-1, e.g., as described above. The magnitude of the increase may vary, where in some instances the magnitude of the increase is 2-fold or greater, such as 5-fold or greater, including 10-fold or greater, e.g., 15-fold or greater, 20-fold or greater, 25-fold or greater (as compared to a suitable control). The ADAM17 activity that is increased by practice of the methods is an ADAM17 activity that is beneficial in treating an aging associated condition. In other words, the ADAM17 activity that is enhanced is one that results in treatment, e.g., as described above, of the subject for the aging associated condition.

The target ADAM17 activity that is enhanced may vary. Of interest are mammalian ADAM17 proteins, such as but not limited to: primate, e.g., human, canine, feline, equine, bovine, ovine, murine, lagomorpha, etc. The sequence of human ADAM-17 reported in Black et al., Nature (1997) 385: 729-733 and is reported at website having an address produced by placing "http://www." before "uniprot.org/uniprot/P78536" as:

```
                                      (SEQ ID NO: 02)
MRQSLLFLTS  VVPFVLAPRP  PDDPGFGPHQ  RLEKLDSLLS

DYDILSLSNI  QQHSVRKRDL  QTSTHVETLL  TFSALKRHFK

LYLTSSTERF  SQNFKVVVVD  GKNESEYTVK  WQDFFTGHVV

GEPDSRVLAH  IRDDDVIIRI  NTDGAEYNIE  PLWRFVNDTK

DKRMLVYKSE  DIKNVSRLQS  PKVCGYLKVD  NEELLPKGLV

DREPPEELVH  RVKRRADPDP  MKNTCKLLVV  ADHRFYRYMG

RGEESTTTNY  LIELIDRVDD  IYRNTSWDNA  GFKGYGIQIE

QIRILKSPQE  VKPGEKHYNM  AKSYPNEEKD  AWDVKMLLEQ

FSFDIAEEAS  KVCLAHLFTY  QDFDMGTLGL  AYVGSPRANS

HGGVCPKAYY  SPVGKKNIYL  NSGLTSTKNY  GKTILTKEAD

LVTTHELGHN  FGAEHDPDGL  AECAPNEDQG  GKYVMYPIAV

SGDHENNKMF  SNCSKQSIYK  TIESKAQECF  QERSNKVCGN

SRVDEGEECD  PGIMYLNNDT  CCNSDCTLKE  GVQCSDRNSP

CCKNCQFETA  QKKCQEAINA  TCKGVSYCTG  NSSECPPPGN

AEDDTVCLDL  GKCKDGKCIP  FCEREQQLES  CACNETDNSC

KVCCRDLSGR  CVPYVDAEQK  NLFLRKGKPC  TVGFCDMNGK

CEKRVQDVIE  RFWDFIDQLS  INTFGKFLAD  NIVGSVLVFS

LIFWIPFSIL  VHCVDKKLDK  QYESLSLFHP  SNVEMLSSMD

SASVRIIKPF  PAPQTPGRLQ  PAPVIPSAPA  APKLDHQRMD

TIQEDPSTDS  HMDEDGFEKD  PFPNSSTAAK  SFEDLTDHPV

TRSEKAASFK  LQRQNRVDSK  ETEC
```

The target ADAM17 activity may be enhanced using any convenient protocol. In some instances, the target ADAM17 activity is enhanced by increasing a target cellular level of an ADAM17 active agent in the mammal. The magnitude of the increase may vary, where in some instances the magnitude of the increase is 2-fold or greater, such as 5-fold or greater, including 10-fold or greater, e.g., 15-fold or greater, 20-fold or greater, 25-fold or greater (as compared to a suitable control). In these embodiments, the target level of the ADAM17 active agent of interest may be increased using any convenient protocol. ADAM-17 active agent may vary and include ADAM17 polypeptides and nucleic acids encoding the same.

ADAM17 polypeptides are polypeptides that, upon administration to a subject, exhibit the desired treatment activity, e.g., as described above. The term "polypeptide" as used herein refers to full-length proteins as well as portions or fragments thereof which exhibit the desired ADAM17 activity. Also included in this term are variations of the naturally occurring proteins, where such variations are homologous or substantially similar to the naturally occurring protein, as described in greater detail below, be the naturally occurring protein the human protein, mouse protein, or protein from some other species which naturally expresses an ADAM17 protein. In the following description, the term ADAM17 is used to refer not only to the human form of an ADAM17 protein, but also to homologs thereof expressed in non-human species.

ADAM17 polypeptides of interest may vary in terms of amino acid sequence length and molecular weight. In some instances, the ADAM17 polypeptides range in length from 175 to 350, such as from 200 to 250 and including from about 200 to 225 amino acid residues, and have a projected molecular weight based solely on the number of amino acid residues in the protein and assuming an average molecular weight of 110 Daltons that ranges from 19 to 39 kDa, such as 22 to 28 kDa, including 22 to 25 kDa, where the actual molecular weight may vary depending on the amount of glycosylation of the protein and the apparent molecular weight may be considerably less because of SDS binding on gels. ADAM17 polypeptides as described herein may be obtained from naturally sources, e.g., via purification techniques, chemically synthesized or produced using recombinant protocols, as desired.

In some instances, the ADAM17 polypeptide that is administered to the subject is a human ADAM17 protein, where the human ADAM17 protein has an amino acid sequence that comprises a region substantially the same as or identical to the sequence appearing above. By substantially the same as is meant a protein having a region with a sequence that is 60% or greater, such as 75% or greater, such as 90% or greater and including 98% or greater sequence identity with the sequence appearing above, as determined by BLAST using default settings.

In addition to the specific ADAM17 proteins described above, homologs or proteins (or fragments thereof) from other species, e.g., other animal species, may also be employed in embodiments of the methods, where such homologs or proteins may be from a variety of different types of species, including animals, such as mammals, e.g., rodents, such as mice, rats; domestic animals, e.g., horse, cow, dog, cat; etc. By homolog is meant a protein having 35% or more, such as 40% and more and including 60% or more amino acid sequence identity to the specific ADAM17 proteins provided above, where sequence identity is determined using BLAST at default settings.

In addition to the naturally occurring ADAM17 proteins, e.g., as described above, ADAM17 polypeptides that vary from the naturally occurring ADAM17 proteins may also be employed in practicing methods of the invention. Different variations may be present, including but not limited to substitution, insertion and/or deletion mutations, as well as other types of non-amino acid sequence variations, e.g., as illustrated below. ADAM17 polypeptides that may be employed include proteins having an amino acid sequence encoded by an open reading frame (ORF) of an ADAM17 gene, including the full length ADAM17 protein and fragments thereof, such as biologically active fragments and/or fragments corresponding to functional domains; and including fusions of the subject polypeptides to other proteins or parts thereof. Fragments of interest may vary in length, and in some instances are 10 aa or longer, such as 50 aa or longer, and including 100 aa or longer, and in some instances do not exceed 150 aa in length, where a given fragment will have a stretch of amino acids that is substantially the same as or identical to a subsequence found in the sequence provided above; where the subsequence may vary in length and in some instances is 10 aa or longer, such as 15 aa or longer, up to 50 aa or even longer.

In some instances, ADAM17 polypeptides employed in methods of invention include one or more modifications. Modifications that may be present may vary, and include but are not limited to: amide bond substitutions, amino acid substitutions, including of cysteine residues/analogues, cyclization, pegylation, etc. Examples of modifications that may be found in ADAM17 polypeptides employed in methods of the invention are now reviewed in greater detail.

In some cases, ADAM17 polypeptides include one or more linkages other than peptide bonds, e.g., at least two adjacent amino acids are joined via a linkage other than an amide bond. For example, in order to reduce or eliminate undesired proteolysis or other means of degradation, and/or to increase serum stability, and/or to restrict or increase conformational flexibility, one or more amide bonds within the backbone of an ADAM17 polypeptide can be substituted. In another example, one or more amide linkages (—CO—NH—) in an ADAM17 polypeptide can be replaced with a linkage which is an isostere of an amide linkage, such as —CH$_2$NH—, —CH$_2$S—, —CH$_2$CH$_2$—, —CH=CH-(cis and trans), —COCH$_2$—, —CH(OH)CH$_2$— or —CH$_2$SO—. One or more amide linkages in an ADAM17 polypeptide can also be replaced by, for example, a reduced isostere pseudopeptide bond.

One or more amino acid substitutions can be made in an ADAM17 polypeptide. The following are non-limiting examples: a) substitution of alkyl-substituted hydrophobic amino acids, including alanine, leucine, isoleucine, valine, norleucine, (S)-2-aminobutyric acid, (S)-cyclohexylalanine or other simple alpha-amino acids substituted by an aliphatic side chain from $C_1$-$C_{10}$ carbons including branched, cyclic and straight chain alkyl, alkenyl or alkynyl substitutions; b) substitution of aromatic-substituted hydrophobic amino acids, including phenylalanine, tryptophan, tyrosine, sulfotyrosine, biphenylalanine, 1-naphthylalanine, 2-naphthylalanine, 2-benzothienylalanine, 3-benzothienylalanine, histidine, including amino, alkylamino, dialkylamino, aza, halogenated (fluoro, chloro, bromo, or iodo) or alkoxy (from $C_1$-$C_4$)-substituted forms of the above-listed aromatic amino acids, illustrative examples of which are: 2-, 3- or 4-aminophenylalanine, 2-, 3- or 4-chlorophenylalanine, 2-, 3- or 4-methylphenylalanine, 2-, 3- or 4-methoxyphenylalanine, 5-amino-, 5-chloro-, 5-methyl- or 5-methoxytryptophan, 2'-, 3'-, or 4'-amino-, 2'-, 3'-, or 4'-chloro-, 2, 3, or 4-biphenylalanine, 2'-, 3'-, or 4'-methyl-, 2-, 3- or 4-biphenylalanine, and 2- or 3-pyridylalanine; c) substitution of amino acids containing basic side chains, including arginine, lysine, histidine, ornithine, 2,3-diaminopropionic acid, homoarginine, including alkyl, alkenyl, or aryl-substituted (from $C_1$-$C_{10}$ branched, linear, or cyclic) derivatives of the previous amino acids, whether the substituent is on the heteroatoms (such as the alpha nitrogen, or the distal nitrogen or nitrogens, or on the alpha carbon, in the pro-R position for example. Compounds that serve as illustrative examples include: N-epsilon-isopropyl-lysine, 3-(4-tetrahydropyridyl)-glycine, 3-(4-tetrahydropyridyl)-alanine, N,N-gamma, gamma'-diethyl-homoarginine. Included also are compounds such as alpha-methyl-arginine, alpha-methyl-2,3-diaminopropionic acid, alpha-methyl-histidine, alpha-methyl-ornithine where the alkyl group occupies the pro-R position of the alpha-carbon. Also included are the amides formed from alkyl, aromatic, heteroaromatic (where the heteroaromatic group has one or more nitrogens, oxygens or sulfur atoms singly or in combination), carboxylic acids or any of the many well-known activated derivatives such as acid chlorides, active esters, active azolides and related derivatives, and lysine, ornithine, or 2,3-diaminopropionic acid; d) substitution of acidic amino acids, including aspartic acid, glutamic acid, homoglutamic acid, tyrosine, alkyl, aryl, arylalkyl, and heteroaryl sulfonamides of 2,4-diaminopriopionic acid, ornithine or lysine and tetrazole-substituted alkyl amino acids; e) substitution of side chain amide residues, including asparagine, glutamine, and alkyl or aromatic substituted derivatives of asparagine or glutamine; and f) substitution of hydroxyl-containing amino acids, including serine, threonine, homoserine, 2,3-diaminopropionic acid, and alkyl or aromatic substituted derivatives of serine or threonine.

In some cases, an ADAM17 polypeptide includes one or more naturally occurring non-genetically encoded L-amino acids, synthetic L-amino acids, or D-enantiomers of an amino acid. For example, an ADAM17 polypeptide can include only D-amino acids. For example, an ADAM17 polypeptide can include one or more of the following residues: hydroxyproline, β-alanine, o-aminobenzoic acid, m-aminobenzoic acid, p-aminobenzoic acid, m-aminomethylbenzoic acid, 2,3-diaminopropionic acid, α-aminoisobutyric acid, N-methylglycine (sarcosine), ornithine, citrulline, t-butylalanine, t-butylglycine, N-methylisoleucine, phenylglycine, cyclohexylalanine, norleucine, naphthylalanine, pyridylalanine 3-benzothienyl alanine, 4-chlorophenylalanine, 2-fluorophenylalanine, 3-fluorophenylalanine, 4-fluorophenylalanine, penicillamine, 1,2,3,4-tetrahydroisoquinoline-3-carboxylic acid, β-2-thienylalanine, methionine sulfoxide, homoarginine, N-acetyl lysine, 2,4-diamino butyric acid, rho-aminophenylalanine, N-methylvaline, homocysteine, homoserine, ε-amino hexanoic acid, ω-aminohexanoic acid, ω-aminoheptanoic acid, ω-aminooctanoic acid, ω-aminodecanoic acid, ω-aminotetradecanoic acid, cyclohexylalanine, α,γ-diaminobutyric acid, α,β-diaminopropionic acid, δ-amino valeric acid, and 2,3-diaminobutyric acid.

A cysteine residue or a cysteine analog can be introduced into an ADAM17 polypeptide to provide for linkage to another peptide via a disulfide linkage or to provide for cyclization of the ADAM17 polypeptide. An ADAM17 polypeptide can be cyclized. One or more cysteines or cysteine analogs can be introduced into an ADAM17 polypeptide, where the introduced cysteine or cysteine analog can form a disulfide bond with a second introduced cysteine or cysteine analog. Other means of cyclization include introduction of an oxime linker or a lanthionine linker; see, e.g., U.S. Pat. No. 8,044,175. Any combination of amino acids (or non-amino acid moieties) that can form a cyclizing bond can be used and/or introduced. A cyclizing bond can be generated with any combination of amino acids (or with an amino acid and —(CH2)$_n$-CO— or —(CH2)$_n$-$C_6H_4$—CO—) with functional groups which allow for the introduction of a bridge. Some examples are disulfides, disulfide mimetics such as the —(CH2)$_n$— carba bridge, thioacetal, thioether bridges (cystathionine or lanthionine) and bridges containing esters and ethers. In these examples, n can be any integer, but is frequently less than ten.

Other modifications include, for example, an N-alkyl (or aryl) substitution (ψ[CONR]), or backbone crosslinking to construct lactams and other cyclic structures. Other derivatives include C-terminal hydroxymethyl derivatives, o-modified derivatives (e.g., C-terminal hydroxymethyl benzyl ether), N-terminally modified derivatives including substituted amides such as alkylamides and hydrazides.

Modifications may be present that provide for improvements in one or more physical properties of the ADAM17 polypeptide. Improvements of physical properties include, for example, modulating immunogenicity; methods of increasing water solubility, bioavailability, serum half-life, and/or therapeutic half-life; and/or modulating biological activity. Examples of such modifications include, but are not limited to: pegylation, glycosylation (N- and O-linked); polysialylation; albumin fusion molecules comprising serum albumin (e.g., human serum albumin (HSA), cyno serum albumin, or bovine serum albumin (BSA)); albumin binding through, for example a conjugated fatty acid chain (acylation); and Fc-fusion proteins.

Pegylation:

The clinical effectiveness of protein therapeutics may be limited by short plasma half-life and susceptibility to protease degradation. Studies of various therapeutic proteins (e.g., filgrastim) have shown that such difficulties may be overcome by various modifications, including conjugating or linking the polypeptide sequence to any of a variety of nonproteinaceous polymers, e.g., polyethylene glycol (PEG), polypropylene glycol, or polyoxyalkylenes. This is frequently effected by a linking moiety covalently bound to both the protein and the nonproteinaceous polymer, e.g., a PEG. Such PEG-conjugated biomolecules have been shown to possess clinically useful properties, including better physical and thermal stability, protection against susceptibility to enzymatic degradation, increased solubility, longer in vivo circulating half-life and decreased clearance, reduced immunogenicity and antigenicity, and reduced toxicity. In addition to the beneficial effects of pegylation on pharmacokinetic parameters, pegylation itself may enhance activity. PEGs suitable for conjugation to a polypeptide sequence are generally soluble in water at room temperature, and have the general formula R(O—$CH_2$—$CH_2$)$_n$O—R, where R is hydrogen or a protective group such as an alkyl or an alkanol group, and where n is an integer from 1 to 1000. When R is a protective group, it generally has from 1 to 8 carbons. The PEG conjugated to the polypeptide sequence can be linear or branched. Branched PEG derivatives, "star-PEGs" and multi-armed PEGs are contemplated by the present disclosure. A molecular weight of the PEG used in the present disclosure is not restricted to any particular range, and examples are set forth elsewhere herein; by way of example, certain embodiments have molecular weights between 5 kDa and 20 kDa, while other embodiments have molecular weights between 4 kDa and 10 kDa. Pegylated ADAM17 polypeptides may be conjugates wherein the PEGs have different n values, and thus the various different PEGs are present in specific ratios. For example, some compositions comprise a mixture of conjugates where n=1, 2, 3 and 4. In some compositions, the percentage of conjugates where n=1 is 18-25%, the percentage of conjugates where n=2 is 50-66%, the percentage of conjugates where n=3 is 12-16%, and the percentage of conjugates where n=4 is up to 5%. Such compositions can be produced by any convenient reaction conditions and purification. Pegylation most frequently occurs at the alpha amino group at the N-terminus of the polypeptide, the epsilon amino group on the side chain of lysine residues, and the imidazole group on the side chain of histidine residues. Since most recombinant polypeptides possess a single alpha and a number of epsilon amino and imidazole groups, numerous positional isomers can be generated depending on the linker chemistry. General pegylation strategies, such as those known in the art, can be applied herein. PEG may be bound to a polypeptide of the present disclosure via a terminal reactive group (a "spacer") which mediates a bond between the free amino or carboxyl groups of one or more of the polypeptide sequences and polyethylene glycol. The PEG having the spacer which may be bound to the free amino group includes N-hydroxysuccinylimide polyethylene glycol which may be prepared by activating succinic acid ester of polyethylene glycol with N-hydroxysuccinylimide. Another activated polyethylene glycol which may be bound to a free amino group is 2,4-bis(O-methoxypolyethyleneglycol)-6-chloro-s-triazine, which may be prepared by reacting polyethylene glycol monomethyl ether with cyanuric chloride. The activated polyethylene glycol which is bound to the free carboxyl group includes polyoxyethylenediamine. Conjugation of one or more of the polypeptide sequences to PEG having a spacer may be carried out by various conventional methods. For example, the conjugation reaction can be carried out in solution at a pH of from 5 to 10, at temperature from 4° C. to room temperature, for 30 minutes to 20 hours, utilizing a molar ratio of reagent to protein of from 4:1 to 30:1. Reaction conditions may be selected to direct the reaction towards producing predominantly a desired degree of substitution. In general, low temperature, low pH (e.g., pH=5), and short reaction time tend to decrease the number of PEGs attached, whereas high temperature, neutral to high pH (e.g., pH≥17), and longer reaction time tend to increase the number of PEGs attached. Various means known in the art may be used to terminate the reaction. In some embodiments the reaction is terminated by acidifying the reaction mixture and freezing at, e.g., −20° C. Pegylation of various molecules is discussed in, for example, U.S. Pat. Nos. 5,252,714; 5,643,575; 5,919,455; 5,932,462; and 5,985,263. The present disclosure also contemplates the use of PEG mimetics. Recombinant PEG mimetics have been developed that retain the attributes of PEG (e.g., enhanced serum half-life) while conferring several additional advantageous properties. By way of example, simple polypeptide chains (comprising, for example, Ala, Glu, Gly, Pro, Ser and Thr) capable of forming an extended conformation similar to PEG can be produced recombinantly already fused to the peptide or protein drug of interest. This obviates the need for an additional conjugation step during the manufacturing process. Moreover, established molecular biology techniques enable control of the side chain composition of the polypeptide chains, allowing optimization of immunogenicity and manufacturing properties.

Glycosylation:

For purposes of the present disclosure, "glycosylation" is meant to broadly refer to the enzymatic process that attaches glycans to proteins, lipids or other organic molecules. The use of the term "glycosylation" in conjunction with the present disclosure is generally intended to mean adding or deleting one or more carbohydrate moieties (either by removing the underlying glycosylation site or by deleting the glycosylation by chemical and/or enzymatic means), and/or adding one or more glycosylation sites that may or may not be present in the native sequence. In addition, the phrase includes qualitative changes in the glycosylation of the native proteins involving a change in the nature and proportions of the various carbohydrate moieties present. Glycosylation can dramatically affect the physical properties (e.g., solubility) of polypeptides such as ADAM17 polypeptides and can also be important in protein stability, secretion, and subcellular localization. Glycosylated polypeptides may also exhibit enhanced stability or may improve one or more pharmacokinetic properties, such as half-life. In addition, solubility improvements can, for example, enable the generation of formulations more suitable for pharmaceutical administration than formulations comprising the non-glycosylated polypeptide. Addition of glycosylation sites can be accomplished by altering the amino acid sequence. The alteration to the polypeptide may be made, for example, by the addition of, or substitution by, one or more serine or threonine residues (for O-linked glycosylation sites) or asparagine residues (for N-linked glycosylation sites). The structures of N-linked and O-linked oligosaccharides and the sugar residues found in each type may be different. One type of sugar that is commonly found on both is N-acetylneuraminic acid (hereafter referred to as sialic acid). Sialic acid is usually the terminal residue of both N-linked and O-linked oligosaccharides and, by virtue of its negative charge, may confer acidic properties to the glycoprotein. A particular embodiment of the present disclosure comprises the generation and use of N-glycosylation variants. The polypeptide sequences of the present disclosure may optionally be altered through changes at the nucleic acid level, particularly by mutating the nucleic acid encoding the polypeptide at preselected bases such that codons are generated that will translate into the desired amino acids. Another means of increasing the number of carbohydrate moieties on the polypeptide is by chemical or enzymatic coupling of glycosides to the polypeptide. Removal of carbohydrates may be accomplished chemically or enzymatically, or by substitution of codons encoding amino acid residues that are glycosylated. Chemical deglycosylation techniques are known, and enzymatic cleavage of carbohydrate moieties on polypeptides can be achieved by the use of a variety of endo- and exo-glycosidases. Dihydrofolate reductase (DHFR)—deficient Chinese Hamster Ovary (CHO) cells are a commonly used host cell for the production of recombinant glycoproteins. These cells do not express the enzyme beta-galactoside alpha-2,6-sialyltransferase and therefore do not add sialic acid in the alpha-2,6 linkage to N-linked oligosaccharides of glycoproteins produced in these cells.

In some embodiments, the polypeptides are non-naturally glycosylated. By non-naturally glycosylated is meant that the polypeptide has a glycosylation pattern, if present, which is not the same as the glycosylation pattern found in the corresponding naturally occurring protein. For example, a human ADAM17 employed in methods of the invention of this particular embodiment is characterized by having a glycosylation pattern, if glycosylated at all, that differs from that of naturally occurring human ADAM17. Thus, the non-naturally glycosylated ADAM17 polypeptides of this embodiment include non-glycosylated ADAM17 polypeptides, i.e. proteins having no covalently bound glycosyl groups.

Polysialylation:

The present disclosure also contemplates the use of polysialylation, the conjugation of polypeptides to the naturally occurring, biodegradable α-(2→8) linked polysialic acid ("PSA") in order to improve the polypeptides' stability and in vivo pharmacokinetics. PSA is a biodegradable, non-toxic natural polymer that is highly hydrophilic, giving it a high apparent molecular weight in the blood which increases its serum half-life. In addition, polysialylation of a range of peptide and protein therapeutics has led to markedly reduced proteolysis, retention of in vivo activity, and reduction in immunogenicity and antigenicity (see, e.g., G. Gregoriadis et al., Int. J. Pharmaceutics 300(1-2):125-30). As with modifications with other conjugates (e.g., PEG), various techniques for site-specific polysialylation are available (see, e.g., T. Lindhout et al., (2011) PNAS 108(18)7397-7402).

Albumin Fusion:

Additional suitable components and molecules for conjugation include albumins such as human serum albumin (HSA), cyno serum albumin, and bovine serum albumin (BSA). Mature HSA, a 585 amino acid polypeptide (~67 kDa) having a serum half-life of ~20 days, is primarily responsible for the maintenance of colloidal osmotic blood pressure, blood pH, and transport and distribution of numerous endogenous and exogenous ligands. The protein has three structurally homologous domains (domains I, II and III), is almost entirely in the alpha-helical conformation, and is highly stabilized by 17 disulphide bridges. The three primary drug binding regions of albumin are located on each of the three domains within sub-domains IB, IIA and IIIA. Albumin synthesis takes place in the liver, which produces the short-lived, primary product preproalbumin. Thus, the full-length HSA has a signal peptide of 18 amino acids (MKWVTFISLLFLFSSAYS) followed by a pro-domain of 6 amino acids (RGVFRR); this 24 amino acid residue peptide may be referred to as the pre-pro domain. HSA can be expressed and secreted using its endogenous signal peptide as a pre-pro-domain. Alternatively, HSA can be expressed and secreted using a IgK signal peptide fused to a mature construct. Preproalbumin is rapidly co-translationally cleaved in the endoplasmic reticulum lumen at its amino terminus to produce the stable, 609-amino acid precursor polypeptide, proalbumin. Proalbumin then passes to the Golgi apparatus, where it is converted to the 585 amino acid mature albumin by a furin-dependent amino-terminal cleavage. The primary amino acid sequences, structure, and function of albumins are highly conserved across species, as are the processes of albumin synthesis and secretion. Albumin serum proteins comparable to HSA are found in, for example, cynomolgus monkeys, cows, dogs, rabbits and rats. Of the non-human species, bovine serum albumin (BSA) is the most structurally similar to HSA (see, e.g., Kosa et al., November 2007 J Pharm Sci. 96(11):3117-24). The present disclosure contemplates the use of albumin from non-human species, including, but not limited to, those set forth above, in, for example, the drug development process. According to the present disclosure, albumin may be conjugated to a drug molecule (e.g., a polypeptide described herein) at the carboxyl terminus, the amino terminus, both the carboxyl and amino termini, and internally (see, e.g., U.S. Pat. Nos. 5,876,969 and 7,056,701). In the HSA-ADAM17 conjugates contemplated by the present disclosure, various forms of albumin may be used, such as albumin secretion pre-sequences and variants thereof, fragments and variants thereof, and HSA variants. Such forms generally possess one or more desired albumin activities. In additional embodiments, the present disclosure involves fusion proteins comprising a polypeptide drug molecule fused directly or indirectly to albumin, an albumin fragment, and albumin variant, etc., wherein the fusion protein has a higher plasma stability than the unfused drug molecule and/or the fusion protein retains the therapeutic activity of the unfused drug molecule. In some embodiments, the indirect fusion is effected by a linker, such as a peptide linker or modified version thereof. Intracellular cleavage may be carried out enzymatically by, for example, furin or caspase. Cells express a low level of these endogenous enzymes, which are capable of cleaving a portion of the fusion molecules intracellularly; thus, some of the polypeptides are secreted from the cell without being conjugated to HSA, while some of the polypeptides are secreted in the form of fusion molecules that comprise HSA. Embodiments of the present disclosure contemplate the use of various furin fusion constructs. For example, constructs may be designed that comprise the sequence RGRR, RKRKKR, RKKR, or RRRKKR. The present disclosure also contemplates extracellular cleavage (i.e., ex-vivo cleavage) whereby the fusion molecules are secreted from the cell, subjected to purification, and then cleaved. It is understood that the excision may dissociate the entire HSA-linker complex from the mature ADAM17 polypeptide, or less that the entire HSA-linker complex. As alluded to above, fusion of albumin to one or more polypeptides of the present disclosure can, for example, be achieved by genetic manipulation, such that the nucleic acid coding for HSA, or a fragment thereof, is joined to the nucleic acid coding for the one or more polypeptide sequences. Thereafter, a suitable host can be transformed or transfected with the fused nucleotide sequences in the form of, for example, a suitable plasmid, so as to express a fusion polypeptide. The expression may be effected in vitro from, for example, prokaryotic or eukaryotic cells, or in vivo from, for example, a transgenic organism. In some embodiments of the present disclosure, the expression of the fusion protein is performed in mammalian cell lines, for example, CHO cell lines. Transformation is used broadly herein to refer to the genetic alteration of a cell resulting from the direct uptake through the cell membrane, incorporation and expression of exogenous genetic material (exogenous nucleic acid). Transformation occurs naturally in some species of bacteria, but it can also be effected by artificial means in other cells. Furthermore, albumin itself may be modified to extend its circulating half-life. Fusion of the modified albumin to an ADAM17 polypeptide can be attained by the genetic manipulation techniques described above or by chemical conjugation; the resulting fusion molecule has a half-life that exceeds that of fusions with non-modified albumin.

Conjugation with Other Molecules:

Additional suitable components and molecules for conjugation include, for example, thyroglobulin; tetanus toxoid; Diphtheria toxoid; polyamino acids such as poly(D-lysine: D-glutamic acid); VP6 polypeptides of rotaviruses; influenza virus hemaglutinin, influenza virus nucleoprotein; Keyhole Limpet Hemocyanin (KLH); and hepatitis B virus core protein and surface antigen; or any combination of the foregoing. Thus, the present disclosure contemplates conjugation of one or more additional components or molecules at the N- and/or C-terminus of a polypeptide sequence, such as another polypeptide (e.g., a polypeptide having an amino acid sequence heterologous to the subject polypeptide), or a carrier molecule. Thus, an exemplary polypeptide sequence can be provided as a conjugate with another component or molecule. A conjugate modification may result in a polypeptide sequence that retains activity with an additional or complementary function or activity derived from the second molecule. For example, a polypeptide sequence may be conjugated to a molecule, e.g., to facilitate solubility, storage, in vivo or shelf half-life or stability, reduction in immunogenicity, delayed or controlled release in vivo, etc. Other functions or activities include a conjugate that reduces toxicity relative to an unconjugated polypeptide sequence, a conjugate that targets a type of cell or organ more efficiently than an unconjugated polypeptide sequence, or a drug to further counter the causes or effects associated with a disease, disorder or condition as set forth herein (e.g., cancer). An ADAM17 polypeptide may also be conjugated to large, slowly metabolized macromolecules such as proteins; polysaccharides, such as sepharose, agarose, cellulose, or cellulose beads; polymeric amino acids such as polyglutamic acid, or polylysine; amino acid copolymers; inactivated virus particles; inactivated bacterial toxins such as toxoid from diphtheria, tetanus, cholera, or leukotoxin molecules; inactivated bacteria; and dendritic cells. Such conjugated forms, if desired, can be used to produce antibodies against a polypeptide of the present disclosure. Additional candidate components and molecules for conjugation include those suitable for isolation or purification. Particular non-limiting examples include binding molecules, such as biotin (biotin-avidin specific binding pair), an antibody, a receptor, a ligand, a lectin, or molecules that comprise a solid support, including, for example, plastic or polystyrene beads, plates or beads, magnetic beads, test strips, and membranes. Purification methods such as cation exchange chromatography may be used to separate conjugates by charge difference, which effectively separates conjugates into their various molecular weights. For example, the cation exchange column can be loaded and then washed with ~20 mM sodium acetate, pH ~4, and then eluted with a linear (0 M to 0.5 M) NaCl gradient buffered at a pH from about 3 to 5.5, e.g., at pH ~4.5. The content of the fractions obtained by cation exchange chromatography may be identified by molecular weight using conventional methods, for example, mass spectroscopy, SDS-PAGE, or other known methods for separating molecular entities by molecular weight.

Fc-Fusion Molecules:

In certain embodiments, the amino- or carboxyl-terminus of a polypeptide sequence of the present disclosure can be fused with an immunoglobulin Fc region (e.g., human Fc) to form a fusion conjugate (or fusion molecule). Fc fusion conjugates have been shown to increase the systemic half-life of biopharmaceuticals, and thus the biopharmaceutical product may require less frequent administration. Fc binds to the neonatal Fc receptor (FcRn) in endothelial cells that line the blood vessels, and, upon binding, the Fc fusion molecule is protected from degradation and re-released into the circulation, keeping the molecule in circulation longer. This Fc binding is believed to be the mechanism by which endogenous IgG retains its long plasma half-life. More recent Fc-fusion technology links a single copy of a biopharmaceutical to the Fc region of an antibody to optimize the pharmacokinetic and pharmacodynamic properties of the biopharmaceutical as compared to traditional Fc-fusion conjugates.

Other Modifications:

The present disclosure contemplates the use of other modifications, currently known or developed in the future, of ADAM17 polypeptides to improve one or more properties. One such method for prolonging the circulation half-life, increasing the stability, reducing the clearance, or altering the immunogenicity or allergenicity of a polypeptide of the present disclosure involves modification of the polypeptide sequences by hesylation, which utilizes hydroxyethyl starch derivatives linked to other molecules in order to modify the polypeptide sequences' characteristics.

Linkers:

Linkers and their use have been described above. Any of the foregoing components and molecules used to modify the polypeptide sequences of the present disclosure may optionally be conjugated via a linker. Suitable linkers include "flexible linkers" which are generally of sufficient length to permit some movement between the modified polypeptide sequences and the linked components and molecules. The linker molecules are generally about 6-50 atoms long. The linker molecules may also be, for example, aryl acetylene, ethylene glycol oligomers containing 2-10 monomer units, diamines, diacids, amino acids, or combinations thereof. Suitable linkers can be readily selected and can be of any suitable length, such as 1 amino acid (e.g., Gly), 2, 3, 4, 5, 6, 7, 8, 9, 10, 10-20, 20-30, 30-50 or more than 50 amino acids. Exemplary flexible linkers include glycine polymers $(G)_n$, glycine-serine polymers (for example, $(GS)_n$, $GSGGS_n$, $GGGS_n$, $(G_mS_o)_n$, $(G_mS_oG_m)_n$, $(G_mS_oG_mS_oG_m)_n$, $(GSGGS_m)_n$, $(GSGS_mG)_n$ and $(GGGS_m)_n$, and combinations thereof, where m, and o are each independently selected from an integer of at least one), glycine-alanine polymers, alanine-serine polymers, and other flexible linkers. Glycine and glycine-serine polymers are relatively unstructured, and therefore may serve as a neutral tether between components. Exemplary flexible linkers include, but are not limited to GGSG, GGSGG, GSGSG, GSGGG, GGGSG, and GSSSG.

In some instances, the agent is a nucleic acid coding sequence. Depending on the desired ADAM17 polypeptide, the nucleic acid coding sequence may vary. Nucleic acids of interest include those encoding the ADAM17 polypeptides provided above. Specific nucleic acids of interest include, but are not limited to: NCBI Reference Sequence: XM_011510375.1; NCBI Reference Sequence: NM_003183.4; NCBI Reference Sequence: XM_011510378.1; NCBI Reference Sequence: XM_011510376.1 and NCBI Reference Sequence: XM_011510377.1.

By nucleic acid composition is meant a composition comprising a sequence of DNA having an open reading frame that encodes an ADAM17 polypeptide of interest, i.e., an ADAM17 coding sequence, and is capable, under appropriate conditions, of being expressed as an ADAM17 polypeptide. Also encompassed in this term are nucleic acids that are homologous, substantially similar or identical to the specific nucleic acids described above. In addition to the above described specific nucleic acid compositions, also of interest are homologues of the above sequences. In certain embodiments, sequence similarity between homologues is 20% or higher, such as 25% or higher, and including 30%, 35%, 40%, 50%, 60%, 70% or higher, including 75%, 80%, 85%, 90% and 95% or higher. Sequence similarity is calculated based on a reference sequence, which may be a subset of a larger sequence, such as a conserved motif, coding region, flanking region, etc. A reference sequence may be 18 nt long or longer, such as 30 nt long, and may extend to the complete sequence that is being compared. Algorithms for sequence analysis are known in the art, such as BLAST, described in Altschul et al. (1990), J. Mol. Biol. 215:403-10 (using default settings, i.e. parameters w=4 and T=17). Of particular interest in certain embodiments are nucleic acids of substantially the same length as human ADAM17 nucleic acids mentioned above, where by substantially the same length is meant that any difference in length does not exceed about 20 number %, usually does not exceed about 10 number % and more usually does not exceed about 5 number %; and have sequence identity to any of these sequences of at 90% or greater, such as 95% or greater and including 99% or greater over the entire length of the nucleic acid. In some embodiments, the nucleic acids have a sequence that is substantially similar or identical to the above specific sequences. By substantially similar is meant that sequence identity is 60% or greater, such as 75% or greater and including 80, 85, 90, or even 95% or greater. Nucleic acids of interest also include nucleic acids that encode the proteins encoded by the above described nucleic acids, but differ in sequence from the above described nucleic acids due to the degeneracy of the genetic code.

Nucleic acids as described herein may be present in a vector. Various vectors (e.g., viral vectors, bacterial vectors, or vectors capable of replication in eukaryotic and prokaryotic hosts) can be used in accordance with the present invention. Numerous vectors which can replicate in eukaryotic and prokaryotic hosts are known in the art and are commercially available. In some instances, such vectors used in accordance with the invention are composed of a bacterial origin of replication and a eukaryotic promoter operably linked to a DNA of interest.

Viral vectors used in accordance with the invention may be composed of a viral particle derived from a naturally-occurring virus which has been genetically altered to render the virus replication-defective and to express a recombinant gene of interest in accordance with the invention. Once the virus delivers its genetic material to a cell, it does not generate additional infectious virus but does introduce exogenous recombinant genes into the cell, preferably into the genome of the cell. Numerous viral vectors are well known in the art, including, for example, retrovirus, adenovirus, adeno-associated virus, herpes simplex virus (HSV), cytomegalovirus (CMV), vaccinia and poliovirus vectors.

The DNA of interest may be administered using a non-viral vector, for example, as a DNA- or RNA-liposome complex formulation. Such complexes comprise a mixture of lipids which bind to genetic material (DNA or RNA), providing a hydrophobic coat which allows the genetic material to be delivered into cells. Liposomes which can be used in accordance with the invention include DOPE (dioleyl phosphatidyl ethanol amine), CUDMEDA (N-(5-cholestrum-3-.beta.-ol 3-urethanyl)-N',N'-dimethylethylene diamine). When the DNA of interest is introduced using a liposome, in some instances one first determines in vitro the optimal values for the DNA: lipid ratios and the absolute concentrations of DNA and lipid as a function of cell death and transformation efficiency for the particular type of cell to be transformed. These values can then be used in or extrapolated for use in in vivo transformation. The in vitro determinations of these values can be readily carried out using techniques which are well known in the art.

Other non-viral vectors may also be used in accordance with the present invention. These include chemical formulations of DNA or RNA coupled to a carrier molecule (e.g., an antibody or a receptor ligand) which facilitates delivery to host cells for the purpose of altering the biological properties of the host cells. By the term "chemical formulations" is meant modifications of nucleic acids to allow coupling of the nucleic acid compounds to a carrier molecule such as a protein or lipid, or derivative thereof. Exemplary protein carrier molecules include antibodies specific to the cells of a targeted secretory gland or receptor ligands, i.e., molecules capable of interacting with receptors associated with a cell of a targeted secretory gland.

DNA constructs may include a promoter to facilitate expression of the DNA of interest within a target cell, such as a strong, eukaryotic promoter. Exemplary eukaryotic promoters include promoters from cytomegalovirus (CMV), mouse mammary tumor virus (MMTV), Rous sarcoma virus (RSV), and adenovirus. More specifically, exemplary promoters include the promoter from the immediate early gene of human CMV (Boshart et al., Cell 41:521-530, 1985) and the promoter from the long terminal repeat (LTR) of RSV (Gorman et al., Proc. Natl. Acad. Sci. USA 79:6777-6781, 1982).

Instead of administration of an ADAM17 polypeptide, e.g., as described above, the level of target ADAM17 activity in the subject may be enhanced by stimulating endogenous production an ADAM17 polypeptide in vivo. An example of such agents is phorbol 12-myristate 13-acetate (PMA) (as described in Garton et al., "Stimulated shedding of vascular cell adhesion molecule 1 (VCAM-1) is mediated by tumor necrosis factor-alpha-converting enzyme (ADAM 17)," J Biol Chem. (2003) 278(39):37459-64.

Also of interest are potentiators of ADAM17 activity. By ADAM17 potentiator is meant an agent or combination of agents that work to increase the desirable ADAM17 activity of endogenous ADAM17 polypeptides present in the subject being treated. The magnitude of the increase may vary, where in some instances the magnitude of the increase is 2-fold or greater, such as 5-fold or greater, including 10-fold or greater, e.g., 15-fold or greater, 20-fold or greater, 25-fold or greater (as compared to a suitable control). ADAM17 potentiators of interest may work through a variety of different mechanisms, e.g., by enhancing the binding interaction between an ADAM17 polypeptide and a desired target; by increasing the bioavailability of the endogenous pool, e.g., by sequestering undesirable competitive binding targets, etc.

In yet other embodiments, the agent is a small molecule agent that exhibits the desired ADAM17 activity. Naturally occurring or synthetic small molecule compounds of interest include numerous chemical classes, such as organic molecules, e.g., small organic compounds having a molecular weight of more than 50 and less than about 2,500 Daltons. Candidate agents comprise functional groups for structural interaction with proteins, particularly hydrogen bonding, and typically include at least an amine, carbonyl, hydroxyl or carboxyl group, preferably at least two of the functional chemical groups. The candidate agents may include cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. Such molecules may be identified, among other ways, by employing the screening protocols described below.

In some instances, the target activity of active cell surface VCAM-1 may be reduced by administering to the mammal an effective amount of agents that inhibits binding of active cell surface VCAM1 to a binding member, e.g., receptor, for which active cell surface VCAM1 is a ligand. As such, in some instances, an inhibitor of a binding interaction between active surface VCAM1 and specific binding partner thereof is provided to the adult mammal. Depending on the particular embodiments being practiced, a variety of different types of such active agents may be employed. In some embodiments, the agent is an agent that modulates, e.g., inhibits, target cell surface VCAM-1 activity by binding to an integrin that specifically binds to active cell surface VCAM-1, such as VLA-4 (Very Late Antigen-4 or integrin α4β1).

In certain embodiments, the administered active agent is a VLA-4 specific binding member. In general, useful VLA-4 specific binding members exhibit an affinity (Kd) for a target VLA-4, such as human VLA-4, that is sufficient to provide for the desired reduction in aging associated impairment VCAM-1 activity. As used herein, the term "affinity" refers to the equilibrium constant for the reversible binding of two agents; "affinity" can be expressed as a dissociation constant (Kd). Affinity can be at least 1-fold greater, at least 2-fold greater, at least 3-fold greater, at least 4-fold greater, at least 5-fold greater, at least 6-fold greater, at least 7-fold greater, at least 8-fold greater, at least 9-fold greater, at least 10-fold greater, at least 20-fold greater, at least 30-fold greater, at least 40-fold greater, at least 50-fold greater, at least 60-fold greater, at least 70-fold greater, at least 80-fold greater, at least 90-fold greater, at least 100-fold greater, or at least 1000-fold greater, or more, than the affinity of an antibody for unrelated amino acid sequences. Affinity of a specific binding member to a target protein can be, for example, from about 100 nanomolar (nM) to about 0.1 nM, from about 100 nM to about 1 picomolar (pM), or from about 100 nM to about 1 femtomolar (fM) or more. The term "binding" refers to a direct association between two molecules, due to, for example, covalent, electrostatic, hydrophobic, and ionic and/or hydrogen-bond interactions, including interactions such as salt bridges and water bridges. In some embodiments, the antibodies bind human VCAM-1 with nanomolar affinity or picomolar affinity. In some embodiments, the antibodies bind human VCAM-1 with a Kd of less than about 100 nM, 50 nM, 20 nM, 20 nM, or 1 nM. In some embodiments, the affinity between the binding member active agent in a binding complex with VCAM-1 is characterized by a $K_d$ (dissociation constant) of $10^{-6}$ M or less, such as $10^{-7}$ M or less, including $10^{-8}$ M or less, e.g., $10^{-9}$ M or less, $10^{-10}$ M or less, $10^{-11}$ M or less, $10^{-12}$ M or less, $10^{-13}$ M or less, $10^{-14}$ M or less, including $10^{-15}$ M or less.

Examples of VLA-4 specific binding members include VLA-4 antibodies and binding fragments thereof. Non-limiting examples of such antibodies include antibodies directed against any epitope of VLA-4. Also encompassed are bispecific antibodies, i.e., antibodies in which each of the two binding domains recognizes a different binding epitope. VLA-4 is an integrin dimer of Alpha-4 and Beta-1 subunits. The amino acid sequence of canonical human Alpha-4 integrin is provided at the website address produced by placing "http://www." before "uniprot.org/uniprot/P13612" as:

```
                                         (SEQ ID NO: 03)
MAWEARREPG PRRAAVRETV MLLLCLGVPT GRPYNVDTES

ALLYQGPHNT LFGYSVVLHS HGANRWLLVG APTANWLANA

SVINPGAIYR CRIGKNPGQT CEQLQLGSPN GEPCGKTCLE

ERDNQWLGVT LSRQPGENGS IVTCGHRWKN IFYIKNENKL

PTGGCYGVPP DLRTELSKRI APCYQDYVKK FGENFASCQA

GISSFYTKDL IVMGAPGSSY WTGSLFVYNI TTNKYKAFLD

KQNQVKFGSY LGYSVGAGHF RSQHTTEVVG GAPQHEQIGK
```

-continued
```
AYIFSIDEKE LNILHEMKGK KLGSYFGASV CAVDLNADGF

SDLLVGAPMQ STIREEGRVF VYINSGSGAV MNAMETNLVG

SDKYAARFGE SIVNLGDIDN DGFEDVAIGA PQEDDLQGAI

YIYNGRADGI SSTFSQRIEG LQISKSLSMF GQSISGQIDA

DNNGYVDVAV GAFRSDSAVL LRTRPVVIVD ASLSHPESVN

RTKFDCVENG WPSVCIDLTL CFSYKGKEVP GYIVLFYNMS

LDVNRKAESP PRFYFSSNGT SDVITGSIQV SSREANCRTH

QAFMRKDVRD ILTPIQIEAA YHLGPHVISK RSTEEFPPLQ

PILQQKKEKD IMKKTINFAR FCAHENCSAD LQVSAKIGFL

KPHENKTYLA VGSMKTLMLN VSLFNAGDDA YETTLHVKLP

VGLYFIKILE LEEKQINCEV TDNSGVVQLD CSIGYIYVDH

LSRIDISFLL DVSSLSRAEE DLSITVHATC ENEEEMDNLK

HSRVTVAIPL KYEVKLTVHG FVNPTSFVYG SNDENEPETC

MVEKMNLTFH VINTGNSMAP NVSVEIMVPN SFSPQTDKLF

NILDVQTTTG ECHFENYQRV CALEQQKSAM QTLKGIVRFL

SKTDKRLLYC IKADPHCLNF LCNFGKMESG KEASVHIQLE

GRPSILEMDE TSALKFEIRA TGFPEPNPRV IELNKDENVA

HVLLEGLHHQ RPKRYFTIVI ISSSLLLGLI VLLLISYVMW

KAGFFKRQYK SILQEENRRD SWSYINSKSN DD
```

The amino acid sequence of canonical human Beta-1 integrin is provided at the website having an address produced by placing "http://www." in front of "uniprot.org/uniprot/P05556" as:

```
                                         (SEQ ID NO: 04)
MNLQPIFWIG LISSVCCVFA QTDENRCLKA NAKSCGECIQ

AGPNCGWCTN STFLQEGMPT SARCDDLEAL KKKGCPPDDI

ENPRGSKDIK KNKNVTNRSK GTAEKLKPED ITQIQPQQLV

LRLRSGEPQT FTLKFKRAED YPIDLYYLMD LSYSMKDDLE

NVKSLGTDLM NEMRRITSDF RIGFGSFVEK TVMPYISTTP

AKLRNPCTSE QNCTSPFSYK NVLSLTNKGE VFNELVGKQR

ISGNLDSPEG GFDAIMQVAV CGSLIGWRNV TRLLVFSTDA

GFHFAGDGKL GGIVLPNDGQ CHLENNMYTM SHYYDYPSIA

HLVQKLSENN IQTIFAVTEE FQPVYKELKN LIPKSAVGTL

SANSSNVIQL IIDAYNSLSS EVILENGKLS EGVTISYKSY

CKNGVNGTGE NGRKCSNISI GDEVQFEISI TSNKCPKKDS

DSFKIRPLGF TEEVEVILQY ICECECQSEG IPESPKCHEG

NGTFECGACR CNEGRVGRHC ECSTDEVNSE DMDAYCRKEN

SSEICSNNGE CVCGQCVCRK RDNTNEIYSG KFCECDNFNC

DRSNGLICGG NGVCKCRVCE CNPNYTGSAC DCSLDTSTCE

ASNGQICNGR GICECGVCKC TDPKFQGQTC EMCQTCLGVC

AEHKECVQCRA FNKGEKKDT CTQECSYFNI TKVESRDKLP

QPVQPDPVSH CKEKDVDDCW FYFTYSVNGN NEVMVHVVEN
```

```
-continued
PECPTGPDII PIVAGVVAGI VLIGLALLLI WKLLMIIHDR

REFAKFEKEK MNAKWDTGEN PIYKSAVTTV VNPKYEGK
```

Antibody specific binding members that may be employed include full antibodies or immunoglobulins of any isotype, as well as fragments of antibodies which retain specific binding to antigen, including, but not limited to, Fab, Fv, scFv, and Fd fragments, chimeric antibodies, humanized antibodies, single-chain antibodies, and fusion proteins comprising an antigen-binding portion of an antibody and a non-antibody protein, where further details regarding the different types of antibody agents are as described above in connection with VCAM-1 specific antibodies, and therefore not repeated here but instead incorporated by reference. Specific examples of antibody agents that may be employed to reduce cell surface active VCAM-1 activity by binding to VLA-4, such as the Alpha-4 integrin subunit, include but are not limited to, those described in U.S. Pat. Nos. 8,900,577; 8,815,236; 8,349,321; 5,932,214; 5,871,734 and 5,840,299; the disclosures of which are herein incorporated by reference.

VLA-4 specific binding members also include non-antibody binding members. For example, small molecules that bind to VLA-4 and inhibit its activity are of interest. Naturally occurring or synthetic small molecule compounds of interest include numerous chemical classes, such as organic molecules, e.g., small organic compounds having a molecular weight of more than 50 and less than about 2,500 daltons. Candidate agents comprise functional groups for structural interaction with proteins, particularly hydrogen bonding, and typically include at least an amine, carbonyl, hydroxyl or carboxyl group, preferably at least two of the functional chemical groups. The candidate agents may include cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. Such molecules may be identified, among other ways, by employing the screening protocols described below. Specific examples of small molecule agents that bind to VLA-4 and may be employed to reduce cell surface active VCAM-1 activity include, but are not limited to: those compounds described in: U.S. Pat. Nos. 8,367,688; 7,973,044; 7,820,687; 7,745,454; 7,638,630; 7,452,912; 7,288,526; 6,953,802; 6,586,602; 6,559,127; 6,545,003; 6,525,026; 6,514,952; 6,495,525; 6,492,421; 6,432,923; the disclosures of which are herein incorporated by reference.

In those embodiments where an active agent is administered to the adult mammal, the active agent(s) may be administered to the adult mammal using any convenient administration protocol capable of resulting in the desired activity. Thus, the agent can be incorporated into a variety of formulations, e.g., pharmaceutically acceptable vehicles, for therapeutic administration. More particularly, the agents of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments (e.g., skin creams), solutions, suppositories, injections, inhalants and aerosols. As such, administration of the agents can be achieved in various ways, including oral, buccal, rectal, parenteral, intraperitoneal, intradermal, transdermal, intracheal, etc., administration.

In pharmaceutical dosage forms, the agents may be administered in the form of their pharmaceutically acceptable salts, or they may also be used alone or in appropriate association, as well as in combination, with other pharmaceutically active compounds. The following methods and excipients are merely exemplary and are in no way limiting.

For oral preparations, the agents can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The agents can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The agents can be utilized in aerosol formulation to be administered via inhalation. The compounds of the present invention can be formulated into pressurized acceptable propellants such as dichlorodifluoromethane, propane, nitrogen and the like.

Furthermore, the agents can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise the inhibitor(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Where the agent is a polypeptide, polynucleotide, analog or mimetic thereof, it may be introduced into tissues or host cells by any number of routes, including viral infection, microinjection, or fusion of vesicles. Jet injection may also be used for intramuscular administration, as described by Furth et al., Anal Biochem. (1992) 205:365-368. The DNA may be coated onto gold microparticles, and delivered intradermally by a particle bombardment device, or "gene gun" as described in the literature (see, for example, Tang et al., Nature (1992) 356:152-154), where gold microprojectiles are coated with the DNA, then bombarded into skin cells. For nucleic acid therapeutic agents, a number of different delivery vehicles find use, including viral and non-viral vector systems, as are known in the art.

Those of skill in the art will readily appreciate that dose levels can vary as a function of the specific compound, the nature of the delivery vehicle, and the like. Preferred dosages for a given compound are readily determinable by those of skill in the art by a variety of means.

In those embodiments where an effective amount of an active agent is administered to the adult mammal, the amount or dosage is effective when administered for a suitable period of time, such as one week or longer, including two weeks or longer, such as 3 weeks or longer, 4 weeks or longer, 8 weeks or longer, etc., so as to evidence a reduction in the impairment, e.g., cognition decline and/or cognitive improvement in the adult mammal. For example, an effective dose is the dose that, when administered for a suitable period of time, such as at least about one week, and maybe about two weeks, or more, up to a period of about 3 weeks, 4 weeks, 8 weeks, or longer, will slow e.g., by about 20% or more, e.g., by 30% or more, by 40% or more, or by 50% or more, in some instances by 60% or more, by 70% or more, by 80% or more, or by 90% or more, e.g., will halt, cognitive decline in a patient suffering from natural aging or an aging-associated disorder. In some instances, an effective amount or dose of active agent will not only slow or halt the progression of the disease condition but will also induce the reversal of the condition, i.e., will cause an improvement in cognitive ability. For example, in some instances, an effective amount is the amount that when administered for a suitable period of time, usually at least about one week, and maybe about two weeks, or more, up to a period of about 3 weeks, 4 weeks, 8 weeks, or longer will improve the cognitive abilities of an individual suffering from an aging-associated cognitive impairment by, for example 1.5-fold, 2-fold, 3-fold, 4-fold, 5-fold, in some instances 6-fold, 7-fold, 8-fold, 9-fold, or 10-fold or more relative to cognition prior to administration of the blood product.

Where desired, effectiveness of treatment may be assessed using any convenient protocol. Cognition tests and IQ test for measuring cognitive ability, e.g., attention and concentration, the ability to learn complex tasks and concepts, memory, information processing, visuospatial function, the ability to produce and understanding language, the ability to solve problems and make decisions, and the ability to perform executive functions, are well known in the art, any of which may be used to measure the cognitive ability of the individual before and/or during and after treatment with the subject blood product, e.g., to confirm that an effective amount has been administered. These include, for example, the General Practitioner Assessment of Cognition (GPCOG) test, the Memory Impairment Screen, the Mini Mental State Examination (MMSE), the California Verbal Learning Test, Second Edition, Short Form, for memory, the Delis-Kaplan Executive Functioning System test, the Alzheimer's Disease Assessment Scale (ADAS-Cog), the Psychogeriatric Assessment Scale (PAS) and the like. Progression of functional brain improvements may be detected by brain imaging techniques, such as Magnetic Resonance Imaging (MRI) or Positron Emission Tomography (PET) and the like. A wide range of additional functional assessments may be applied to monitor activities of daily living, executive functions, mobility, etc. In some embodiments, the method comprises the step of measuring cognitive ability, and detecting a decreased rate of cognitive decline, a stabilization of cognitive ability, and/or an increase in cognitive ability after administration of the blood product as compared to the cognitive ability of the individual before the blood product was administered. Such measurements may be made a week or more after administration of the blood product, e.g., 1 week, 2 weeks, 3 weeks, or more, for instance, 4 weeks, 6 weeks, or 8 weeks or more, e.g., 3 months, 4 months, 5 months, or 6 months or more.

Biochemically, by an "effective amount" or "effective dose" of active agent is meant an amount of active agent that will inhibit, antagonize, decrease, reduce, or suppress by about 20% or more, e.g., by 30% or more, by 40% or more, or by 50% or more, in some instances by 60% or more, by 70% or more, by 80% or more, or by 90% or more, in some cases by about 100%, i.e., to negligible amounts, and in some instances reverse, the reduction in synaptic plasticity and loss of synapses that occurs during the natural aging process or during the progression of an aging-associated disorder. In other words, cells present in adult mammals treated in accordance with methods of the invention will become more responsive to cues, e.g., activity cues, which promote the formation and maintenance of synapses.

Performance of methods of the invention, e.g., as described above, may manifest as improvements in observed synaptic plasticity, both in vitro and in vivo as an induction of long term potentiation. For example, the induction of LTP in neural circuits may be observed in awake individuals, e.g., by performing non-invasive stimulation techniques on awake individuals to induce LTP-like long-lasting changes in localized neural activity (Cooke S F, Bliss TV (2006) Plasticity in the human central nervous system. Brain. 129(Pt 7):1659-73); mapping plasticity and increased neural circuit activity in individuals, e.g., by using positron emission tomography, functional magnetic resonance imaging, and/or transcranial magnetic stimulation (Cramer and Bastings, "Mapping clinically relevant plasticity after stroke," Neuropharmacology (2000)39:842-51); and by detecting neural plasticity following learning, i.e., improvements in memory, e.g., by assaying retrieval-related brain activity (Buchmann et al., "Prion protein M129V polymorphism affects retrieval-related brain activity," Neuropsychologia. (2008) 46:2389-402) or, e.g., by imaging brain tissue by functional magnetic resonance imaging (fMRI) following repetition priming with familiar and unfamiliar objects (Soldan et al., "Global familiarity of visual stimuli affects repetition-related neural plasticity but not repetition priming," Neuroimage. (2008) 39:515-26; Soldan et al., "Aging does not affect brain patterns of repetition effects associated with perceptual priming of novel objects," J. Cogn. Neurosci. (2008) 20:1762-76). In some embodiments, the method includes the step of measuring synaptic plasticity, and detecting a decreased rate of loss of synaptic plasticity, a stabilization of synaptic plasticity, and/or an increase in synaptic plasticity after administration of the blood product as compared to the synaptic plasticity of the individual before the blood product was administered. Such measurements may be made a week or more after administration of the blood product, e.g., 1 week, 2 weeks, 3 weeks, or more, for instance, 4 weeks, 6 weeks, or 8 weeks or more, e.g., 3 months, 4 months, 5 months, or 6 months or more.

In some instances, the methods result in a change in expression levels of one or more genes in one or more tissues of the host, e.g., as compared to a suitable control (such as described in the Experimental section, below). The change in expression level of a given gene may be 0.5 fold or greater, such as 1.0 fold or greater, including 1.5 fold or greater. The tissue may vary, and in some instances is nervous system tissue, e.g., central nervous system tissue, including brain tissue, e.g., hippocampal tissue. In some instances, the modulation of hippocampal gene expression is manifested as enhanced hippocampal plasticity, e.g., as compared to a suitable control.

In some instances, treatment results in an enhancement in the levels of one or more proteins in one or more tissues of the host, e.g., as compared to a suitable control (such as described in the Experimental section, below). The change in protein level of a given protein may be 0.5 fold or greater, such as 1.0 fold or greater, including 1.5 fold or greater, where in some instances the level may approach that of a healthy wild-type level, e.g., within 50% or less, such as 25% or less, including 10% or less, e.g., 5% or less of the healthy wild-type level. The tissue may vary, and in some instances is nervous system tissue, e.g., central nervous system tissue, including brain tissue, e.g., hippocampal tissue.

In some instances, the methods result in one or more structural changes in one or more tissues. The tissue may vary, and in some instances is nervous system tissue, e.g., central nervous system tissue, including brain tissue, e.g., hippocampal tissue. Structure changes of interest include an increase in dendritic spine density of mature neurons in the dentate gyrus (DG) of the hippocampus, e.g., as compared to a suitable control. In some instances, the modulation of hippocampal structure is manifested as enhanced synapse formation, e.g., as compared to a suitable control. In some instances, the methods may result in an enhancement of long term potentiation, e.g., as compared to a suitable control. In some instances, the structural change manifests as a promotion or increase in non-reactive, non-inflammatory microglial expansion In some instances, practice of the methods, e.g., as described above, results in an increase in neurogenesis in the adult mammal. The increase may be identified in a number of different ways, e.g., as described below in the Experimental section. In some instances, the increase in neurogenesis manifests as an increase the amount of Dcx-positive immature neurons, e.g., where the increase may be 2-fold or greater. In some instances, the increase in neurogenesis manifests as an increase in the number of BrdU/NeuN positive cells, where the increase may be 2-fold or greater.

In some instances, the methods result in enhancement in learning and memory, e.g., as compared to a suitable control. Enhancement in learning and memory may be evaluated in a number of different ways, e.g., the contextual fear conditioning and/or radial arm water maze (RAWM) paradigms described in the experimental section, below. When measured by contextual fear conditioning, treatment results in some instances in increased freezing in contextual, but not cued, memory testing. When measured by RAWM, treatment results in some instances in enhanced learning and memory for platform location during the testing phase of the task. In some instances, treatment is manifested as enhanced cognitive improvement in hippocampal-dependent learning and memory, e.g., as compared to a suitable control.

In some embodiments, cell surface active VCAM-1 reduction, e.g., as described above, may be performed in conjunction with an active agent having activity suitable to treat aging-associated cognitive impairment. For example, a number of active agents have been shown to have some efficacy in treating the cognitive symptoms of Alzheimer's disease (e.g., memory loss, confusion, and problems with thinking and reasoning), e.g., cholinesterase inhibitors (e.g., Donepezil, Rivastigmine, Galantamine, Tacrine), Memantine, and Vitamin E. As another example, a number of agents have been shown to have some efficacy in treating behavioral or psychiatric symptoms of Alzheimer's Disease, e.g., citalopram (Celexa), fluoxetine (Prozac), paroxeine (Paxil), sertraline (Zoloft), trazodone (Desyrel), lorazepam (Ativan), oxazepam (Serax), aripiprazole (Abilify), clozapine (Clozaril), haloperidol (Haldol), olanzapine (Zyprexa), quetiapine (Seroquel), risperidone (Risperdal), and ziprasidone (Geodon).

In some aspects of the subject methods, the method further comprises the step of measuring cognition and/or synaptic plasticity after treatment, e.g., using the methods described herein or known in the art, and determining that the rate of cognitive decline or loss of synaptic plasticity have been reduced and/or that cognitive ability or synaptic plasticity have improved in the individual. In some such instances, the determination is made by comparing the results of the cognition or synaptic plasticity test to the results of the test performed on the same individual at an earlier time, e.g., 2 weeks earlier, 1 month earlier, 2 months earlier, 3 months earlier, 6 months earlier, 1 year earlier, 2 years earlier, 5 years earlier, or 10 years earlier, or more.

In some embodiments, the subject methods further include diagnosing an individual as having a cognitive impairment, e.g., using the methods described herein or known in the art for measuring cognition and synaptic plasticity, prior to administering the subject plasma-comprising blood product. In some instances, the diagnosing will comprise measuring cognition and/or synaptic plasticity and comparing the results of the cognition or synaptic plasticity test to one or more references, e.g., a positive control and/or a negative control. For example, the reference may be the results of the test performed by one or more age-matched individuals that experience aging-associated cognitive impairments (i.e., positive controls) or that do not experience aging-associated cognitive impairments (i.e., negative controls). As another example, the reference may be the results of the test performed by the same individual at an earlier time, e.g., 2 weeks earlier, 1 month earlier, 2 months earlier, 3 months earlier, 6 months earlier, 1 year earlier, 2 years earlier, 5 years earlier, or 10 years earlier, or more.

In some embodiments, the subject methods further comprise diagnosing an individual as having an aging-associated disorder, e.g., Alzheimer's disease, Parkinson's disease, frontotemporal dementia, progressive supranuclear palsy, Huntington's disease, amyotrophic lateral sclerosis, spinal muscular atrophy, multiple sclerosis, multi-system atrophy, glaucoma, ataxias, myotonic dystrophy, dementia, and the like. Methods for diagnosing such aging-associated disorders are well-known in the art, any of which may be used by the ordinarily skilled artisan in diagnosing the individual. In some embodiments, the subject methods further comprise both diagnosing an individual as having an aging-associated disorder and as having a cognitive impairment.

Utility

The subject methods find use in treating, including preventing, aging-associated impairments and conditions associated therewith, such as impairments in the cognitive ability of individuals. Individuals suffering from or at risk of developing an aging-associated cognitive impairments include individuals that are about 50 years old or older, e.g., 60 years old or older, 70 years old or older, 80 years old or older, 90 years old or older, and usually no older than 100 years old, i.e., between the ages of about 50 and 100, e.g., 50, 55, 60, 65, 70, 75, 80, 85, 90, 95 or about 100 years old, and are suffering from cognitive impairment associated with natural aging process, e.g., mild cognitive impairment (M.C.I.); and individuals that are about 50 years old or older, e.g., 60 years old or older, 70 years old or older, 80 years old or older, 90 years old or older, and usually no older than 100 years old, i.e., between the ages of about 50 and 90, e.g., 50, 55, 60, 65, 70, 75, 80, 85, 90, 95 or about 100 years old, that have not yet begun to show symptoms of cognitive impairment. Examples of cognitive impairments that are due to natural aging include the following:

Mild Cognitive Impairment (M.C.I.) is a modest disruption of cognition that manifests as problems with memory or other mental functions such as planning, following instructions, or making decisions that have worsened over time while overall mental function and daily activities are not impaired. Thus, although significant neuronal death does not typically occur, neurons in the aging brain are vulnerable to sub-lethal age-related alterations in structure, synaptic integrity, and molecular processing at the synapse, all of which impair cognitive function.

Individuals suffering from or at risk of developing an aging-associated cognitive impairment that will benefit from treatment with the subject plasma-comprising blood product, e.g., by the methods disclosed herein, also include individuals of any age that are suffering from a cognitive impairment due to an aging-associated disorder; and individuals of any age that have been diagnosed with an aging-associated disorder that is typically accompanied by cognitive impairment, where the individual has not yet begun to present with symptoms of cognitive impairment. Examples of such aging-associated disorders include the following:

Alzheimer's Disease (AD).

Alzheimer's disease is a progressive, inexorable loss of cognitive function associated with an excessive number of senile plaques in the cerebral cortex and subcortical gray matter, which also contains b-amyloid and neurofibrillary tangles consisting of tau protein. The common form affects persons >60 yr old, and its incidence increases as age advances. It accounts for more than 65% of the dementias in the elderly.

The cause of Alzheimer's disease is not known. The disease runs in families in about 15 to 20% of cases. The remaining, so-called sporadic cases have some genetic determinants. The disease has an autosomal dominant genetic pattern in most early-onset and some late-onset cases but a variable late-life penetrance. Environmental factors are the focus of active investigation.

In the course of the disease, synapses, and ultimately neurons are lost within the cerebral cortex, hippocampus, and subcortical structures (including selective cell loss in the nucleus basalis of Meynert), locus caeruleus, and nucleus raphae dorsalis. Cerebral glucose use and perfusion is reduced in some areas of the brain (parietal lobe and temporal cortices in early-stage disease, prefrontal cortex in late-stage disease). Neuritic or senile plaques (composed of neurites, astrocytes, and glial cells around an amyloid core) and neurofibrillary tangles (composed of paired helical filaments) play a role in the pathogenesis of Alzheimer's disease. Senile plaques and neurofibrillary tangles occur with normal aging, but they are much more prevalent in persons with Alzheimer's disease.

Parkinson's Disease.

Parkinson's Disease (PD) is an idiopathic, slowly progressive, degenerative CNS disorder characterized by slow and decreased movement, muscular rigidity, resting tremor, and postural instability. Originally considered primarily a motor disorder, PD is now recognized to also affect cognition, behavior, sleep, autonomic function, and sensory function. The most common cognitive impairments include an impairment in attention and concentration, working memory, executive function, producing language, and visuospatial function. In primary Parkinson's disease, the pigmented neurons of the substantia nigra, locus caeruleus, and other brain stem dopaminergic cell groups are lost. The cause is not known. The loss of substantia nigra neurons, which project to the caudate nucleus and putamen, results in depletion of the neurotransmitter dopamine in these areas. Onset is generally after age 40, with increasing incidence in older age groups.

Secondary parkinsonism results from loss of or interference with the action of dopamine in the basal ganglia due to other idiopathic degenerative diseases, drugs, or exogenous toxins. The most common cause of secondary parkinsonism is ingestion of antipsychotic drugs or reserpine, which produce parkinsonism by blocking dopamine receptors. Less common causes include carbon monoxide or manganese poisoning, hydrocephalus, structural lesions (tumors, infarcts affecting the midbrain or basal ganglia), subdural hematoma, and degenerative disorders, including striatonigral degeneration.

Frontotemporal Dementia.

Frontotemporal dementia (FTD) is a condition resulting from the progressive deterioration of the frontal lobe of the brain. Over time, the degeneration may advance to the temporal lobe. Second only to Alzheimer's disease (AD) in prevalence, FTD accounts for 20% of pre-senile dementia cases. Symptoms are classified into three groups based on the functions of the frontal and temporal lobes affected: Behavioural variant FTD (bvFTD), with symptoms include lethargy and aspontaneity on the one hand, and disinhibition on the other; progressive nonfluent aphasia (PNFA), in which a breakdown in speech fluency due to articulation difficulty, phonological and/or syntactic errors is observed but word comprehension is preserved; and semantic dementia (SD), in which patients remain fluent with normal phonology and syntax but have increasing difficulty with naming and word comprehension. Other cognitive symptoms common to all FTD patients include an impairment in executive function and ability to focus. Other cognitive abilities, including perception, spatial skills, memory and praxis typically remain intact. FTD can be diagnosed by observation of reveal frontal lobe and/or anterior temporal lobe atrophy in structural MRI scans.

A number of forms of FTD exist, any of which may be treated or prevented using the subject methods and compositions. For example, one form of frontotemporal dementia is Semantic Dementia (SD). SD is characterized by a loss of semantic memory in both the verbal and non-verbal domains. SD patients often present with the complaint of word-finding difficulties. Clinical signs include fluent aphasia, anomia, impaired comprehension of word meaning, and associative visual agnosia (the inability to match semantically related pictures or objects). As the disease progresses, behavioral and personality changes are often seen similar to those seen in frontotemporal dementia although cases have been described of 'pure' semantic dementia with few late behavioral symptoms. Structural MRI imaging shows a characteristic pattern of atrophy in the temporal lobes (predominantly on the left), with inferior greater than superior involvement and anterior temporal lobe atrophy greater than posterior.

As another example, another form of frontotemporal dementia is Pick's disease (PiD, also PcD). A defining characteristic of the disease is build-up of tau proteins in neurons, accumulating into silver-staining, spherical aggregations known as "Pick bodies". Symptoms include loss of speech (aphasia) and dementia. Patients with orbitofrontal dysfunction can become aggressive and socially inappropriate. They may steal or demonstrate obsessive or repetitive stereotyped behaviors. Patients with dorsomedial or dorsolateral frontal dysfunction may demonstrate a lack of concern, apathy, or decreased spontaneity. Patients can demonstrate an absence of self-monitoring, abnormal self-awareness, and an inability to appreciate meaning. Patients with gray matter loss in the bilateral posterolateral orbitofrontal cortex and right anterior insula may demonstrate changes in eating behaviors, such as a pathologic sweet tooth. Patients with more focal gray matter loss in the anterolateral orbitofrontal cortex may develop hyperphagia. While some of the symptoms can initially be alleviated, the disease progresses and patients often die within two to ten years.

Huntington's Disease.

Huntington's disease (HD) is a hereditary progressive neurodegenerative disorder characterized by the development of emotional, behavioral, and psychiatric abnormalities; loss of intellectual or cognitive functioning; and movement abnormalities (motor disturbances). The classic signs of HD include the development of chorea—involuntary, rapid, irregular, jerky movements that may affect the face, arms, legs, or trunk—as well as cognitive decline including the gradual loss of thought processing and acquired intellectual abilities. There may be impairment of memory, abstract thinking, and judgment; improper perceptions of time, place, or identity (disorientation); increased agitation; and personality changes (personality disintegration). Although symptoms typically become evident during the fourth or fifth decades of life, the age at onset is variable and ranges from early childhood to late adulthood (e.g., 70s or 80s).

HD is transmitted within families as an autosomal dominant trait. The disorder occurs as the result of abnormally long sequences or "repeats" of coded instructions within a gene on chromosome 4 (4p16.3). The progressive loss of nervous system function associated with HD results from loss of neurons in certain areas of the brain, including the basal ganglia and cerebral cortex.

Amyotrophic Lateral Sclerosis.

Amyotrophic lateral sclerosis (ALS) is a rapidly progressive, invariably fatal neurological disease that attacks motor neurons. Muscular weakness and atrophy and signs of anterior horn cell dysfunction are initially noted most often in the hands and less often in the feet. The site of onset is random, and progression is asymmetric. Cramps are common and may precede weakness. Rarely, a patient survives 30 years; 50% die within 3 years of onset, 20% live 5 years, and 10% live 10 years. Diagnostic features include onset during middle or late adult life and progressive, generalized motor involvement without sensory abnormalities. Nerve conduction velocities are normal until late in the disease. Recent studies have documented the presentation of cognitive impairments as well, particularly a reduction in immediate verbal memory, visual memory, language, and executive function.

A decrease in cell body area, number of synapses and total synaptic length has been reported in even normal-appearing neurons of the ALS patients. It has been suggested that when the plasticity of the active zone reaches its limit, a continuing loss of synapses can lead to functional impairment. Promoting the formation or new synapses or preventing synapse loss may maintain neuron function in these patients.

Multiple Sclerosis.

Multiple Sclerosis (MS) is characterized by various symptoms and signs of CNS dysfunction, with remissions and recurring exacerbations. The most common presenting symptoms are paresthesias in one or more extremities, in the trunk, or on one side of the face; weakness or clumsiness of a leg or hand; or visual disturbances, e.g., partial blindness and pain in one eye (retrobulbar optic neuritis), dimness of vision, or scotomas. Common cognitive impairments include impairments in memory (acquiring, retaining, and retrieving new information), attention and concentration (particularly divided attention), information processing, executive functions, visuospatial functions, and verbal fluency. Common early symptoms are ocular palsy resulting in double vision (diplopia), transient weakness of one or more extremities, slight stiffness or unusual fatigability of a limb, minor gait disturbances, difficulty with bladder control, vertigo, and mild emotional disturbances; all indicate scattered CNS involvement and often occur months or years before the disease is recognized. Excess heat may accentuate symptoms and signs.

The course is highly varied, unpredictable, and, in most patients, remittent. At first, months or years of remission may separate episodes, especially when the disease begins with retrobulbar optic neuritis. However, some patients have frequent attacks and are rapidly incapacitated; for a few the course can be rapidly progressive.

Glaucoma.

Glaucoma is a common neurodegenerative disease that affects retinal ganglion cells (RGCs). Evidence supports the existence of compartmentalized degeneration programs in synapses and dendrites, including in RGCs. Recent evidence also indicates a correlation between cognitive impairment in older adults and glaucoma (Yochim B P, et al. Prevalence of cognitive impairment, depression, and anxiety symptoms among older adults with glaucoma. J Glaucoma. 2012; 21(4):250-254).

Myotonic Dystrophy.

Myotonic dystrophy (DM) is an autosomal dominant multisystem disorder characterized by dystrophic muscle weakness and myotonia. The molecular defect is an expanded trinucleotide (CTG) repeat in the 3' untranslated region of the myotonin-protein kinase gene on chromosome 19q. Symptoms can occur at any age, and the range of clinical severity is broad. Myotonia is prominent in the hand muscles, and ptosis is common even in mild cases. In severe cases, marked peripheral muscular weakness occurs, often with cataracts, premature balding, hatchet facies, cardiac arrhythmias, testicular atrophy, and endocrine abnormalities (e.g., diabetes mellitus). Mental retardation is common in severe congenital forms, while an aging-related decline of frontal and temporal cognitive functions, particularly language and executive functions, is observed in milder adult forms of the disorder. Severely affected persons die by their early 50s.

Dementia.

Dementia describes class of disorders having symptoms affecting thinking and social abilities severely enough to interfere with daily functioning. Other instances of dementia in addition to the dementia observed in later stages of the aging-associated disorders discussed above include vascular dementia, and dementia with Lewy bodies, described below.

In vascular dementia, or "multi-infarct dementia", cognitive impairment is caused by problems in supply of blood to the brain, typically by a series of minor strokes, or sometimes, one large stroke preceded or followed by other smaller strokes. Vascular lesions can be the result of diffuse cerebrovascular disease, such as small vessel disease, or focal lesions, or both. Patients suffering from vascular dementia present with cognitive impairment, acutely or subacutely, after an acute cerebrovascular event, after which progressive cognitive decline is observed.

Cognitive impairments are similar to those observed in Alzheimer's disease, including impairments in language, memory, complex visual processing, or executive function, although the related changes in the brain are not due to AD pathology but to chronic reduced blood flow in the brain, eventually resulting in dementia. Single photon emission computed tomography (SPECT) and positron emission tomography (PET) neuroimaging may be used to confirm a diagnosis of multi-infarct dementia in conjunction with evaluations involving mental status examination.

Dementia with Lewy bodies (DLB, also known under a variety of other names including Lewy body dementia, diffuse Lewy body disease, cortical Lewy body disease, and senile dementia of Lewy type) is a type of dementia characterized anatomically by the presence of Lewy bodies (clumps of alpha-synuclein and ubiquitin protein) in neurons, detectable in post mortem brain histology. Its primary feature is cognitive decline, particularly of executive functioning. Alertness and short term memory will rise and fall. Persistent or recurring visual hallucinations with vivid and detailed pictures are often an early diagnostic symptom. DLB it is often confused in its early stages with Alzheimer's disease and/or vascular dementia, although, where Alzheimer's disease usually begins quite gradually, DLB often has a rapid or acute onset. DLB symptoms also include motor symptoms similar to those of Parkinson's. DLB is distinguished from the dementia that sometimes occurs in Parkinson's disease by the time frame in which dementia symptoms appear relative to Parkinson symptoms. Parkinson's disease with dementia (PDD) would be the diagnosis when dementia onset is more than a year after the onset of Parkinson's. DLB is diagnosed when cognitive symptoms begin at the same time or within a year of Parkinson symptoms.

Progressive Supranuclear Palsy.

Progressive supranuclear palsy (PSP) is a brain disorder that causes serious and progressive problems with control of gait and balance, along with complex eye movement and thinking problems. One of the classic signs of the disease is an inability to aim the eyes properly, which occurs because of lesions in the area of the brain that coordinates eye movements. Some individuals describe this effect as a blurring. Affected individuals often show alterations of mood and behavior, including depression and apathy as well as progressive mild dementia. The disorder's long name indicates that the disease begins slowly and continues to get worse (progressive), and causes weakness (palsy) by damaging certain parts of the brain above pea-sized structures called nuclei that control eye movements (supranuclear). PSP was first described as a distinct disorder in 1964, when three scientists published a paper that distinguished the condition from Parkinson's disease. It is sometimes referred to as Steele-Richardson-Olszewski syndrome, reflecting the combined names of the scientists who defined the disorder. Although PSP gets progressively worse, no one dies from PSP itself.

Ataxia.

People with ataxia have problems with coordination because parts of the nervous system that control movement and balance are affected. Ataxia may affect the fingers, hands, arms, legs, body, speech, and eye movements. The word ataxia is often used to describe a symptom of incoordination which can be associated with infections, injuries, other diseases, or degenerative changes in the central nervous system. Ataxia is also used to denote a group of specific degenerative diseases of the nervous system called the hereditary and sporadic ataxias which are the National Ataxia Foundation's primary emphases.

Multiple-System Atrophy.

Multiple-system atrophy (MSA) is a degenerative neurological disorder. MSA is associated with the degeneration of nerve cells in specific areas of the brain. This cell degeneration causes problems with movement, balance, and other autonomic functions of the body such as bladder control or blood-pressure regulation. The cause of MSA is unknown and no specific risk factors have been identified. Around 55% of cases occur in men, with typical age of onset in the late 50s to early 60s. MSA often presents with some of the same symptoms as Parkinson's disease. However, MSA patients generally show minimal if any response to the dopamine medications used for Parkinson's.

In some embodiments, the subject methods and compositions find use in slowing the progression of aging-associated cognitive impairment. In other words, cognitive abilities in the individual will decline more slowly following treatment by the disclosed methods than prior to or in the absence of treatment by the disclosed methods. In some such instances, the subject methods of treatment include measuring the progression of cognitive decline after treatment, and determining that the progression of cognitive decline is reduced. In some such instances, the determination is made by comparing to a reference, e.g., the rate of cognitive decline in the individual prior to treatment, e.g., as determined by measuring cognition prior at two or more time points prior to administration of the subject blood product.

The subject methods and compositions also find use in stabilizing the cognitive abilities of an individual, e.g., an individual suffering from aging-associated cognitive decline or an individual at risk of suffering from aging-associated cognitive decline. For example, the individual may demonstrate some aging-associated cognitive impairment, and progression of cognitive impairment observed prior to treatment with the disclosed methods will be halted following treatment by the disclosed methods. As another example, the individual may be at risk for developing an aging-associated cognitive decline (e.g., the individual may be aged 50 years old or older, or may have been diagnosed with an aging-associated disorder), and the cognitive abilities of the individual are substantially unchanged, i.e., no cognitive decline can be detected, following treatment by the disclosed methods as compared to prior to treatment with the disclosed methods.

The subject methods and compositions also find use in reducing cognitive impairment in an individual suffering from an aging-associated cognitive impairment. In other words, cognitive ability is improved in the individual following treatment by the subject methods. For example, the cognitive ability in the individual is increased, e.g., by 2-fold or more, 5-fold or more, 10-fold or more, 15-fold or more, 20-fold or more, 30-fold or more, or 40-fold or more, including 50-fold or more, 60-fold or more, 70-fold or more, 80-fold or more, 90-fold or more, or 100-fold or more, following treatment by the subject methods relative to the cognitive ability that is observed in the individual prior to treatment by the subject methods. In some instances, treatment by the subject methods and compositions restores the cognitive ability in the individual suffering from aging-associated cognitive decline, e.g., to their level when the individual was about 40 years old or less. In other words, cognitive impairment is abrogated.

The subject methods and compositions also find use in reducing cognitive impairment in an individual suffering from cognitive decline as a consequence of systemic inflammation, radiation, chemotherapy, frailty, and kidney dysfunction. The subject methods and compositions also find use in reducing, if not preventing, age-associated brain inflammation, neurodegeneration and cognitive decline.

Reagents, Devices and Kits

Also provided are reagents, devices and kits thereof for practicing one or more of the above-described methods. The subject reagents, devices and kits thereof may vary greatly. Reagents and devices of interest include those mentioned above with respect to the methods of reducing cell surface active VCAM-1 levels in an adult mammal.

In addition to the above components, the subject kits will further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, portable flash drive, etc., on which the information has been recorded. Yet another means that may be present is a website address which may be used via the internet to access the information at a removed site. Any convenient means may be present in the kits.

The following examples are provided by way of illustration and not by way of limitation.

EXPERIMENTAL

I. Results

A. Brain Aging is Linked to Increased Shedding of VCAM1 into the Systemic Milieu To identify circulating factors associated with aging and cognitive impairments, a proteomic approach was developed that utilizes antibody-based hybridization microarrays, which approach allows for the measurement of relative levels of >400 secreted signaling proteins including most interleukins, chemokines, growth factors, or receptor/membrane proteins shed into the extracellular space in plasma, CSF, or other fluids in mice (Subramanian et al., "Gene set enrichment analysis: A knowledge-based approach for interpreting genome-wide expression profiles," PNAS (2005) 102:15545-15550; Langfelder & Horvath, "WGCNA: an R package for weighted correlation network analysis," BMC Bioinformatics (2008) 9: 559; Ray et al., "Classification and prediction of clinical Alzheimer's diagnosis based on plasma signaling proteins," Nat. Med. (2007) 13:1359-62).

A study using the 400-protein-array was run on plasma samples obtained from 3-month-old mice, which had been surgically connected to 18-month-old mice and undergoing parabiosis for 5 weeks (heterochronic). As controls, samples from isochronic pairs of 3-month-old mice were used. After normalization and analysis with various tests including the Significance Analysis of Microarray (SAM) (Roxas & Li, "Significance analysis of microarray for relative quantitation of LC/MS data in proteomics," BMC Bioinformatics (2008) 9: 187), 9 top factors emerged, with 1 soluble factor, VCAM1, known to be specifically expressed on BECs and its membrane-bound form upregulated by inflammation (FIG. 1A, (Rossi et al., "Vascular inflammation in central nervous system diseases: adhesion receptors controlling leukocyte-endothelial interactions," J. Leukoc. Biol. (2011) 89: 539-56). ELISA measurements of plasma from young heterochronic and isochronic parabionts showed a two-fold increase in sVCAM1 in the young mice exposed to old compared with young blood, similar to levels seen in isochronic aged mice (FIG. 1B). This finding was confirmed in a larger cohort of mice, and sVCAM1 was shown to increase in the plasma of young and aged humans (See FIGS. 10A-C).

B. Primary Mouse BECs and Bend.3 Cells Upregulate VCAM1 in the Presence of Aged Plasma In Vitro To determine whether aged plasma can directly regulate VCAM1 expression on BECs, we cultured Bend.3 cells (transformed BEC line) or primary BECs isolated from the cortex and hippocampi of young (2-3 month) C57BL6/J mice in 5% young (3 month) or aged (18 month old) pooled mice plasma or young (<25 years) or aged (>65 years) pooled human plasma for 24 hours and analyzed expression of VCAM1 at the mRNA and protein levels via qPCR and immunofluorescence (FIG. 2). Primary BECs exposed to aged mouse plasma have a two-fold increase in Vcam1 mRNA levels (FIG. 2C). Similarly, Bend.3 cells exposed to aged human plasma have a 1.5-fold increase in Vcam1 mRNA levels (FIG. 2D). Both mice and human aged plasma induced BECs to express 2-3 times higher levels of VCAM1 than young plasma as measured by percentage of area staining and intensity (FIG. 2E-J). Upregulation of membrane VCAM1 by aged plasma was also confirmed via flow cytometry (FIG. 2K-L). Other adhesion molecules, namely ICAM1, E-selectin, and P-selectin, were only mildly or not significantly upregulated in the presence of aged plasma on Bend.3 cells and their expression levels were generally lower than VCAM1 (data not shown).

C. VCAM1 Increases in the Hippocampus with Age and in Young Mice Exposed to an Aged Systemic Milieu.

Immunofluorescence of whole brain tissue sections for VCAM1 and Aquaporin4 (Aqp4), a marker of astrocytic endfeet that line brain endothelium (Wolburg-Buchholz et al., "Loss of astrocyte polarity marks blood-brain barrier impairment during experimental autoimmune encephalomyelitis," Acta Neuropathol. (2009) 118: 219-33), was performed on young (3 month) and aged (18 month) male C57BL6/J mice. Interestingly, there was a four-fold increase in VCAM1 expression in brain endothelium in the hippocampi of aged mice (FIG. 3A-C). Another brain region sensitive to cognitive dysfunction and neurodegeneration, the cortex, also showed increased VCAM1 with aging (FIG. 9A-C). Additionally, qPCR of flow-sorted CD31+ BECs from murine cortex and hippocampi revealed an age dependent increase in Vcam1 mRNA (FIG. 3D-E).

To determine whether VCAM1 expression on brain endothelium is regulated by the systemic milieu, immunofluorescence of whole brain tissue sections for VCAM1 and lectin, a marker of brain blood vessels (Winkler et al, "GLUT1 reductions exacerbate Alzheimer's disease vasculo-neuronal dysfunction and degeneration," Nat. Neurosci. (2015) 18: 521-530), was performed on young (3 month) and aged (18 month) male C57BL6/J mice connected through parabiosis (heterochronic). Mice connected to age-matched mice were used as controls (isochronic). Interestingly, there was a four-fold increase in VCAM1 expression and colocalization with lectin+ brain endothelium in the hippocampi of young heterochronic mice, similar to the levels seen in isochronic aged mice (FIG. 3F-G). Other brain regions, including cortex also showed increased VCAM1 in young heterochronic mice exposed to an aged systemic mileu via parabiosis (FIG. 9D-E).

These data demonstrate that the aged systemic milieu upregulates VCAM1 expression on BECs. Considering that VCAM1 inhibits SVZ neurogenesis and inhibition of leukocyte adhesion to VCAM1 ameliorated the pathology of CNS inflammatory diseases (Rossi et al., "Vascular inflammation in central nervous system diseases: adhesion receptors controlling leukocyte-endothelial interactions," J. Leukoc. Biol. (2011) 89: 539-56; Fabene et al, "A role for leukocyte-endothelial adhesion mechanisms in epilepsy," Nat. Med. (2008) 14: 1377-83 (2008); Kokovay et al., "VCAM1 is essential to maintain the structure of the SVZ niche and acts as an environmental sensor to regulate SVZ lineage progression," Cell Stem Cell (2012) 11: 220-30), these data provide strong rationale for a mechanism by which VCAM1 upregulation by the aged systemic milieu plays a direct role in the decline of hippocampal neurogenesis and may possibly mediate brain inflammation in response to systemic inflammation.

D. Shedding of VCAM1 by Plasma Factors May be Regulated by ADAM17, which Declines with Aging in BECs.

Endothelial membrane bound VCAM1 expression increases in the hippocampi of aged mice and of heterochronic young parabionts exposed to an aged systemic milieu while the soluble, shed form of VCAM1 (sVCAM1) increases in plasma of heterochronic young parabionts (FIGS. 1 and 3). Additionally, exposure to aged, but not young, plasma led to a strong increase in VCAM1 expression in Bend.3 cells (transformed BEC line) and primary cultured BECs (FIG. 2).

To determine the mechanisms underlying this transcriptional and post-translational regulation of VCAM1 with aging, we first assessed mRNA levels of Adam17, a metalloproteinase that is a known specific cleaver of VCAM1 and that is also expressed in BECs, in primary flow-sorted CD31+ young and aged BECs, via RNA sequencing and PCR (FIG. 4A-D). There is a two-fold decrease in Adam17 mRNA FPKM values as determined by RNA-seq (FIG. 4B-C, *p=0.02), and PCR bands of converted cDNA revealed little to no amplification in individual aged BEC samples (FIG. 4D). To assess whether aged plasma factors regulate BEC-specific ADAM17 expression, Bend.3 cells were treated for 24 hours with 5% young or aged mouse plasma followed by protein analysis. Western blot analysis revealed that Bend.3 cells cultured in aged plasma have a two-fold decrease in ADAM17 expression as compared to those cultured in young plasma (FIG. 4E-F).

E. Aged Plasma Injections into Young Mice Over 3 Weeks Reduces Neurogenesis and Increases Brain Inflammation Given that BEC-specific VCAM1 expression increases with age in the neurogenic hippocampal dentate gyrus and is regulated by the aged systemic milieu, we next asked whether VCAM1 is required for the detrimental effects of aged plasma on young hippocampal neurogenesis and brain inflammation, two hallmarks of decline in brain function with aging. Considering that aged mouse plasma injections into young mice can inhibit neurogenesis (Villeda et al., "The ageing systemic milieu negatively regulates neurogenesis and cognitive function," Nature (2011) 477: 90-4), that aged mouse and human plasma directly upregulate VCAM1 on cultured Bend.3 cells and primary BECs (FIG. 2), that both aged mice and young heterochronic mice exposed to an aged systemic milieu upregulate VCAM1 (FIG. 3), and that VCAM1 inhibits stem cell proliferation and SVZ neurogenesis (Kokovay et al., Ibid.), we tested the hypothesis that the aged systemic milieu inhibits adult neurogenesis and induces brain inflammation through VCAM1.

Because aged mouse plasma is very difficult to obtain in large quantities required for chronic treatment studies we used a new model in which aged human plasma was injected into young (2-3 month old) NOD-scid IL2Rg$^{null}$ (NSG) immunodeficient mice. While NSG mice lack T and B lymphocytes and natural killer cells are defective, other leukocytes and innate immunity in general are intact. With the goal of developing a model of systemic aging in young animals, 3-month old NSG mice received aged human plasma (greater than 65 years) or PBS control injections every 3 days over the course of 3 weeks, with a total of 7 injections (i.v. retroorbital). To assess adult neurogenesis, the mice were pulsed with EdU and BrdU (FIG. 5A). Interestingly, there was a 30-50% decrease in proliferating BrdU+ and EdU+ cells in the dentate gyrus as assessed by immunofluorescence staining of perfused tissue sections followed by quantification in serial brain sections throughout the hippocampus (FIG. 5B-E). There was also a 25% decrease in DCX+ immature neurons. Considering VCAM1 was shown to inhibit neural precursor proliferation in the SVZ (Kokovay et al., Ibid.), we assessed the level of hippocampal neurogenesis by quantifying co and triple immunolabeled neural precursor cell populations. Quantification of neurogenesis in the SGZ revealed over 25% decreases in BrdU+Sox2+ proliferating progenitor cells, BrdU+Sox2+GFAP positive type I neural stem cells, and DCX+EdU+ immature neurons (FIG. 5B-E). Interestingly, this correlated with a 3-fold increase in VCAM1 expression in the hippocampus of young mice that received aged human plasma as compared with control PBS injected young mice (FIG. 5F-G).

Considering there is an increase in inflammatory cytokine expression in aged mouse and human plasma and an increase in overall systemic inflammation as demonstrated by increased B2M expression, a component of MHC I molecules (Smith et al., "B2-Microglobulin Is a Systemic Pro-Aging Factor That Impairs Cognitive Function and Neurogenesis," Nat. Med. (2015) 1-8. doi:10.1038/ nm.3898; Villeda et al., Ibid.), we next wanted to determine if aged plasma injections systemically into young mice would induce brain inflammation. Iba1+ microglia, the resident immune cells of the brain, adopt a more pro-inflammatory phenotype with aging, with increased expression of the lysosomal marker CD68[33]. To assess whether aged plasma injections into young mice affect brain inflammation, immunofluorescence staining of serial brain hippocampal tissue sections and quantification of reactive microglia was performed. While there was no significant difference in the percent area of Iba1+ microglia (FIG. 5H-I), there was a two-fold increase in CD68+Iba1+ reactive microglia (FIG. 5H, J-K). This demonstrates that intermittent (every 3$^{rd}$ day) aged plasma injections over a 3 week period is sufficient to induce mild brain inflammation as demonstrated by the increase in microglial activation, similar to the mild increase in brain inflammation seen in normal aging[33].

We next wanted to determine if administering the same amount of plasma, but over a shorter time period would have similar inhibitory effects on neurogenesis and brain inflammation. Young NSG mice were given aged human plasma injections twice daily for 3 consecutive days, followed by a 7$^{th}$ injection 4 hours before perfusion on day 4 (FIG. 6A). To assess the level of neural precursor cell proliferation in this acute injection scheme, the mice were pulsed with EdU 16 hours and 4 hours before perfusion (FIG. 6A). Interestingly, there was a 30% decrease in proliferating EdU+ cells and EdU+Sox2+ neural progenitor cells in the dentate gyrus as assessed by immunofluorescence staining of perfused tissue sections followed by quantification in serial brain sections throughout the hippocampus (FIG. 6B-D). Interestingly, this correlated with a significant increase in VCAM1 expression in the hippocampus of young mice that received acute aged human plasma injections over the course of 4 days as compared with control PBS injected young mice. We observed a 4-fold increase in percent area staining of VCAM1 and a two-fold increase in integrated density of immunofluorescently stained hippocampal sections (FIG. 6E-G). VCAM1 was also increased in the cortex of these mice (FIG. 9F-G). Strikingly, there was a significant increase in brain inflammation, as assessed by a two-fold increase in Iba1+ microglial percent area staining, and a three-fold increase in CD68+Iba1+ reactive microglia (FIG. 6H-K).

In conclusion, these data demonstrate that injections of aged human plasma can mimic the effects of systemic aging by inducing young brain deterioration.

F. Neutralizing Monoclonal VCAM1 Antibody Prevents Inhibitory Effects of Aged Human Plasma on Hippocampal Neurogenesis and Promotes Microglial Proliferation while Preventing Activation/Inflammation Considering VCAM1 increases with aging and in young mice exposed to an aged systemic milieu (FIG. 3), that young mice exposed to aged plasma display hallmarks of brain aging (FIGS. 5-6), including inhibited neurogenesis and increased brain inflammation, and that VCAM1 is required for inhibiting proliferation and maintaining a quiescent stem cell population in the SVZ, the other neurogenic region of the adult brain (Kokovay et al., Ibid.), we sought to assess whether BEC-specific upregulation of VCAM1 by the aged systemic milieu serves as a mediator of peripheral-parenchymal crosstalk and brain inhibitions by an inflammatory systemic environment.

To assess the functional role of increased VCAM1 on brain endothelium, young NSG mice received aged human plasma injections over the course of 3 weeks, along with i.p. injections of a neutralizing monoclonal antibody targeting VCAM1 (12 mg/kg) or IgG isotype control every 3$^{rd}$ day for a total of 7 plasma and antibody injections, similar to previous systemic antibody neutralization studies targeting brain endothelial adhesion molecules or integrins ((Zenaro et al., "Neutrophils promote Alzheimer's disease-like pathology and cognitive decline via LFA-1 integrin," Nat. Med (2015)), FIG. 7A). A different cohort of young NSG mice also received PBS injections, and all mice received multiple EdU and BrdU pulses in order to label neuronal precursor populations (FIG. 7A). Plasma collected from mice 1 day and 3 days after receiving a single VCAM1 monoclonal antibody injection was used to stain LPS-treated lymph node sections followed by isotype matched secondary antibody staining. This confirmed that there was still saturated antibody in systemic circulation even 3 days after injection (FIG. 7B).

Aged human plasma treated NSG mice had decreased BrdU+Sox2+ neural progenitor cell proliferation, comparable to what our lab reported in young wild type (C57Bl6/J) mice treated with aged mouse plasma ((Villeda et al., Ibid.), FIG. 7C-D). Excitingly, neurogenesis was rescued in young NSG mice that received aged plasma concurrently with neutralizing monoclonal VCAM1 antibody, as shown by BrdU+Sox2+ cell numbers comparable to PBS injected control mice and greater than mice that received aged human plasma along with isotype control IgG antibody (FIG. 7C-D). VCAM1 levels were confirmed to increase in lectin+ brain vasculature of aged plasma injected mice, regardless of antibody or isotype control injections, although the trend was not significant in VCAM1 antibody injected mice (FIG. 7E-F). To determine whether brain inflammation induced by systemic aged plasma injections could be prevented with monoclonal VCAM1 antibody neutralization, microglial reactivity was measured via immunofluorescence staining (FIG. 8A). Surprisingly, VCAM1 systemic antibody treatment significantly increased Iba1+ microglial expression from average of 7% to 15% area staining (FIG. 8B), although the majority of these microglia are not CD68+, as shown by a decrease in CD68% percent area staining in VCAM1 antibody treated mice (FIG. 8C), and only a small percentage (1-2%) increase in CD68+Iba1+ colabeled microglia in VCAM1 antibody treated mice (FIG. 8D). This indicates that VCAM1 monoclonal antibody neutralization rescues aged plasma-induced decline of hippocampal neurogenesis and promotes non-reactive, non-inflammatory microglial expansion.

To determine whether VCAM1 is required for the detrimental effects of an aged systemic milieu on hippocampal neurogenesis and brain inflammation we administered a neutralizing VCAM1 antibody (9 mg/kg i.p.), or an IgG isotype control, systemically into aged (16 month old) C57BL6/J mice every 3$^{rd}$ day for a total of 7 antibody injections, over the course of 3 weeks (FIG. 11A). A similar VCAM1 neutralization protocol was used previously to ameliorate epileptic seizures in a mouse model (Fabene, et al., Nat. Med. (2008) 14:1377-83). Additionally, VCAM1 inhibits stem cell proliferation and SVZ neurogenesis (Kokovay et al., Cell Stem Cell (2012) 11:220-30). Mice were pulsed with BrdU daily for the last 6 days prior to perfusion in order to assess proliferating neural precursor populations. Quantification of neurogenesis in the SGZ revealed a general increase in BrdU+ proliferating cells, with a two-fold increase in proliferating BrdU+Sox2+ neural precursor cells in mice which received monoclonal antibody targeting VCAM1 (FIG. 11B-D). We also observed a significant reduction in microglial reactivity, close to levels seen in young mice (FIG. 11E-G).

We next determined whether VCAM1 neutralization would prevent the brain inhibitory effects of aged human plasma administration. Young (3 month old) NSG mice were given retro-orbital injections of aged human plasma (greater than 65 years) along with neutralizing monoclonal antibody targeting VCAM1 one day before beginning injections (day 0) and along with the 5$^{th}$ plasma injection on day 3 (FIG. 12A). Another cohort of young NSG mice received PBS injections along with IgG and VCAM1 mAb. To assess the level of neural precursor cell proliferation, the mice were pulsed with EdU 16 hours and 3 hours before perfusion. Aged human plasma inhibited proliferation of EdU+ cells and EdU+Sox2+ neural progenitor cells by about 30% (FIG. 12B-D). This inhibition was rescued by antibody treatment as shown by the return of proliferation levels to those seen in PBS injected control mice given either VCAM1 antibody or IgG. Importantly, monoclonal antibody treatment did not enhance neurogenesis in PBS treated controls, confirming that the rescue in neurogenesis was due to neutralization of aged plasma signaling, and not just to antibody treatment in healthy young mice under conditions of homeostasis.

There was a significant increase in Iba1+ microglial staining and CD68+ reactive microglia in the hippocampi of aged human plasma treated NSG mice as compared to controls, while VCAM1 systemic antibody treatment prevented the increase in reactive microglia (FIG. 12E-G). VCAM1 expression in lectin+ brain endothelium was twofold higher in mice that received aged human plasma and unaffected by antibody neutralization (FIG. 12H-I).

G. Transgenic BEC-Specific Deletion of VCAM1 in Young Mice Prevents the Inhibitory Effects of Aged Plasma on Hippocampal Neurogenesis and Microglial Activation Brain endothelial and epithelial cells are essential components of the BBB and blood cerebrospinal fluid barrier (BCSFB). As such, they are directly exposed to pro-aging factors and pro-inflammatory mediators, and therefore may drive the brain aging phenotypes induced by an aged systemic milieu.

To test our hypothesis that brain endothelial VCAM1 mediates the pro-inflammatory and inhibitory effects of aged plasma in the brain, we targeted Vcam1 specifically in BECs using Slco1c1-Cre$^{ERT2}$ reporter mice—carrying inducible Cre under a brain endothelial and epithelial-specific promoter. Brain endothelial and epithelial cells were shown to be important mediators of immune-brain communication under systemic inflammation (Ridder et al., J. Exp. Med. (2011) 208: 2615-23). These mice were recently used to demonstrate that interferon signaling through BECs mediates the cognitive impairments induced by viral infection (Blank et al., Immunity (2016) 44:901-912).

To investigate if VCAM1 deletion specifically in brain endothelial and epithelial cells prevents the inhibitory effects of the aged systemic milieu, young (3 month old) Vcam1$^{fl/fl}$Slco1c1-Cre$^{ERT2}$ mice were injected with tamoxifen (i.p.) for 4 consecutive days, followed by 3 days of rest. Young or aged mouse plasma was then administered for 4 days along with BrdU to label neural precursor populations according to the acute injection paradigm established in this study (FIG. 13A). Cre$^-$ mice that received aged mouse plasma as compared to young mouse plasma upregulated expression of BEC specific VCAM1, consistent with previous results in wildtype mice, while there was no detection of BEC-specific VCAM1 expression in Cre$^+$ mice regardless of plasma treatment (FIG. 13B-C). Furthermore, sVCAM1 remained high in the plasma of all tamoxifen treated Cre$^+$ and Cre$^-$ mice and was not reduced by brain endothelial and epithelial-specific deletion, as measured by ELISA (FIG. 13D).

Quantification of neurogenesis in the SGZ revealed significant decreases in total proliferating BrdU+ cells, co-labeled BrdU+Sox2+ neural precursor cells, and DCX+ immature neurons in the dentate gyri of Cre$^-$ mice treated with aged plasma as compared to Cre$^-$ mice treated with young plasma, confirming earlier results in wildtype mice (FIG. 13E-I). Unexpectedly, brain endothelial and epithelial-specific deletion of VCAM1 in Cre$^+$ mice caused a decrease in neurogenesis, regardless of young or aged plasma treatment, as compared to Cre$^-$ mice treated with young mouse plasma. Importantly, BEC-specific deletion of Vcam1 in Cre$^+$ mice prevented the inhibition of neural precursor cell populations by aged plasma administration (FIG. 13E-I). Additionally, BEC-specific deletion of Vcam1 in Cre$^+$ mice prevented Iba1+CD68+ microglial activation by aged plasma (FIG. 13J-L).

These data collectively demonstrate that a pro-inflammatory aged systemic milieu signals directly through an activated brain endothelium to inhibit hippocampal neurogenesis and induce microglial reactivity, specific phenotypes of brain aging. This peripheral-parenchymal crosstalk is mediated by VCAM1 signaling, which increases both systemically and locally on brain endothelium with normal aging and in experimental models of systemic aging.

H. VLA-4 mAb Reduces Microglial Activation in Aged Mice

Preventing leukocyte binding to activated endothelium with a systemic neutralizing antibody against VCAM-1 rejuvenated aged brains and prevented the pro-aging effects of an old systemic milieu. Leukocytes bind VCAM-1 primarily through alpha4beta1, also known as VLA-4 (Ballantyne and Entman, Circulation (2002) 106:766-767; Rose et al., Blood (2002) 15:602-609; Tudor et al., Cytokine (2001) 15:196-211). VLA-4 is expressed on myeloid cells and T lymphocytes. Immunodeficient NSG mice, which lack adaptive immunity but retain the myeloid cells of the innate immune system, including neutrophils and monocytes, display brain aging phenotypes when exposed to aged human plasma, including activation of the cerebrovasculature and microglia. This indicates that innate immune cells drive the inhibitory response of an aged systemic milieu. In support of this, neutrophils have recently been shown to be major players in the pathological progression of AD (Zenaro et al., Nat. Mad. (2015) 8:880-886).

Aged mice received i.p. injections of a monoclonal antibody targeting VLA-4 (FIG. 14A). This led to a significant reduction on reactive microglia in aged brains, close to levels seen in the young (FIG. 14B-E). VCAM-1 expression levels were not affected (FIG. 14F-G).

II. Discussion

Whether VCAM1 plays a significant role in the normal aging of the CNS, and if targeting it could ameliorate brain deterioration by the aged systemic milieu has not been answered until now. The above results demonstrate that aged plasma-induced cerebrovascular inflammation, as assessed by BEC activation and VCAM1 upregulation, is a crucial mediator of peripheral-parenchymal crosstalk and brain aging, as shown by measuring neurogenesis and brain inflammation, two hallmarks of brain aging.

In this study, we define a mechanism by which peripheral inhibitory signaling by the aged systemic milieu to the brain parenchyma is mediated through activation of brain endothelium. Specifically, aged plasma can inhibit neurogenesis and induce brain inflammation in part by upregulation and signaling through VCAM1 on BECs.

Our study elucidates a previously unrecognized role for brain endothelial VCAM1 in the progression of age-related impairments in both inflammatory and regenerative processes in the brain. Here, we show that VCAM1 expression is regulated by a pro-inflammatory aging systemic milieu and mediates the inhibitory effects of an aging environment on hippocampal neurogenesis and microglial activation. By studying normal aging and using several systemic aging models, including heterochronic parabiosis, mouse-to-mouse plasma injections and human-to-mouse plasma injections, we demonstrate that pro-aging factors in an inhibitory milieu activate brain endothelium through VCAM1 upregulation which then signals to the brain parenchyma to drive aging phenotypes. Both systemic antibody neutralization studies and brain endothelial and epithelial-specific deletion of VCAM1 prevented the negative effects of an aged environment. However, transgenic deletion of VCAM1 resulted in lower baseline neurogenesis. While VCAM1 signaling on activated brain endothelium may be detrimental to brain function, it is possible that lower levels are necessary to maintain homeostasis. In support of this, it was shown that long-term blockade of VCAM1 signaling reduced SVZ neurogenesis (Kokovay et al., 2012).

Pro-inflammatory factors that are responsible for activating brain endothelium and up-regulating VCAM1 may be targeted in therapeutic regiments. Such factors include, but are not limited to: TNF-α, IL-1β, IL-4, IFN-γ and various interleukins. Also of interest are non-cytokine factors that regulate VCAM1, including microRNAs. In some instances, a combination of such factors and regulatory molecules may be targeted in order to counter VCAM1 induction with age. Targeting the crosstalk between blood-borne factors and the vasculature may therefore be a potent mechanism to counter multiple inhibitory signals.

Here we show that VCAM1 expression is regulated by the aging systemic milieu and mediates the inhibitory peripheral effects on hippocampal neurogenesis and neuroinflammation. We discovered that VCAM1 plays a significant role in the normal aging of the CNS, and targeting it ameliorates brain deterioration by the aged systemic milieu. Lastly, VCAM1 is regulated post-translationally through ADAM17 (also known as TACE) metalloproteinase, which acts as an ectodomain sheddase to cleave VCAM1 into the blood, resulting in a soluble form of VCAM1 which can be detected in plasma and cell supernatants. Here we show that ADAM17 activity declines with age, further explaining the increase in membrane VCAM1 expression on BECs. Together, these results elucidate the molecular mechanism for increased brain inflammation and susceptibility to neurodegeneration through upregulation of BEC VCAM1

The above results show that blocking of VCAM1, via a neutralizing monoclonal antibody, reduces neuroinflammation and increases neurogenesis. As such, neutralizing VCAM1 or increasing VCAM1 shedding into the blood can prevent age-associated brain inflammation, neurodegeneration and cognitive decline.

In this study, we define a mechanism by which peripheral inhibitory signaling by the aged systemic milieu to the brain parenchyma is mediated through activation of brain endothelium. Specifically, aged plasma can inhibit neurogenesis and induce brain inflammation in part by upregulation and signaling through VCAM1 on BECs.

Our study sheds insight into how changes on the luminal side of vasculature can affect the brain parenchyma. Preventing leukocyte binding to activated endothelium with a systemic neutralizing antibody rejuvenated aged brains and prevented the pro-aging effects of an old systemic milieu. Leukocytes bind VCAM-1 primarily through alpha4beta1, also known as VLA-4 (Ballantyne and Entman, 2002; Rose et al., 2000; Tudor et al., 2001). VLA-4 is expressed on myeloid cells and T lymphocytes. Immunodeficient NSG mice, which lack adaptive immunity but retain the myeloid cells of the innate immune system, including neutrophils and monocytes, display brain aging phenotypes when exposed to aged human plasma, including activation of the cerebrovasculature and microglia. This would suggest that innate immune cells may drive the inhibitory response of an aged systemic milieu. In support of this, neutrophils have recently been shown to be major players in the pathological progression of AD (Zenaro, Pietronigro et al. 2015). The BBB provides an essential source of nutrients to the brain parenchyma in a highly regulated manner through specific transport systems, protection from xenobiotics and external pathogens, and acts as an important chemical messaging system between the CNS and the PNS through cytokine and neuropeptide signaling to regulate neurogenesis, cognitive functioning, and immune cell reactivity in response to external stimulus. The BBB serves as a crucial barrier to the systemic milieu in order to maintain brain homeostasis, and is impermeable to most macromolecules due to unique tight and adherens junctions between BECs, the major BBB component which is supported structurally by pericytes located within the basement membrane of blood vessels. BBB permeability and cytokine signaling have been shown to be disrupted in multiple disorders of the CNS, during fever-inducing illnesses and during normal aging. While a tight BBB is crucial for maintaining brain homeostasis, crossing the BBB remains the greatest obstacle to therapeutic interventions for treatments of age induced neurodegeneration and cognitive decline. The ability, therefore to modulate brain function through the systemic milieu holds great potential for combating neurodegeneration and cognitive decline. Specifically, elucidating the mechanisms by which aged systemic factors inhibit brain function at the BBB will help unshed noninvasive mechanisms by which we can therapeutically enhance cognitive function and prevent vascular degeneration in the elderly.

In summary, our data provide mechanistic insights into how changes in the systemic environment with aging drive impairments in the aged brain parenchyma through crosstalk with an inflamed vasculature. From a translational perspective, our data raise the possibility that the inflammatory and regenerative dysfunction induced by aging could be ameliorated through noninvasive, systemic modulation of VCAM1 at the BBB.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of the present invention is embodied by the appended claims.

That which is claimed is:

1. A method of treating a disorder or disease in an adult mammal, the method comprising:
   administering a neutralizing vascular cell adhesion molecule 1 (VCAM-1) antibody or binding fragment thereof to an adult mammal who has a disorder or disease selected from the group consisting of: Alzheimer's disease, Parkinson's disease, frontotemporal dementia, Huntington's disease, and amyotrophic lateral sclerosis,
   wherein said administering results in treatment of the disorder or disease.

2. The method according to claim 1, wherein the mammal is a human.

3. The method according to claim 1, wherein the adult mammal is an elderly mammal.

4. The method according to claim 1, wherein said method comprises measuring cognitive ability of the adult mammal before and after said administering.

5. A method of stimulating neurogenesis and/or blocking neurodegeneration in an adult mammal, the method comprising:
   administering a neutralizing vascular cell adhesion molecule 1 (VCAM-1) antibody or binding fragment thereof to an adult mammal who has Parkinson's disease, frontotemporal dementia, Huntington's disease, or amyotrophic lateral sclerosis, and after said administering,
   measuring neurogenesis and/or microglial reactivity in the adult mammal.

6. The method according to claim 5, further comprising measuring cognitive ability of the adult mammal after said administering.

7. The method according to claim 5, wherein the mammal is a human.

8. The method according to claim 5, wherein the adult mammal is an elderly mammal.

9. The method according to claim 8, wherein the elderly mammal is an elderly human.

10. A method of treating a disorder or disease in an adult mammal, the method comprising:
    administering a neutralizing vascular cell adhesion molecule 1 (VCAM-1) antibody or binding fragment thereof to an adult mammal who has a disorder or disease selected from the group consisting of: Parkinson's disease, frontotemporal dementia, Huntington's disease, and amyotrophic lateral sclerosis,
    wherein said administering results in treatment of the disorder or disease.

11. The method according to claim 10, further comprising measuring cognitive ability of the adult mammal after said administering.

12. The method according to claim 10, further comprising measuring neurogenesis and/or microglial reactivity in the adult mammal after said administering.

13. The method according to claim 10, wherein the mammal is a human.

14. The method according to claim 10, wherein the adult mammal is an elderly mammal.

15. The method according to claim 14, wherein the elderly mammal is an elderly human.

* * * * *

SEQUENCE LISTING

```
<160> NUMBER OF SEQ ID NOS: 4

<210> SEQ ID NO 1
<211> LENGTH: 739
<212> TYPE: PRT
<213> ORGANISM: Homo sapiens
```

```
<400> SEQUENCE: 1

Met Pro Gly Lys Met Val Val Ile Leu Gly Ala Ser Asn Ile Leu Trp
1               5                   10                  15

Ile Met Phe Ala Ala Ser Gln Ala Phe Lys Ile Glu Thr Thr Pro Glu
                20                  25                  30

Ser Arg Tyr Leu Ala Gln Ile Gly Asp Ser Val Ser Leu Thr Cys Ser
            35                  40                  45

Thr Thr Gly Cys Glu Ser Pro Phe Phe Ser Trp Arg Thr Gln Ile Asp
        50                  55                  60

Ser Pro Leu Asn Gly Lys Val Thr Asn Glu Gly Thr Thr Ser Thr Leu
65                  70                  75                  80

Thr Met Asn Pro Val Ser Phe Gly Asn Glu His Ser Tyr Leu Cys Thr
                85                  90                  95

Ala Thr Cys Glu Ser Arg Lys Leu Glu Lys Gly Ile Gln Val Glu Ile
            100                 105                 110

Tyr Ser Phe Pro Lys Asp Pro Glu Ile His Leu Ser Gly Pro Leu Glu
        115                 120                 125

Ala Gly Lys Pro Ile Thr Val Lys Cys Ser Val Ala Asp Val Tyr Pro
130                 135                 140

Phe Asp Arg Leu Glu Ile Asp Leu Leu Lys Gly Asp His Leu Met Lys
145                 150                 155                 160

Ser Gln Glu Phe Leu Glu Asp Ala Asp Arg Lys Ser Leu Glu Thr Lys
                165                 170                 175

Ser Leu Glu Val Thr Phe Thr Pro Val Ile Glu Asp Ile Gly Lys Val
            180                 185                 190

Leu Val Cys Arg Ala Lys Leu His Ile Asp Glu Met Asp Ser Val Pro
        195                 200                 205

Thr Val Arg Gln Ala Val Lys Glu Leu Gln Val Tyr Ile Ser Pro Lys
    210                 215                 220

Asn Thr Val Ile Ser Val Asn Pro Ser Thr Lys Leu Gln Glu Gly Gly
225                 230                 235                 240

Ser Val Thr Met Thr Cys Ser Ser Glu Gly Leu Pro Ala Pro Glu Ile
                245                 250                 255

Phe Trp Ser Lys Lys Leu Asp Asn Gly Asn Leu Gln His Leu Ser Gly
            260                 265                 270

Asn Ala Thr Leu Thr Leu Ile Ala Met Arg Met Glu Asp Ser Gly Ile
        275                 280                 285

Tyr Val Cys Glu Gly Val Asn Leu Ile Gly Lys Asn Arg Lys Glu Val
    290                 295                 300

Glu Leu Ile Val Gln Glu Lys Pro Phe Thr Val Glu Ile Ser Pro Gly
305                 310                 315                 320

Pro Arg Ile Ala Ala Gln Ile Gly Asp Ser Val Met Leu Thr Cys Ser
                325                 330                 335

Val Met Gly Cys Glu Ser Pro Ser Phe Ser Trp Arg Thr Gln Ile Asp
            340                 345                 350

Ser Pro Leu Ser Gly Lys Val Arg Ser Glu Gly Thr Asn Ser Thr Leu
        355                 360                 365

Thr Leu Ser Pro Val Ser Phe Glu Asn Glu His Ser Tyr Leu Cys Thr
    370                 375                 380

Val Thr Cys Gly His Lys Lys Leu Glu Lys Gly Ile Gln Val Glu Leu
385                 390                 395                 400

Tyr Ser Phe Pro Arg Asp Pro Glu Ile Glu Met Ser Gly Gly Leu Val
                405                 410                 415
```

```
Asn Gly Ser Ser Val Thr Val Ser Cys Lys Val Pro Ser Val Tyr Pro
                420                 425                 430

Leu Asp Arg Leu Glu Ile Glu Leu Leu Lys Gly Glu Thr Ile Leu Glu
        435                 440                 445

Asn Ile Glu Phe Leu Glu Asp Thr Asp Met Lys Ser Leu Glu Asn Lys
    450                 455                 460

Ser Leu Glu Met Thr Phe Ile Pro Thr Ile Glu Asp Thr Gly Lys Ala
465                 470                 475                 480

Leu Val Cys Gln Ala Lys Leu His Ile Asp Asp Met Glu Phe Glu Pro
                485                 490                 495

Lys Gln Arg Gln Ser Thr Gln Thr Leu Tyr Val Asn Val Ala Pro Arg
            500                 505                 510

Asp Thr Thr Val Leu Val Ser Pro Ser Ser Ile Leu Glu Glu Gly Ser
        515                 520                 525

Ser Val Asn Met Thr Cys Leu Ser Gln Gly Phe Pro Ala Pro Lys Ile
    530                 535                 540

Leu Trp Ser Arg Gln Leu Pro Asn Gly Glu Leu Gln Pro Leu Ser Glu
545                 550                 555                 560

Asn Ala Thr Leu Thr Leu Ile Ser Thr Lys Met Glu Asp Ser Gly Val
                565                 570                 575

Tyr Leu Cys Glu Gly Ile Asn Gln Ala Gly Arg Ser Arg Lys Glu Val
            580                 585                 590

Glu Leu Ile Ile Gln Val Thr Pro Lys Asp Ile Lys Leu Thr Ala Phe
        595                 600                 605

Pro Ser Glu Ser Val Lys Glu Gly Asp Thr Val Ile Ile Ser Cys Thr
    610                 615                 620

Cys Gly Asn Val Pro Glu Thr Trp Ile Ile Leu Lys Lys Lys Ala Glu
625                 630                 635                 640

Thr Gly Asp Thr Val Leu Lys Ser Ile Asp Gly Ala Tyr Thr Ile Arg
                645                 650                 655

Lys Ala Gln Leu Lys Asp Ala Gly Val Tyr Glu Cys Glu Ser Lys Asn
            660                 665                 670

Lys Val Gly Ser Gln Leu Arg Ser Leu Thr Leu Asp Val Gln Gly Arg
        675                 680                 685

Glu Asn Asn Lys Asp Tyr Phe Ser Pro Glu Leu Leu Val Leu Tyr Phe
    690                 695                 700

Ala Ser Ser Leu Ile Ile Pro Ala Ile Gly Met Ile Ile Tyr Phe Ala
705                 710                 715                 720

Arg Lys Ala Asn Met Lys Gly Ser Tyr Ser Leu Val Glu Ala Gln Lys
                725                 730                 735

Ser Lys Val

<210> SEQ ID NO 2
<211> LENGTH: 824
<212> TYPE: PRT
<213> ORGANISM: Homo sapiens

<400> SEQUENCE: 2

Met Arg Gln Ser Leu Leu Phe Leu Thr Ser Val Val Pro Phe Val Leu
1               5                   10                  15

Ala Pro Arg Pro Pro Asp Asp Pro Gly Phe Gly Pro His Gln Arg Leu
            20                  25                  30

Glu Lys Leu Asp Ser Leu Leu Ser Asp Tyr Asp Ile Leu Ser Leu Ser
        35                  40                  45
```

```
Asn Ile Gln Gln His Ser Val Arg Lys Arg Asp Leu Gln Thr Ser Thr
 50                  55                  60

His Val Glu Thr Leu Leu Thr Phe Ser Ala Leu Lys Arg His Phe Lys
 65                  70                  75                  80

Leu Tyr Leu Thr Ser Ser Thr Glu Arg Phe Ser Gln Asn Phe Lys Val
                 85                  90                  95

Val Val Val Asp Gly Lys Asn Glu Ser Glu Tyr Thr Val Lys Trp Gln
            100                 105                 110

Asp Phe Phe Thr Gly His Val Gly Glu Pro Asp Ser Arg Val Leu
            115                 120                 125

Ala His Ile Arg Asp Asp Val Ile Ile Arg Ile Asn Thr Asp Gly
130                 135                 140

Ala Glu Tyr Asn Ile Glu Pro Leu Trp Arg Phe Val Asn Asp Thr Lys
145                 150                 155                 160

Asp Lys Arg Met Leu Val Tyr Lys Ser Glu Asp Ile Lys Asn Val Ser
                165                 170                 175

Arg Leu Gln Ser Pro Lys Val Cys Gly Tyr Leu Lys Val Asp Asn Glu
            180                 185                 190

Glu Leu Leu Pro Lys Gly Leu Val Asp Arg Glu Pro Pro Glu Glu Leu
            195                 200                 205

Val His Arg Val Lys Arg Ala Asp Pro Asp Pro Met Lys Asn Thr
210                 215                 220

Cys Lys Leu Leu Val Val Ala Asp His Arg Phe Tyr Arg Tyr Met Gly
225                 230                 235                 240

Arg Gly Glu Glu Ser Thr Thr Thr Asn Tyr Leu Ile Glu Leu Ile Asp
                245                 250                 255

Arg Val Asp Asp Ile Tyr Arg Asn Thr Ser Trp Asp Asn Ala Gly Phe
            260                 265                 270

Lys Gly Tyr Gly Ile Gln Ile Glu Gln Ile Arg Ile Leu Lys Ser Pro
            275                 280                 285

Gln Glu Val Lys Pro Gly Glu Lys His Tyr Asn Met Ala Lys Ser Tyr
290                 295                 300

Pro Asn Glu Glu Lys Asp Ala Trp Asp Val Lys Met Leu Leu Glu Gln
305                 310                 315                 320

Phe Ser Phe Asp Ile Ala Glu Glu Ala Ser Lys Val Cys Leu Ala His
                325                 330                 335

Leu Phe Thr Tyr Gln Asp Phe Asp Met Gly Thr Leu Gly Leu Ala Tyr
            340                 345                 350

Val Gly Ser Pro Arg Ala Asn Ser His Gly Gly Val Cys Pro Lys Ala
            355                 360                 365

Tyr Tyr Ser Pro Val Gly Lys Lys Asn Ile Tyr Leu Asn Ser Gly Leu
            370                 375                 380

Thr Ser Thr Lys Asn Tyr Gly Lys Thr Ile Leu Thr Lys Glu Ala Asp
385                 390                 395                 400

Leu Val Thr Thr His Glu Leu Gly His Asn Phe Gly Ala Glu His Asp
                405                 410                 415

Pro Asp Gly Leu Ala Glu Cys Ala Pro Asn Glu Asp Gln Gly Gly Lys
            420                 425                 430

Tyr Val Met Tyr Pro Ile Ala Val Ser Gly Asp His Glu Asn Asn Lys
            435                 440                 445

Met Phe Ser Asn Cys Ser Lys Gln Ser Ile Tyr Lys Thr Ile Glu Ser
450                 455                 460
```

```
Lys Ala Gln Glu Cys Phe Gln Glu Arg Ser Asn Lys Val Cys Gly Asn
465                 470                 475                 480

Ser Arg Val Asp Glu Gly Glu Cys Asp Pro Gly Ile Met Tyr Leu
            485                 490                 495

Asn Asn Asp Thr Cys Cys Asn Ser Asp Cys Thr Leu Lys Glu Gly Val
            500                 505                 510

Gln Cys Ser Asp Arg Asn Ser Pro Cys Cys Lys Asn Cys Gln Phe Glu
            515                 520                 525

Thr Ala Gln Lys Lys Cys Gln Glu Ala Ile Asn Ala Thr Cys Lys Gly
            530                 535                 540

Val Ser Tyr Cys Thr Gly Asn Ser Ser Glu Cys Pro Pro Pro Gly Asn
545                 550                 555                 560

Ala Glu Asp Asp Thr Val Cys Leu Asp Leu Gly Lys Cys Lys Asp Gly
                565                 570                 575

Lys Cys Ile Pro Phe Cys Glu Arg Glu Gln Gln Leu Glu Ser Cys Ala
            580                 585                 590

Cys Asn Glu Thr Asp Asn Ser Cys Lys Val Cys Cys Arg Asp Leu Ser
            595                 600                 605

Gly Arg Cys Val Pro Tyr Val Asp Ala Glu Gln Lys Asn Leu Phe Leu
610                 615                 620

Arg Lys Gly Lys Pro Cys Thr Val Gly Phe Cys Asp Met Asn Gly Lys
625                 630                 635                 640

Cys Glu Lys Arg Val Gln Asp Val Ile Glu Arg Phe Trp Asp Phe Ile
            645                 650                 655

Asp Gln Leu Ser Ile Asn Thr Phe Gly Lys Phe Leu Ala Asp Asn Ile
            660                 665                 670

Val Gly Ser Val Leu Val Phe Ser Leu Ile Phe Trp Ile Pro Phe Ser
            675                 680                 685

Ile Leu Val His Cys Val Asp Lys Lys Leu Asp Lys Gln Tyr Glu Ser
            690                 695                 700

Leu Ser Leu Phe His Pro Ser Asn Val Glu Met Leu Ser Ser Met Asp
705                 710                 715                 720

Ser Ala Ser Val Arg Ile Ile Lys Pro Phe Pro Ala Pro Gln Thr Pro
                725                 730                 735

Gly Arg Leu Gln Pro Ala Pro Val Ile Pro Ser Ala Pro Ala Ala Pro
            740                 745                 750

Lys Leu Asp His Gln Arg Met Asp Thr Ile Gln Glu Asp Pro Ser Thr
            755                 760                 765

Asp Ser His Met Asp Glu Asp Gly Phe Glu Lys Asp Pro Phe Pro Asn
            770                 775                 780

Ser Ser Thr Ala Ala Lys Ser Phe Glu Asp Leu Thr Asp His Pro Val
785                 790                 795                 800

Thr Arg Ser Glu Lys Ala Ala Ser Phe Lys Leu Gln Arg Gln Asn Arg
            805                 810                 815

Val Asp Ser Lys Glu Thr Glu Cys
            820

<210> SEQ ID NO 3
<211> LENGTH: 1032
<212> TYPE: PRT
<213> ORGANISM: Homo sapiens
```

<400> SEQUENCE: 3

```
Met Ala Trp Glu Ala Arg Arg Glu Pro Gly Pro Arg Arg Ala Ala Val
1               5                   10                  15

Arg Glu Thr Val Met Leu Leu Cys Leu Gly Val Pro Thr Gly Arg
            20                  25                  30

Pro Tyr Asn Val Asp Thr Glu Ser Ala Leu Leu Tyr Gln Gly Pro His
        35                  40                  45

Asn Thr Leu Phe Gly Tyr Ser Val Val Leu His Ser His Gly Ala Asn
    50                  55                  60

Arg Trp Leu Leu Val Gly Ala Pro Thr Ala Asn Trp Leu Ala Asn Ala
65                  70                  75                  80

Ser Val Ile Asn Pro Gly Ala Ile Tyr Arg Cys Arg Ile Gly Lys Asn
                85                  90                  95

Pro Gly Gln Thr Cys Glu Gln Leu Gln Leu Gly Ser Pro Asn Gly Glu
            100                 105                 110

Pro Cys Gly Lys Thr Cys Leu Glu Glu Arg Asp Asn Gln Trp Leu Gly
        115                 120                 125

Val Thr Leu Ser Arg Gln Pro Gly Glu Asn Gly Ser Ile Val Thr Cys
    130                 135                 140

Gly His Arg Trp Lys Asn Ile Phe Tyr Ile Lys Asn Glu Asn Lys Leu
145                 150                 155                 160

Pro Thr Gly Gly Cys Tyr Gly Val Pro Pro Asp Leu Arg Thr Glu Leu
                165                 170                 175

Ser Lys Arg Ile Ala Pro Cys Tyr Gln Asp Tyr Val Lys Lys Phe Gly
            180                 185                 190

Glu Asn Phe Ala Ser Cys Gln Ala Gly Ile Ser Ser Phe Tyr Thr Lys
        195                 200                 205

Asp Leu Ile Val Met Gly Ala Pro Gly Ser Ser Tyr Trp Thr Gly Ser
    210                 215                 220

Leu Phe Val Tyr Asn Ile Thr Thr Asn Lys Tyr Lys Ala Phe Leu Asp
225                 230                 235                 240

Lys Gln Asn Gln Val Lys Phe Gly Ser Tyr Leu Gly Tyr Ser Val Gly
                245                 250                 255

Ala Gly His Phe Arg Ser Gln His Thr Thr Glu Val Val Gly Gly Ala
            260                 265                 270

Pro Gln His Glu Gln Ile Gly Lys Ala Tyr Ile Phe Ser Ile Asp Glu
        275                 280                 285

Lys Glu Leu Asn Ile Leu His Glu Met Lys Gly Lys Lys Leu Gly Ser
    290                 295                 300

Tyr Phe Gly Ala Ser Val Cys Ala Val Asp Leu Asn Ala Asp Gly Phe
305                 310                 315                 320

Ser Asp Leu Leu Val Gly Ala Pro Met Gln Ser Thr Ile Arg Glu Glu
                325                 330                 335

Gly Arg Val Phe Val Tyr Ile Asn Ser Gly Ser Gly Ala Val Met Asn
            340                 345                 350

Ala Met Glu Thr Asn Leu Val Gly Ser Asp Lys Tyr Ala Ala Arg Phe
        355                 360                 365

Gly Glu Ser Ile Val Asn Leu Gly Asp Ile Asp Asn Asp Gly Phe Glu
    370                 375                 380

Asp Val Ala Ile Gly Ala Pro Gln Glu Asp Asp Leu Gln Gly Ala Ile
385                 390                 395                 400

Tyr Ile Tyr Asn Gly Arg Ala Asp Gly Ile Ser Ser Thr Phe Ser Gln
                405                 410                 415
```

Arg Ile Glu Gly Leu Gln Ile Ser Lys Ser Leu Ser Met Phe Gly Gln
                420                 425                 430

Ser Ile Ser Gly Gln Ile Asp Ala Asp Asn Asn Gly Tyr Val Asp Val
            435                 440                 445

Ala Val Gly Ala Phe Arg Ser Asp Ser Ala Val Leu Leu Arg Thr Arg
        450                 455                 460

Pro Val Ile Val Asp Ala Ser Leu Ser His Pro Glu Ser Val Asn
465                 470                 475                 480

Arg Thr Lys Phe Asp Cys Val Glu Asn Gly Trp Pro Ser Val Cys Ile
                485                 490                 495

Asp Leu Thr Leu Cys Phe Ser Tyr Lys Gly Lys Glu Val Pro Gly Tyr
            500                 505                 510

Ile Val Leu Phe Tyr Asn Met Ser Leu Asp Val Asn Arg Lys Ala Glu
        515                 520                 525

Ser Pro Pro Arg Phe Tyr Phe Ser Ser Asn Gly Thr Ser Asp Val Ile
    530                 535                 540

Thr Gly Ser Ile Gln Val Ser Ser Arg Glu Ala Asn Cys Arg Thr His
545                 550                 555                 560

Gln Ala Phe Met Arg Lys Asp Val Arg Asp Ile Leu Thr Pro Ile Gln
                565                 570                 575

Ile Glu Ala Ala Tyr His Leu Gly Pro His Val Ile Ser Lys Arg Ser
            580                 585                 590

Thr Glu Glu Phe Pro Pro Leu Gln Pro Ile Leu Gln Gln Lys Lys Glu
        595                 600                 605

Lys Asp Ile Met Lys Lys Thr Ile Asn Phe Ala Arg Phe Cys Ala His
    610                 615                 620

Glu Asn Cys Ser Ala Asp Leu Gln Val Ser Ala Lys Ile Gly Phe Leu
625                 630                 635                 640

Lys Pro His Glu Asn Lys Thr Tyr Leu Ala Val Gly Ser Met Lys Thr
                645                 650                 655

Leu Met Leu Asn Val Ser Leu Phe Asn Ala Gly Asp Asp Ala Tyr Glu
            660                 665                 670

Thr Thr Leu His Val Lys Leu Pro Val Gly Leu Tyr Phe Ile Lys Ile
        675                 680                 685

Leu Glu Leu Glu Glu Lys Gln Ile Asn Cys Glu Val Thr Asp Asn Ser
    690                 695                 700

Gly Val Val Gln Leu Asp Cys Ser Ile Gly Tyr Ile Tyr Val Asp His
705                 710                 715                 720

Leu Ser Arg Ile Asp Ile Ser Phe Leu Leu Asp Val Ser Ser Leu Ser
                725                 730                 735

Arg Ala Glu Glu Asp Leu Ser Ile Thr Val His Ala Thr Cys Glu Asn
            740                 745                 750

Glu Glu Glu Met Asp Asn Leu Lys His Ser Arg Val Thr Val Ala Ile
        755                 760                 765

Pro Leu Lys Tyr Glu Val Lys Leu Thr Val His Gly Phe Val Asn Pro
    770                 775                 780

Thr Ser Phe Val Tyr Gly Ser Asn Asp Glu Asn Glu Pro Glu Thr Cys
785                 790                 795                 800

Met Val Glu Lys Met Asn Leu Thr Phe His Val Ile Asn Thr Gly Asn
                805                 810                 815

Ser Met Ala Pro Asn Val Ser Val Glu Ile Met Val Pro Asn Ser Phe
            820                 825                 830

```
Ser Pro Gln Thr Asp Lys Leu Phe Asn Ile Leu Asp Val Gln Thr Thr
            835                 840                 845

Thr Gly Glu Cys His Phe Glu Asn Tyr Gln Arg Val Cys Ala Leu Glu
850                 855                 860

Gln Gln Lys Ser Ala Met Gln Thr Leu Lys Gly Ile Val Arg Phe Leu
865                 870                 875                 880

Ser Lys Thr Asp Lys Arg Leu Leu Tyr Cys Ile Lys Ala Asp Pro His
                885                 890                 895

Cys Leu Asn Phe Leu Cys Asn Phe Gly Lys Met Glu Ser Gly Lys Glu
                900                 905                 910

Ala Ser Val His Ile Gln Leu Glu Gly Arg Pro Ser Ile Leu Glu Met
            915                 920                 925

Asp Glu Thr Ser Ala Leu Lys Phe Glu Ile Arg Ala Thr Gly Phe Pro
930                 935                 940

Glu Pro Asn Pro Arg Val Ile Glu Leu Asn Lys Asp Glu Asn Val Ala
945                 950                 955                 960

His Val Leu Leu Glu Gly Leu His His Gln Arg Pro Lys Arg Tyr Phe
                965                 970                 975

Thr Ile Val Ile Ile Ser Ser Leu Leu Leu Gly Leu Ile Val Leu
                980                 985                 990

Leu Leu Ile Ser Tyr Val Met Trp Lys Ala Gly Phe Phe Lys Arg Gln
            995                 1000                1005

Tyr Lys Ser Ile Leu Gln Glu  Glu Asn Arg Arg Asp  Ser Trp Ser
    1010                1015                1020

Tyr Ile Asn Ser Lys Ser Asn  Asp Asp
    1025                1030
```

<210> SEQ ID NO 4
<211> LENGTH: 798
<212> TYPE: PRT
<213> ORGANISM: Homo sapiens

<400> SEQUENCE: 4

```
Met Asn Leu Gln Pro Ile Phe Trp Ile Gly Leu Ile Ser Ser Val Cys
1               5                   10                  15

Cys Val Phe Ala Gln Thr Asp Glu Asn Arg Cys Leu Lys Ala Asn Ala
                20                  25                  30

Lys Ser Cys Gly Glu Cys Ile Gln Ala Gly Pro Asn Cys Gly Trp Cys
            35                  40                  45

Thr Asn Ser Thr Phe Leu Gln Glu Gly Met Pro Thr Ser Ala Arg Cys
50                  55                  60

Asp Asp Leu Glu Ala Leu Lys Lys Lys Gly Cys Pro Pro Asp Asp Ile
65                  70                  75                  80

Glu Asn Pro Arg Gly Ser Lys Asp Ile Lys Lys Asn Lys Asn Val Thr
                85                  90                  95

Asn Arg Ser Lys Gly Thr Ala Glu Lys Leu Lys Pro Glu Asp Ile Thr
            100                 105                 110

Gln Ile Gln Pro Gln Gln Leu Val Leu Arg Leu Arg Ser Gly Glu Pro
        115                 120                 125

Gln Thr Phe Thr Leu Lys Phe Lys Arg Ala Glu Asp Tyr Pro Ile Asp
    130                 135                 140

Leu Tyr Tyr Leu Met Asp Leu Ser Tyr Ser Met Lys Asp Asp Leu Glu
145                 150                 155                 160

Asn Val Lys Ser Leu Gly Thr Asp Leu Met Asn Glu Met Arg Arg Ile
                165                 170                 175
```

```
Thr Ser Asp Phe Arg Ile Gly Phe Gly Ser Phe Val Glu Lys Thr Val
            180                 185                 190
Met Pro Tyr Ile Ser Thr Thr Pro Ala Lys Leu Arg Asn Pro Cys Thr
        195                 200                 205
Ser Glu Gln Asn Cys Thr Ser Pro Phe Ser Tyr Lys Asn Val Leu Ser
    210                 215                 220
Leu Thr Asn Lys Gly Glu Val Phe Asn Glu Leu Val Gly Lys Gln Arg
225                 230                 235                 240
Ile Ser Gly Asn Leu Asp Ser Pro Glu Gly Gly Phe Asp Ala Ile Met
                245                 250                 255
Gln Val Ala Val Cys Gly Ser Leu Ile Gly Trp Arg Asn Val Thr Arg
            260                 265                 270
Leu Leu Val Phe Ser Thr Asp Ala Gly Phe His Phe Ala Gly Asp Gly
        275                 280                 285
Lys Leu Gly Gly Ile Val Leu Pro Asn Asp Gly Gln Cys His Leu Glu
    290                 295                 300
Asn Asn Met Tyr Thr Met Ser His Tyr Tyr Asp Tyr Pro Ser Ile Ala
305                 310                 315                 320
His Leu Val Gln Lys Leu Ser Glu Asn Asn Ile Gln Thr Ile Phe Ala
                325                 330                 335
Val Thr Glu Glu Phe Gln Pro Val Tyr Lys Glu Leu Lys Asn Leu Ile
            340                 345                 350
Pro Lys Ser Ala Val Gly Thr Leu Ser Ala Asn Ser Ser Asn Val Ile
        355                 360                 365
Gln Leu Ile Ile Asp Ala Tyr Asn Ser Leu Ser Ser Glu Val Ile Leu
    370                 375                 380
Glu Asn Gly Lys Leu Ser Glu Gly Val Thr Ile Ser Tyr Lys Ser Tyr
385                 390                 395                 400
Cys Lys Asn Gly Val Asn Gly Thr Gly Glu Asn Gly Arg Lys Cys Ser
                405                 410                 415
Asn Ile Ser Ile Gly Asp Glu Val Gln Phe Glu Ile Ser Ile Thr Ser
            420                 425                 430
Asn Lys Cys Pro Lys Lys Asp Ser Asp Ser Phe Lys Ile Arg Pro Leu
        435                 440                 445
Gly Phe Thr Glu Glu Val Glu Val Ile Leu Gln Tyr Ile Cys Glu Cys
    450                 455                 460
Glu Cys Gln Ser Glu Gly Ile Pro Glu Ser Pro Lys Cys His Glu Gly
465                 470                 475                 480
Asn Gly Thr Phe Glu Cys Gly Ala Cys Arg Cys Asn Glu Gly Arg Val
                485                 490                 495
Gly Arg His Cys Glu Cys Ser Thr Asp Glu Val Asn Ser Glu Asp Met
            500                 505                 510
Asp Ala Tyr Cys Arg Lys Glu Asn Ser Ser Glu Ile Cys Ser Asn Asn
        515                 520                 525
Gly Glu Cys Val Cys Gly Gln Cys Val Cys Arg Lys Arg Asp Asn Thr
    530                 535                 540
Asn Glu Ile Tyr Ser Gly Lys Phe Cys Glu Cys Asp Asn Phe Asn Cys
545                 550                 555                 560
Asp Arg Ser Asn Gly Leu Ile Cys Gly Gly Asn Gly Val Cys Lys Cys
                565                 570                 575
Arg Val Cys Glu Cys Asn Pro Asn Tyr Thr Gly Ser Ala Cys Asp Cys
            580                 585                 590
```

-continued

```
Ser Leu Asp Thr Ser Thr Cys Glu Ala Ser Asn Gly Gln Ile Cys Asn
        595                 600                 605

Gly Arg Gly Ile Cys Glu Cys Gly Val Cys Lys Cys Thr Asp Pro Lys
    610                 615                 620

Phe Gln Gly Gln Thr Cys Glu Met Cys Gln Thr Cys Leu Gly Val Cys
625                 630                 635                 640

Ala Glu His Lys Glu Cys Val Gln Cys Arg Ala Phe Asn Lys Gly Glu
                645                 650                 655

Lys Lys Asp Thr Cys Thr Gln Glu Cys Ser Tyr Phe Asn Ile Thr Lys
            660                 665                 670

Val Glu Ser Arg Asp Lys Leu Pro Gln Pro Val Gln Pro Asp Pro Val
        675                 680                 685

Ser His Cys Lys Glu Lys Asp Val Asp Asp Cys Trp Phe Tyr Phe Thr
    690                 695                 700

Tyr Ser Val Asn Gly Asn Asn Glu Val Met Val His Val Val Glu Asn
705                 710                 715                 720

Pro Glu Cys Pro Thr Gly Pro Asp Ile Ile Pro Ile Val Ala Gly Val
                725                 730                 735

Val Ala Gly Ile Val Leu Ile Gly Leu Ala Leu Leu Leu Ile Trp Lys
            740                 745                 750

Leu Leu Met Ile Ile His Asp Arg Arg Glu Phe Ala Lys Phe Glu Lys
        755                 760                 765

Glu Lys Met Asn Ala Lys Trp Asp Thr Gly Glu Asn Pro Ile Tyr Lys
    770                 775                 780

Ser Ala Val Thr Thr Val Val Asn Pro Lys Tyr Glu Gly Lys
785                 790                 795
```